(12) United States Patent
Mitrofanova et al.

(10) Patent No.: US 11,299,786 B2
(45) Date of Patent: Apr. 12, 2022

(54) GENE PANEL TO PREDICT RESPONSE TO ANDROGEN DEPRIVATION IN PROSTATE CANCER

(71) Applicant: Rutgers, The State University of New Jersey, New Brunswick, NJ (US)

(72) Inventors: Antonina Mitrofanova, New York, NY (US); Sukanya Panja, Harrison, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 234 days.

(21) Appl. No.: 16/504,070

(22) Filed: Jul. 5, 2019

(65) Prior Publication Data

US 2020/0010909 A1 Jan. 9, 2020

Related U.S. Application Data

(60) Provisional application No. 62/694,085, filed on Jul. 5, 2018.

(51) Int. Cl.
*C12Q 1/6886* (2018.01)
*C12Q 1/6837* (2018.01)

(52) U.S. Cl.
CPC ......... *C12Q 1/6886* (2013.01); *C12Q 1/6837* (2013.01); *C12Q 2531/113* (2013.01); *C12Q 2600/112* (2013.01); *C12Q 2600/118* (2013.01); *C12Q 2600/154* (2013.01); *C12Q 2600/158* (2013.01)

(58) Field of Classification Search
CPC ............... C12Q 1/6886; C12Q 1/6837; C12Q 2600/154; C12Q 2600/112; C12Q 2600/158; C12Q 2600/118; C12Q 2600/106

See application file for complete search history.

(56) References Cited

U.S. PATENT DOCUMENTS

| 6,828,429 B1 | 12/2004 | Srivastava et al. |
| 9,289,436 B2 | 3/2016 | Szmulewitz et al. |
| 2012/0135877 A1 | 5/2012 | Jarrard et al. |
| 2013/0022974 A1 | 1/2013 | Chinnaiyan et al. |

FOREIGN PATENT DOCUMENTS

| EP | 2 878 678 A1 | 6/2015 | |
| WO | WO 2009/077158 A1 | 6/2009 | |
| WO | WO 2015/082414 A1 | 6/2015 | |
| WO | WO-2017059549 A1 * | 4/2017 | ....... G01N 33/57434 |

OTHER PUBLICATIONS

Chan. G&P Magazine. 2006. 6(3):20-26. (Year: 2006).*

(Continued)

*Primary Examiner* — Joseph G. Dauner
(74) *Attorney, Agent, or Firm* — Klarquist Sparkman, LLP

(57) ABSTRACT

Methods for predicting the response of prostate cancer to androgen deprivation therapy (ADT) using a gene signature of five genes (CSPG5, FKBP6, FOSB, STMN1, and TTC27) is provided. Also provided are sets containing specific binding molecules for each of CSPG5, FKBP6, FOSB, STMN1, and TTC27 and kits containing such sets.

19 Claims, 10 Drawing Sheets
(10 of 10 Drawing Sheet(s) Filed in Color)
Specification includes a Sequence Listing.

(56) References Cited

OTHER PUBLICATIONS

Chen et al. Molecular & Cellular Proteomics. 2002. 1:304-313. (Year: 2002).*
Greenbaum et al. Genome Biology. 2003. 4:117. (Year: 2003).*
Kendrick. "A gene's mRNA level does not usually predict its protein level". Kendrick Labs, Inc. Sep. 25, 2014. (Year: 2014).*
Mair et al. FEBS Letters. 2009. 583:3966-3973. (Year: 2009).*
Affymetrix. Retrieved on Jul. 20, 2021 from the internet: https://www.affymetrix.com/analysis/netaffx/xmlquery.affx?netaffx=netaffx4_annot. (Year: 2021).*
Winn et al. BMC Genomics. 2011. 12:412. (Year: 2011).*
Jia et al. Cancer Res. 2011. 71(7):2476-2487. (Year: 2011).*
LaMotte, "skip chemo, study says," https://www.cnn.com/2018/06/03/health/breast-cancer-recurrence-chemo-study/index.html, Jun. 3, 2018.
Panja et al., "Integrative (epi) Genomic Analysis to Predict Response to Androgen-Deprivation Therapy in Prostate Cancer," *EBioMedicine* 31:110-121, 2018.
Sparano et al., "Adjuvant Chemotherapy Guided by a 21-Gene Expression Assay in Breast Cancer," *N Engl J Med*. 379(2):111-121, 2018.

\* cited by examiner

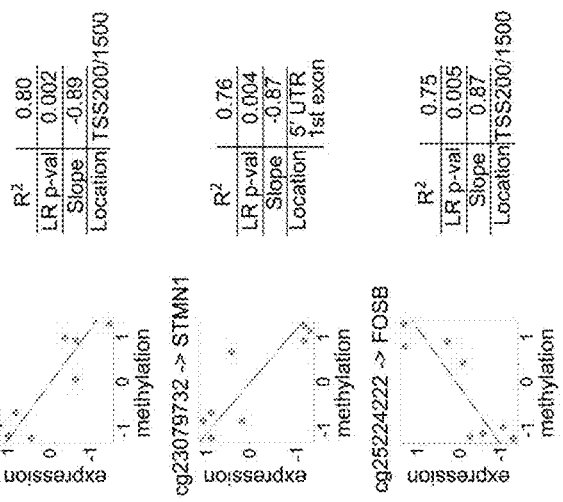
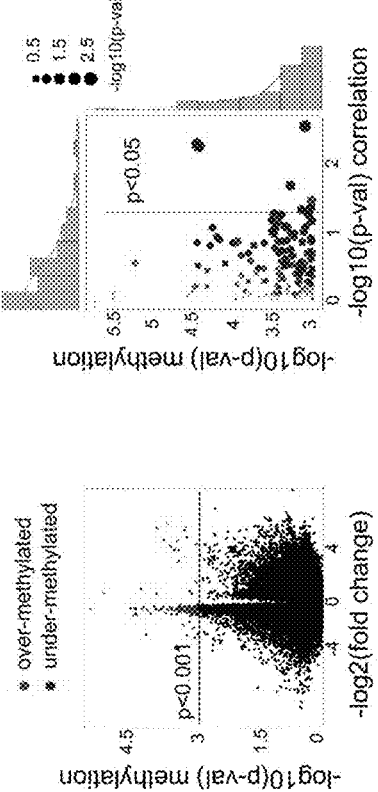
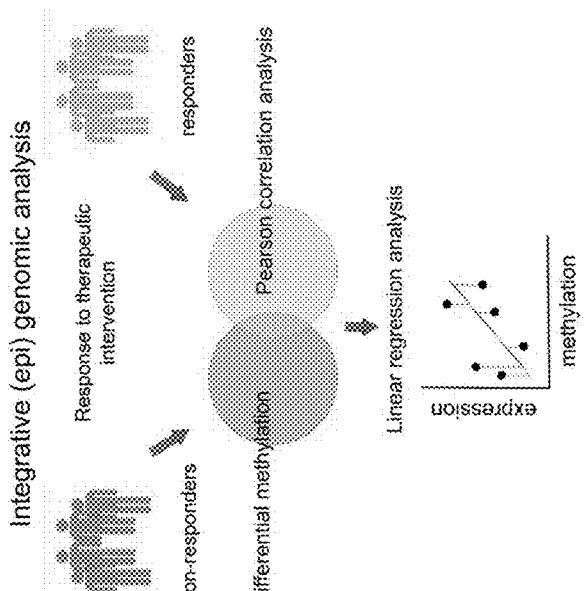
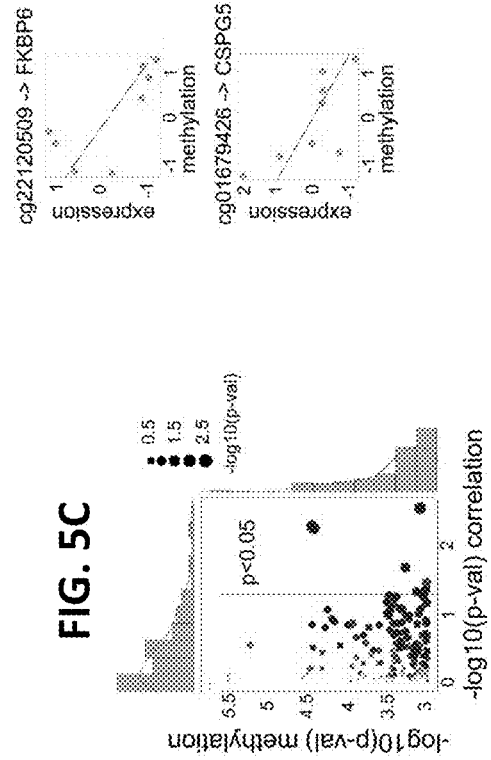
FIG. 5A
FIG. 5B
FIG. 5C
FIG. 5D

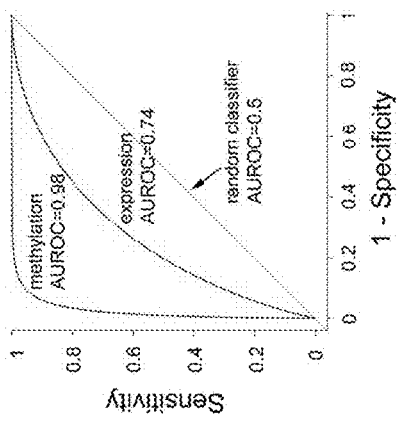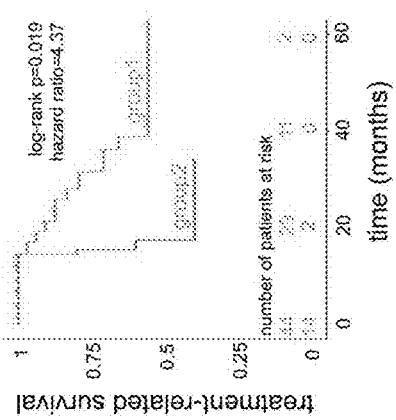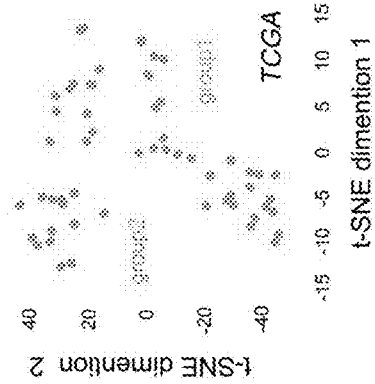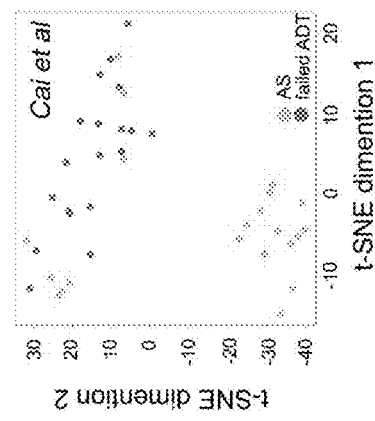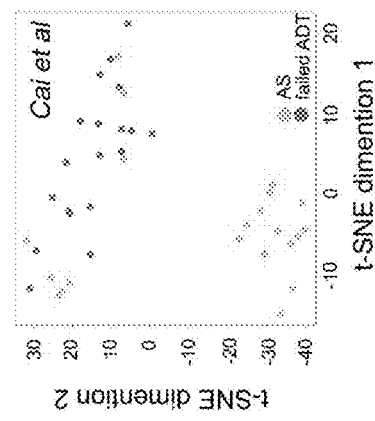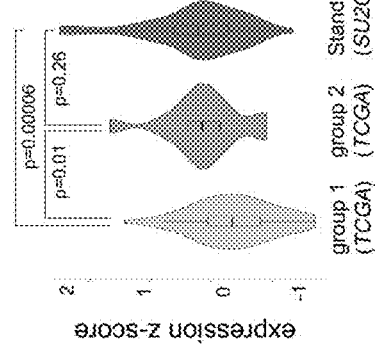

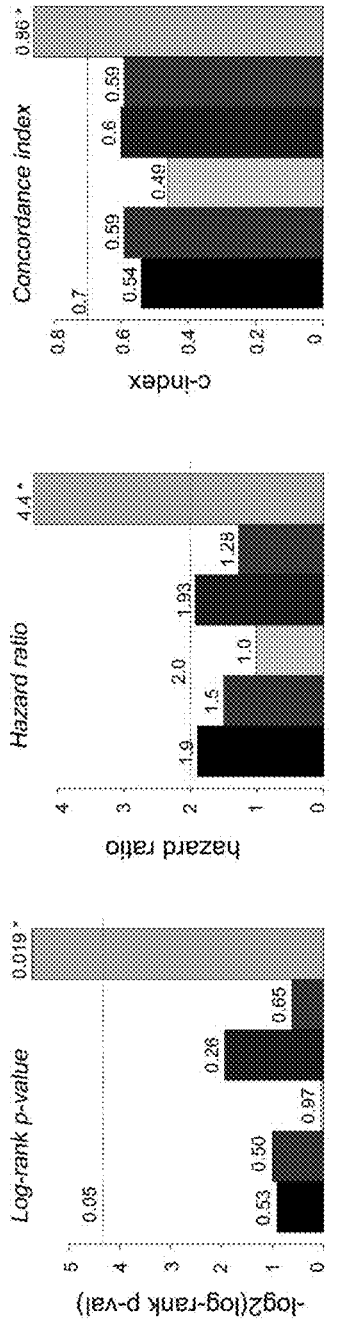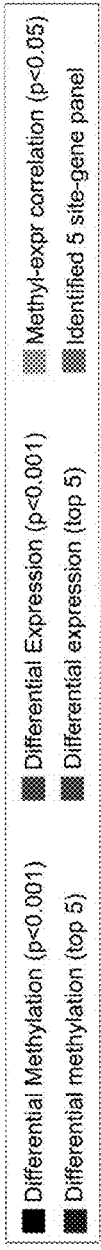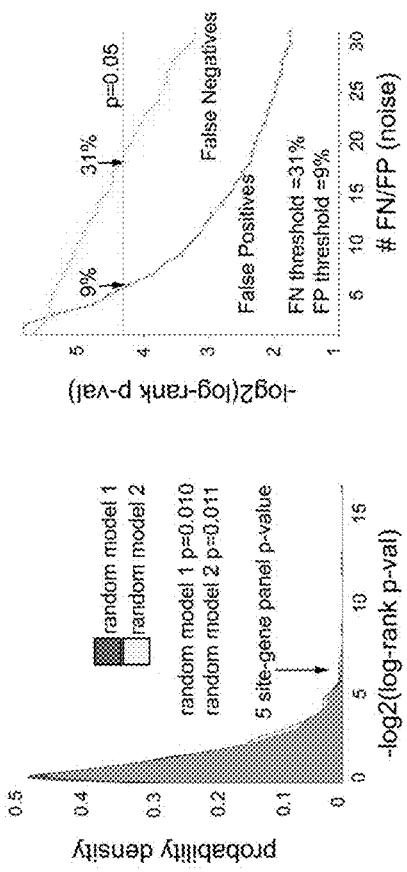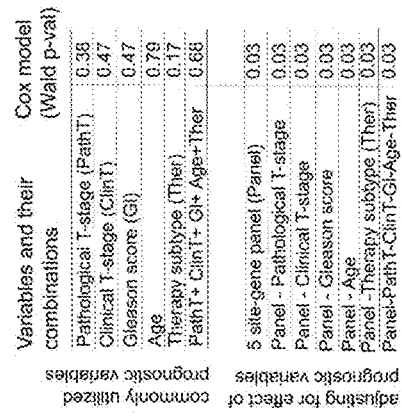
FIG. 8A
FIG. 8B
FIG. 8C
FIG. 8D

GENE PANEL TO PREDICT RESPONSE TO ANDROGEN DEPRIVATION IN PROSTATE CANCER

CROSS-REFERENCE TO RELATED APPLICATION

This application claims priority to U.S. Provisional application No. 62/694,085 filed Jul. 5, 2018, herein incorporated by reference in its entirety.

FIELD

This disclosure relates to methods for predicting response of prostate cancer to androgen deprivation therapy (ADT) using a gene signature of five genes, as well as sets of specific binding molecules and kits.

BACKGROUND

Prostate cancer is the most common malignancy and one of the leading causes of death in American men (Haas et al., 2008, Bray et al., 2013, Siegel et al., 2016). Androgen-deprivation has been the mainstay of treatment for patients with advanced disease. Even though majority of patients initially respond to androgen-deprivation therapy (ADT), remission lasts 2-3 years on average, with eventual relapse and progression to castration-resistant disease, which is nearly always metastatic and lethal (Karantanos et al., 2013, Lallous et al., 2016). Resistance to ADT and the paucity of the therapeutic options for patients with castration-resistant disease are among major clinical challenges in prostate cancer management (Chandrasekar et al., 2015, Wallace et al., 2014, Stoyanova et al., 2016).

While multifaceted and heterogeneous, prostate cancer is characterized by the scarcity of genomic mutations (Marzese and Hoon, 2015) and absence of well-defined subtypes (Abeshouse et al., 2015, Schoenborn et al., 2013, Shen and Abate-Shen, 2010), thus, making therapeutic management challenging. In the last decade, epigenomics has been at the center of scientific interest, including recognition of its role in cancer initiation and progression (Baxter et al., 2014, Sharma et al., 2010, Yao et al., 2015, Dhingra et al., 2017, Urbanucci et al., 2017). In recent years, one of the most commonly observed epigenomic means, chromatin accessibility (i.e., DNA methylation), has received attention due to its role in cell development (Smith and Meissner, 2013), genomic imprinting (i.e., biological process through which a gene carries information about its ancestor) (Butler, 2009), ageing (Johnson et al., 2012) and carcinogenesis (Luczak and Jagodzinski, 2006, Wajed et al., 2001). DNA methylation (FIG. 1) is the addition of methyl group to the fifth position of cytosine (converting it to 5-methylcytosine). In mammals, methylation of cytosine often occurs in regions where cytosine is followed by guanine (connected through phosphate molecule), named a CpG site (Deaton and Bird, 2011, Illingworth and Bird, 2009). A DNA region with frequent occurrences of CpG sites is commonly known as a CpG island or CGI (Illingworth and Bird, 2009, Gardiner-Garden and Frommer, 1987). Interestingly, 70% of gene promoter regions are associated with the CGIs, which can alter gene regulation (Deaton and Bird, 2011). If a CGI within the promoter region is methylated, it becomes occupied by the Methylated DNA Binding Protein (MDBP) (Zhang et al., 1986), which competes with transcription factor binding. MDBP can act as a transcription repressor or enhancer (Sengupta et al., 1999, Zhang et al., 1990), depending on the transcription process it interferes with.

Integrative analysis is crucial for in-depth understanding of molecular mechanisms involved in therapeutic response, for example (i) correlation between DNA methylation and mRNA expression of FHIT has been suggested as a marker for risk management in non-small cell lung and breast cancer (Zöchbauer-Müller et al., 2001); (ii) aberrant frequencies of genes correlated between DNA methylation (as well as copy number variation) and expression levels could identify molecular subtypes in hepatocellular carcinoma patients (Woo et al., 2017); (iii) correlation between DNA methylation and gene expression defined transcriptional patterns in molecular subtypes of breast cancer (Rhee et al., 2013), etc. Thus, a systematic investigation of the effect of DNA methylation on therapeutic response and analysis of its functional effect on the expression of the harboring genes can enhance our understanding of the mechanisms implicated in resistance and provide valuable predictive markers of predisposition to therapeutic failure.

SUMMARY

Therapeutic resistance is a central problem in clinical oncology. This disclosure provides methods to allow prioritization of prostate cancer patients with favorable and poor androgen-deprivation therapy (ADT) response. Using a method that integrated DNA methylation and mRNA expression data, a panel of five differentially methylated sites were identified which explain expression changes in their site-harboring genes, and demonstrated their ability to predict primary resistance to ADT in the TCGA prostate cancer patient cohort (hazard ratio=4.37). Furthermore, this panel accurately predicted response to ADT across independent prostate cancer cohorts, which was not affected by Gleason, age, or therapy subtypes. Based on these observations, this panel can be utilized to prioritize patients who would benefit from ADT and patients at risk of resistance that should be offered an alternative regimen.

Provided herein are methods of detecting expression, DNA methylation, or both, of a plurality of markers. The methods can include detecting or measuring expression of chondroitin sulfate proteoglycan 5 (CSPG5), FK506-binding protein 6 (FKBP6), FBJ murine osteosarcoma viral oncogene homolog B (FOSB), stathmin (STMN1), and tetratricopeptide repeat domain 27 (TTC27) in a prostate cancer sample, measuring DNA methylation of CSPG5, FKBP6, FOSB, STMN1, and TTC27 in a prostate cancer sample, or both. In some examples the expression and/or DNA methylation measured is compared to a control, such as compared to expression and/or DNA methylation in a prostate cancer sample from a patient known to respond to ADT (or to a reference value or range of values representing such).

Also provided herein are methods of identifying a subject with prostate cancer who will respond to ADT. Such methods can include measuring or detecting expression of CSPG5, FKBP6, FOSB, STMN1, and TTC27 in a prostate cancer sample from the subject relative to a control and/or measuring or detecting DNA methylation of CSPG5, FKBP6, FOSB, STMN1, and TTC27 in a prostate cancer sample from the subject relative to a control. It is then determined that the subject with prostate cancer will not respond to ADT when it is determined that TTC27, STMN1, and CSPG5 have increased expression in the prostate cancer sample from the subject relative to the control and that FOSB and FKBP6 have decreased expression in the prostate cancer sample from the subject relative to the control and/or when it is determined that FKBP6 has increased DNA methylation in the prostate cancer sample from the subject relative to the control and that FOSB, TTC27, STMN1, and CSPG5 have decreased DNA methylation in the prostate cancer sample from the subject relative to the control. In contrast, it is determined that the subject with prostate cancer will respond to ADT when it is determined that TTC27, STMN1, and CSPG5 have decreased expression in the prostate cancer sample from the subject relative to the control and that FOSB and FKBP6 have increased expression in the prostate cancer sample from the subject relative to the control and/or when it is determined that FKBP6 has decreased DNA methylation in the prostate cancer sample from the subject relative to the control and that FOSB, TTC27, STMN1, and CSPG5 have increased DNA methylation in the prostate cancer sample from the subject relative to the control. In such examples, the control can be expression and/or DNA methylation in a prostate cancer sample from a patient known to respond to ADT (or to a reference value or range of values representing such).

Methods of treating prostate cancer are provided. Such methods can include measuring or detecting expression of CSPG5, FKBP6, FOSB, STMN1, and TTC27 in a prostate cancer sample from the subject relative to a control and/or measuring or detecting DNA methylation of CSPG5, FKBP6, FOSB, STMN1, and TTC27 in a prostate cancer sample from the subject relative to a control. The method further includes administering a therapeutically effective amount of ADT to the subject if it is determined that they will respond to ADT, for example, if it is determined that TTC27, STMN1, and CSPG5 have increased expression in the prostate cancer sample from the subject relative to the control and that FOSB and FKBP6 have decreased expression in the prostate cancer sample from the subject relative to the control and/or when it is determined that FKBP6 has increased DNA methylation in the prostate cancer sample from the subject relative to the control and that FOSB, TTC27, STMN1, and CSPG5 have decreased DNA methylation in the prostate cancer sample from the subject relative to the control. In contrast, the method further includes administering radiation therapy, chemotherapy (e.g., docetaxel, cabazitaxel, mitoxantrone, estramustine, and/or prednisone) or combinations thereof if it is determined that they will not respond to ADT, for example, if it is determined that TTC27, STMN1, and CSPG5 have decreased expression in the prostate cancer sample from the subject relative to the control and that FOSB and FKBP6 have increased expression in the prostate cancer sample from the subject relative to the control and/or when it is determined that FKBP6 has decreased DNA methylation in the prostate cancer sample from the subject relative to the control and that FOSB, TTC27, STMN1, and CSPG5 have increased DNA methylation in the prostate cancer sample from the subject relative to the control.

In some examples, the method of treating prostate cancer includes measuring or detecting (i) decreased expression of TTC27, STMN1, and CSPG5 and decreased expression of FOSB and FKBP6 in a prostate cancer sample from the subject relative to a control, and/or (ii) decreased DNA methylation of FKBP6 and increased DNA methylation FOSB, TTC27, STMN1, and CSPG in a prostate cancer sample from the subject relative to a control. If such changes in expression and/or DNA methylation are detected in the prostate cancer sample, this indicates the subject from whom the sample was obtained will respond to ADT, and the method can include treating the subject with ADT (e.g., administering a therapeutically effective amount of an ADT regimen), there by treating the prostate cancer.

The disclosed methods can include additional steps, such as measuring prostate specific antigen (PSA) in a blood sample from the subject, determining a Gleason score for the prostate cancer, or combinations thereof. In some examples, the methods include obtaining the prostate cancer sample from the subject; contacting the prostate cancer sample from the subject and the control with one or more binding agents (e.g., nucleic acid probe, nucleic acid primer, antibody) specific for CSPG5, FKBP6, FOSB, STMN1, and TTC27; or combinations thereof. In some examples, the methods include measuring expression, DNA methylation, or both, of at least one housekeeping molecule, such as tubulin, beta-actin, or both.

In some examples, measuring expression includes measuring mRNA expression, protein expression, or both. In some examples measuring expression or measuring DNA methylation comprises using a microscope device.

In some examples the expression and/or DNA methylation measured is compared to a control, such as compared to expression and/or DNA methylation measure or detected in a prostate cancer sample from a patient known to respond to ADT (or compared to a reference value or range of values representing such).

Exemplary ADTs that can be administered to a subject identified as one having a prostate cancer that will respond to ADT include chemical castration, anti-androgen therapy, or both.

Also provided are sets of specific binding agents, such as sets of nucleic acid probes, nucleic acid primers, and/or antibodies (e.g., monoclonal or polyclonal or fragments thereof), which are specific for each of CSPG5, FKBP6, FOSB, STMN1, and TTC2. In some examples, such as set includes a nucleic acid probe, a nucleic acid primer, or antibody, specific for at least one housekeeping molecule (e.g., tubulin, beta-actin). In some examples, such a set is part of an array, for example the nucleic acid probes, nucleic acid primers, or antibodies, can be attached to a solid support. Kits that include a disclosed set of specific binding agents are also provided. Such a kit can further include other reagents, such as a buffer, such as a hybridization buffer. Such sets of specific binding agents and kits can be used to perform steps of the disclosed methods.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 2A) Schematic representation of a treatment time-course. Scenario 1: Time to treatment-related event: event occurred during the course of the treatment or within 1.5 years after the treatment end. Time between treatment start and a treatment-related event indicated. Scenario 2: Time to follow-up: time between treatment-start and latest follow-up indicated. (FIG. 2B) ADT response in the TCGA-PRAD cohort. Red vertical bars correspond to time between treatment start and event. Blue circles define censored patients (without events), indicating time between treatment start and latest follow-up. Non-responder (n=4) and responder (n=4) (Table 3) patients are indicated. (FIG. 2C) Schematic depiction of the differential methylation signature between non-responder and responder patients, sorted from sites whose methylation did not change (left tail) to sites with significant differential methylation (right tail). Signature was defined as a list of sites ordered by $-\log 10$ (p-value) from the two-sample two-tail t-test comparing non-responder and responder patient groups.

(FIG. 4A) Schematic diagram showing methylation regions profiled on the HumanMethylation450 array. (FIG. 4B) Scatter plots depicting enrichment of each region (i.e., site location) in the differential methylation signature. A reference methylation signature (as in FIG. 2C, ranked from the least differentially methylated (left) to the most differentially methylated (right)) is divided into 100 site-long steps and contribution of each region is calculated as % region inside each step. (FIG. 4C) Odds, Fisher Exact Test (FET) and Gene Set Enrichment Analysis (GSEA) demonstrate statistical significance of the region enrichment from FIG. 4B. For odds and FET, 500 most differentially methylated sites were considered for significance testing. For GSEA, differential methylation signature (FIG. 2C) was utilized as a reference and sites from each region were utilized as query sets. P-value was estimated with 1,000 site permutations.

FIGS. 5A-5D. Integrative (epi) genomic analysis identifies a 5 site-gene panel. (FIG. 5A) Schematic representation of the integrative (epi) genomic analysis: (top) identification of differentially methylated sites; (middle) Pearson correlation analysis (i.e., pre-screening) between methylation levels of the sites and mRNA expression levels of the site-harboring genes; (bottom) linear regression analysis to identify sites that can explain expression changes of the site-harboring genes. (FIG. 5B) Volcano plot of the differentially methylated sites, with under-methylated (blue) and over-methylated (red) sites indicated (at p-value<0.001, n=144). (FIG. 5C) Scatter plot depicting the relationship between differential methylation (y-axis) and site-gene (i.e., methylation-expression) Pearson correlation (x-axis) for the 144 significantly methylated sites from FIG. 4B. (FIG. 5D) Linear regression analysis between site methylation values and mRNA expression of their site-harboring genes (linear regression at p<0.05 shown), with non-responder (coral) and responder (aquamarine) samples indicated. The x and y axes depict z-scored methylation M-values and DESeq2 normalized expression values.

FIGS. 6A-6F. Five site-gene (epi) genomic panel predicts ADT failure in independent patient cohorts. (FIG. 6A) t-SNE clustering identifies two groups of patients: group 1 and group 2 (a full set of 5 dimensions considered). (FIG. 6B) Kaplan-Meier survival analysis identifies the significant difference in treatment-related survival (i.e., treatment response) between groups 1 and 2 from FIG. 5A. Log-rank p-value and hazard ratio are indicated. (FIG. 6C) ROC analysis: AUROC indicates the ability of methylated sites and expression of site harboring genes can classify patients into group 1 and group 2. (FIG. 6D) Violin plot for composite Stouffer integrated z-scores (see Materials and Methods) in group 1 (n=44), group 2 (n=14) and SU2C (n=51) cohorts. One-tail two-sample Welch t-test p-values are indicated. (FIG. 6E) t-SNE clustering (all 5 dimensions considered) based on 5 site-gene panel in Grasso et al cohort (n=91) (Grasso et al., 2012); and (FIG. 6F) Cai et al (n=40) (Cai et al., 2013) cohort; is able to separates androgen sensitive (AS, light blue) from castration-resistant prostate cancer (failed ADT, grey) samples (sensitivity=100% for failed ADT CRPC selection: 33/33 for Grasso et al., and 19/19 for Cai et al.).

(FIG. 7A) Treatment-related Kaplan-Meier survival analysis of candidate 5 site-gene panel in TCGA Gleason 7 and Gleason 8-9, demonstrating that therapeutic predictive ability of the identified 5 site-gene panel is independent of Gleason score. Log-rank p-values are indicated. (FIG. 7B) ROC analysis comparing TCGA-PRAD (group1) with Beltran et al (green) and PROMOTE (brown) patient cohorts. AUROC is indicated.

FIGS. 8A-8D. Multimodal comparative analysis demonstrates significance of the 5 site-gene panel. (FIG. 8A) Comparing 5 site-gene panel (grey bars) to commonly used methods, including differential methylation (black bars), differential expression (red bars), Pearson correlation between methylation and expression (pink bars), top 5 differentially methylated sites (dark red), and top 5 differentially expressed genes (brown) through log-rank p-value, hazard ratio and concordance index. * indicates statistically significant changes (log-rank p=0.019; HR p=0.03; c-index p=0.0001) (FIG. 8B) Random models to evaluate the ability of the 5 site-gene pairs chosen at random to separate patients into groups with different treatment response. Distributions of log-rank p-values from the random models indicate the significance of the predictive ability of our identified 5 site-gene panel. (FIG. 8C) Robustness analysis measuring predictive ability of the identified 5 site-gene panel across increasing FP and FN rates. (FIG. 8D) Multivariable Cox proportional hazard model demonstrates that commonly used prognostic clinical variables do not predict ADT response and do not affect predictive ability of the identified panel (Wald test Cox p-values indicated).

(FIG. 9A) Area Under ROC distribution (y-axis) as a function of varying methylation signature threshold (x-axis). (FIG. 9B) Area Under ROC distribution (y-axis) as a function of varying correlation threshold (x-axis). (FIG. 9C) Kaplan-Meier survival analysis on Sboner et al dataset demonstrates that therapeutic predictive ability of the identified 5 site-gene panel is independent of disease progression. Log-rank p-value and hazard ratio are indicated.

SEQUENCE LISTING

Figure 1:
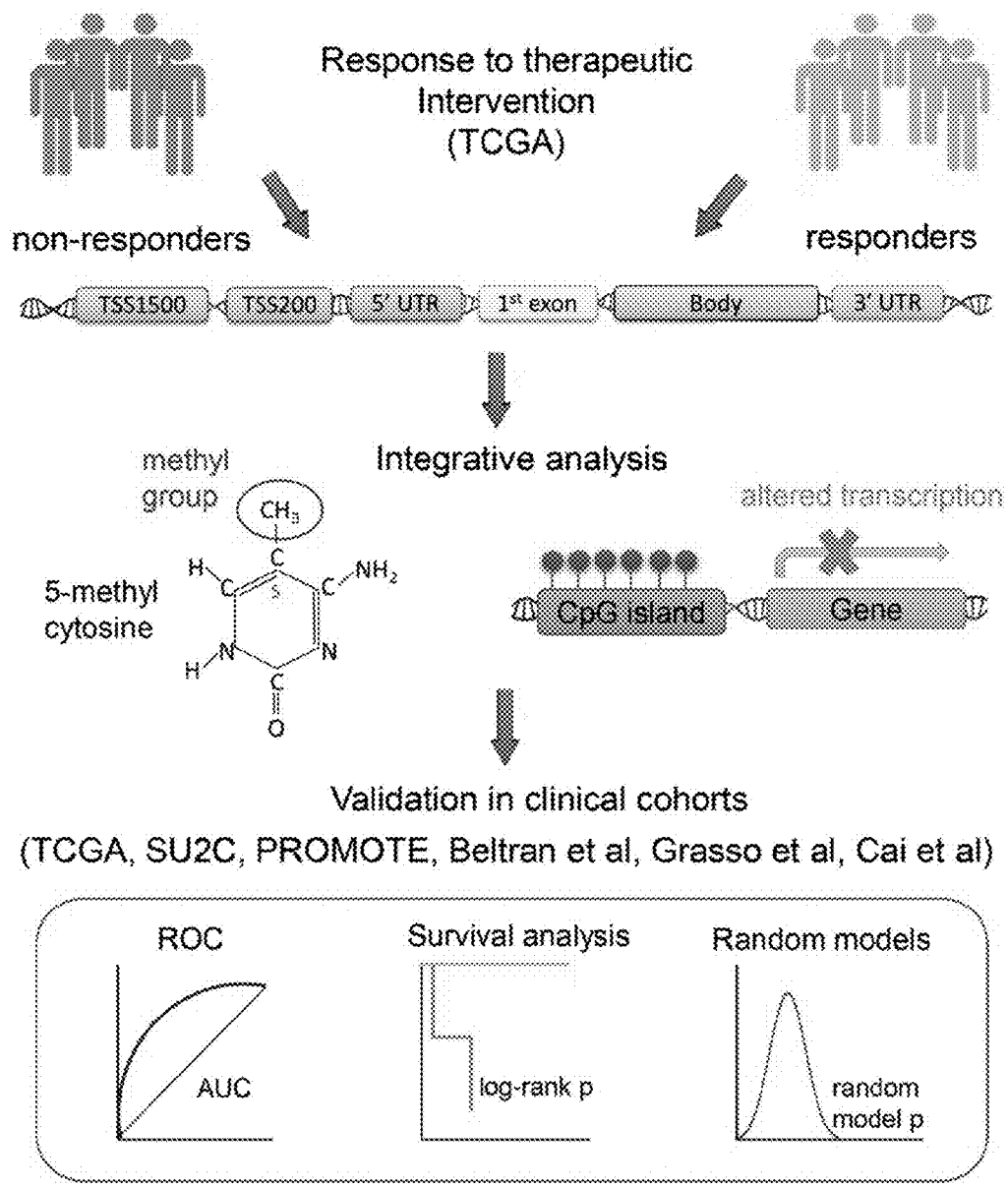
FIG. 1. Schematic representation of the systematic integrative approach. (Top) Non-responder and responder groups are compared for differentially methylated events/sites. (Middle) Differential methylation is integrated with expression of site-harboring genes. (Bottom) Candidate site-gene panel is evaluated for clinical significance.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 18, 2019, 14 KB, which is incorporated by reference herein. In the accompanying sequence listing:

SEQ ID NO: 1 is an exemplary human CSPG5 coding sequence.
SEQ ID NO: 2 is an exemplary human FKBP6 coding sequence.
SEQ ID NO: 3 is an exemplary human FOSB coding sequence.
SEQ ID NO: 4 is an exemplary human STMN1 coding sequence.
SEQ ID NO: 5 is an exemplary human TTC27 coding sequence.

DETAILED DESCRIPTION

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics*, 2nd Edition, 2003 (ISBN: 0-471-26821-6).

The singular forms "a," "an," and "the" refer to one or more than one, unless the context clearly dictates otherwise. For example, the term "comprising a drug" includes single or plural probes and is considered equivalent to the phrase "comprising at least one drug." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Jul. 5, 2018). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

In order to facilitate review of the various embodiments of the disclosure, the following explanations of specific terms are provided:

I. Terms

Adjunctive therapy: A treatment used in combination with a primary treatment to improve the effects of the primary treatment. For example, adjunctive therapy can include drug therapy (e.g., antiandrogen or chemical castration) that is administered following surgical resection of cancerous tissue. In example, adjunctive therapy can include surgery (such as prostatectomy) before or following ADT. In some examples, ADT is use as an adjunctive therapy with radiation therapy in the treatment of prostate cancer.

Administration: To provide or give a subject a therapeutic intervention, such as a therapeutic drug, procedure, or protocol (e.g., for a subject with prostate cancer, anti-androgen, prostatectomy, and active surveillance, respectively). Exemplary routes of administration for drug therapy include, but are not limited to, oral, injection (such as subcutaneous, intramuscular, intradermal, intraperitoneal, intratumoral, intraprostatic, and intravenous), sublingual, rectal, transdermal, intranasal, and inhalation routes. In one example administration of a drug is via an implant under the skin.

Androgen deprivation therapy (ADT): Also known as androgen suppression therapy, is an anti-hormone therapy used in the treatment of prostate cancer. ADT reduces the levels of androgen hormones, with drugs or surgery, to prevent prostate cancer cells from growing. Pharmaceutical approaches include antiandrogens (e.g., cyproterone acetate, flutamide, nilutamide, bicalutamide, enzalutamide, those that target testosterone synthesis (e.g., abiraterone acetate and seviteronel), target AR nuclear translocation (e.g., enzalutamide, apalutamide, and darolutamide), and combined therapies (e.g., galeterone). Another pharmaceutical approach is chemical castration. A surgical approach includes orchiectomy.

Binding or stable binding: An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a rapid increase in absorption at a characteristic temperature as the oligonucleotide (or analog) and target disassociate from each other, or melt. In another example, the method involves detecting a signal, such as one or more detectable labels, present on one or both nucleic acid molecules (or antibody or protein as appropriate). Methods of detecting binding of an antibody to a protein include Western blotting.

The binding between an oligomer (such as a probe or primer) and its target nucleic acid (such as CSPG5, FKBP6, FOSB, STMN1, or TTC27) can be characterized by the temperature ($T_m$) at which 50% of the oligomer is melted from its target. A higher ($T_m$) means a stronger or more stable complex relative to a complex with a lower ($T_m$).

Clinical outcome: Refers to the health status of a patient following treatment for a disease or disorder, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy (such as ADT).

Chondroitin sulfate proteoglycan 5 (CSPG5): e.g., OMIM 606775. Includes mammalian (such as human) CSPG5 nucleic acid molecules (e.g., gene, cDNA, and mRNA) and proteins. CSPG5 is a proteoglycan that may function as a neural growth and differentiation factor. The 539-amino acid human protein has a multidomain structure consisting of an N-terminal signal sequence, a chondroitin sulfate-attachment domain, an acidic amino acid cluster, an EGF-like domain, a transmembrane domain, and a cytoplasmic tail. The human and rat proteins share 86% homology. In humans, there are at least five different transcript variants (e.g., GenBank Accession Nos. NM_006574.3, NM_001206942.1, NM_001206943.1, NM_001206944.1, and NM_001206945.1, variants 1-5, respectively). In particular examples, CSPG5 DNA methylation and/or expression, along with DNA methylation and/or expression of FKBP6, FOSB, STMN1, and TTC27 is correlated with prostate cancer responsiveness to ADT.

CSPG5 sequences are publically available. For example, GenBank Accession Nos. NM_006574.3, NM_019284.1 and NM_013884.3 disclose exemplary human, rat, and mouse CSPG5 coding sequences, respectively. GenBank Accession Nos. NP_006565.2, NP_062157.1, and NP_038912.3 disclose exemplary human, rat, and mouse CSPG5 protein sequences, respectively. One skilled in the art will appreciate that CSPG5 nucleic acid and protein molecules analyzed using the disclosed methods can vary from those publicly available, while still being CSPG5 (e.g., one whose DNA methylation and/or expression, along with DNA methylation and/or expression of FKBP6, FOSB, STMN1, and TTC27, is correlated with prostate cancer responsiveness to ADT).

Contacting: Placement in direct physical association, including both solid and liquid forms. Contacting an agent with a cell can occur in vitro by adding the agent to isolated cells or in vivo by administering the agent to a subject. In one example, contacting a nucleic acid probe or primer with a target nucleic acid molecule (e.g., CSPG5, FKBP6, FOSB, STMN1, or TTC27) occurs in vitro by adding the nucleic acid probe or primer to a biological sample containing the nucleic acid molecule, or to isolated nucleic acid molecules obtained from the sample.

Control: A sample or standard used for comparison with an experimental sample, such as a prostate cancer sample, such as one known to respond to ADT (or one known not to respond to ADT). In some embodiments, the control is a historical control or standard reference value or range of values (e.g., a previously tested control sample, such as a group of prostate cancer patients who did or did not respond to ADT, or group of samples that represent baseline or normal values, such as the level of CSPG5, FKBP6, FOSB, STMN1, or TTC27 expression or methylation in normal prostate tissue). Laboratory standards and values can be set based on a known or determined population value and can be supplied in the format of a graph or table that permits comparison of measured, experimentally determined values.

Detecting or measuring expression: Determining the level expression in either a qualitative or quantitative manner by detection of nucleic acid molecules (e.g., at the genomic or mRNA level) or proteins. Exemplary methods include microarray analysis, PCR (such as RT-PCR), Northern blot, Western blot, ELISA, and mass spectrometry.

Differential/altered expression or differential/altered DNA methylation: A difference, such as an increase or decrease, in the conversion of the information encoded in a gene (such as a CSPG5, FKBP6, FOSB, STMN1, or TTC27) into messenger RNA, the conversion of mRNA to a protein, or both. It can also be an increase or decrease in the amount of DNA methylation of a gene (such as a CSPG5, FKBP6, FOSB, STMN1, or TTC27). In some examples, the difference is relative to a control or reference value (or range of values), such as the average expression value or average amount of DNA methylation value, of a group of subjects, such as prostate cancers that respond to ADT. Detecting differential expression and/or DNA methylation can include measuring a change in gene or protein expression and/or DNA methylation, such as a change in expression and/or DNA methylation of CSPG5, FKBP6, FOSB, STMN1, and TTC27, such as an increase of at least 20%, at least 50%, at least 75%, at least 90%, at least 100%, at least 200%, at least 300% at least 400%, or at least 500%, or a decrease of at least 20%, at least 50%, at least 75%, at least 90%, or at least 95%.

Downregulated or decreased: When used in reference to the expression of a nucleic acid molecule, refers to any process which results in a decrease in production of a gene product. A gene product can be RNA (such as microRNA, mRNA, rRNA, tRNA, and structural RNA) or protein. Therefore, gene downregulation or deactivation includes processes that decrease transcription of a gene or translation of mRNA. Gene downregulation includes any detectable decrease in the production of a gene product. In certain examples, production of a gene product decreases by at least 20%, at least 50%, at least 75%, at least 90%, at least 2-fold, at least 3-fold or at least 4-fold, as compared to a control (such an amount of expression in a prostate cancer sample from a patient(s) known to respond to ADT).

When used in reference to the DNA methylation of a nucleic acid molecule (e.g., gene), refers to any process which results in a decrease in the amount of DNA methylation observed or detected in a gene (such as a CSPG5, FKBP6, FOSB, STMN1, or TTC27). Decreased DNA methylation includes any detectable decrease in the DNA methylation of a gene. In certain examples, DNA methylation of a gene product decreases by at least 2-fold, for example at least 3-fold or at least 4-fold, as compared to a control (such an amount of DNA methylation in a prostate cancer sample from a patient(s) known to respond to ADT).

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, gene expression can be monitored to diagnose and/or prognose a subject with prostate cancer, such as predict a subject's ability to respond to ADT.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Gene expression profile (or fingerprint): Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and/or low expression of a defined set of genes (such as a CSPG5, FKBP6, FOSB, STMN1, and TTC27). A gene expression profile (also referred to as a fingerprint) can be linked to a tissue or cell type (such as prostate cancer), to a response to a therapy (such as ADT), or to any other distinct or identifiable condition that influences gene expression. Gene expression profiles can include relative as well as absolute expression levels of specific genes, and can be viewed in the context of a test sample compared to a baseline or control sample profile (such as a prostate cancer sample from a subject known to respond to ADT). In one example, a gene expression profile in a subject is read on an array (such as a nucleic acid or protein array).

FK506-binding protein 6 (FKBP6): e.g., OMIM 604839. Includes mammalian (such as human) FKBP6 nucleic acid molecules (e.g., gene, cDNA, and mRNA) and proteins. FKBP6 plays a role in homologous chromosome pairing in meiosis during spermatogenesis. Mutations in FKBP6 have been associated with male infertility in humans. FKBP6 is deleted in Williams syndrome, but this hemizygous loss of FKBP6 is not associated with infertility. An FKBP6 protein can include 3 α-helices and 11 β-sheet strands. In some examples, FKBP6 is an immunosuppressant. There are at least 4 transcript variants of FKBP6 (e.g., GenBank Accession Nos. NM_003602.4, NM_001135211.2, NM_001281304.1, NM_001362789.1, variants 1-4, respectively). In particular examples, FKBP6 expression and/or DNA methylation, along with DNA methylation and/or expression of CSPG5, FOSB, STMN1, and TTC27, is correlated with prostate cancer responsiveness to ADT.

FKBP6 sequences are publically available. For example, GenBank Accession Nos. NM_003602.4, NM_001105922.1 and NM_033571.3 disclose exemplary human, rat, and mouse FKBP6 coding sequences, respectively. GenBank Accession Nos. NP_003593.3, NP_001099392.1, and NP_291049.1 disclose exemplary human, rat, and mouse FKBP6 protein sequences, respectively. One skilled in the art will appreciate that FKBP6 nucleic acid and protein molecules analyzed using the disclosed methods can vary from those publicly available, while still being FKBP6 (e.g., one whose DNA methylation and/or expression, along with DNA methylation and/or expression of CSPG5, FOSB, STMN1, and TTC27, is correlated with prostate cancer responsiveness to ADT).

FBJ murine osteosarcoma viral oncogene homolog B (FOSB): e.g., OMIM 164772. Includes mammalian (such as human) FOSB nucleic acid molecules (e.g., gene, cDNA, and mRNA) and proteins. FOSB is a member of the FOS gene family, each of which encodes a leucine zipper protein that can dimerize with proteins of the JUN family (e.g., c-Jun, JunD), thereby forming the transcription factor complex AP-1. This FOSB is a subunit of the AP-1 transcription factor complex. As such, the FOS proteins have been implicated as regulators of cell proliferation, differentiation, and transformation. FosB and its truncated splice variants, ΔFosB (FOSB 1-237, missing the C-terminal 101 amino acids of FosB) and further truncated Δ2ΔFosB (FOSB 79-237), are all involved in osteosclerosis. There are at least 2 transcript variants of FosB (e.g., GenBank Accession Nos. NM_006732.2 and NM_001114171.1, variants 1-2, respectively). In particular examples, FOSB expression and/or DNA methylation, along with DNA methylation and/or expression of CSPG5, FKBP6, STMN1, and TTC27, is correlated with prostate cancer responsiveness to ADT.

FOSB sequences are publically available. For example, GenBank Accession Nos. NM_006732.2, NM_001256509.1 and NM_008036.2 disclose exemplary human, rat, and mouse FOSB coding sequences, respectively. GenBank Accession Nos. NP_006723.2, NP_001243438.1, and NP_032062.1 disclose exemplary human, rat, and mouse FOSB protein sequences, respectively. One skilled in the art will appreciate that FOSB nucleic acid and protein molecules analyzed using the disclosed methods can vary from those publicly available, while still being FOSB (e.g., one whose DNA methylation and/or expression, along with DNA methylation and/or expression of CSPG5, FKBP6, STMN1, and TTC27, is correlated with prostate cancer responsiveness to ADT).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (Detects Sequences that Share at Least 60% Identity)
Hybridization: 6×SSC at RT to 55° C. for 16-20 hours
Wash at least twice: 2×-3×SSC at RT to 55° C. for 20-30 minutes each.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Label: An agent capable of detection, for example by ELISA, spectrophotometry, flow cytometry, or microscopy. For example, a label can be attached (such as covalently attached) to a nucleic acid molecule (such as a nucleic acid probe) or protein (e.g., antibody or fragment thereof), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In particular examples, a label is conjugated to a binding agent that specifically binds to CSPG5, FKBP6, FOSB, STMN1, or TTC27.

Malignant: Cells that have the properties of anaplasia, invasion and metastasis.

Mammal: This term includes both human and non-human mammals.

Examples of mammals include, but are not limited to: humans, pigs, cows, goats, cats, dogs, rabbits and mice.

Nucleic acid array: An arrangement of nucleic acids (such as DNA or RNA) in assigned locations on a matrix, such as that found in cDNA arrays, mRNA arrays, or oligonucleotide arrays. In some examples, the nucleic acid molecules are attached covalently to the array.

Oligonucleotide: A plurality of joined nucleotides joined by native phosphodiester bonds, for example between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides. In one example, an oligonucleotide is a short sequence of nucleotides of CSPG5, FKBP6, FOSB, STMN1, or TTC27 (e.g., of any one of SEQ ID NOS: 1-5).

Oligonucleotide probe: A sequence of nucleotides, such as at least 8, at least 10, at least 15, at least 20, at least 21, at least 25, at least 30, at least 40, at least 50, or at least 55 nucleotides in length, used to detect the presence of a complementary sequence by molecular hybridization. In particular examples, oligonucleotide probes include one or more labels that permits detection of oligonucleotide probe: target sequence hybridization complexes. In one example, an oligonucleotide probe is used to detect the presence of CSPG5, FKBP6, FOSB, STMN1, or TTC27. Thus, in some examples, an oligonucleotide probe has sufficient complementary to a region of any one of SEQ ID NOS: 1-5. In some examples, an oligonucleotide probe has sufficient complementary to a promoter region of CSPG5, FKBP6, FOSB, STMN1, or TTC27, such as any one of SEQ ID NOS: 1-5.

Polymerase Chain Reaction (PCR): An in vitro amplification technique that increases the number of copies of a nucleic acid molecule (for example, a nucleic acid molecule in a sample or specimen). In an example, a biological sample collected from a subject (such as a prostate cancer sample) is contacted with a pair of oligonucleotide primers (such as those specific for CSPG5, FKBP6, FOSB, STMN1, or TTC27, such as any one of SEQ ID NOS: 1-5), under conditions that allow for the hybridization of the primers to nucleic acid template in the sample. The primers are extended under suitable conditions, dissociated from the template, and then re-annealed, extended, and dissociated to amplify the number of copies of the nucleic acid. The product of a PCR can be characterized by electrophoresis, restriction endonuclease cleavage patterns, oligonucleotide hybridization or ligation, and/or nucleic acid sequencing, or other techniques.

Primers: Short nucleic acid molecules, for instance DNA oligonucleotides 10 to 100 nucleotides in length, such as about 15, 20, 25, 30 or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, in order to obtain greater specificity, primers can be selected that include at least 20, at least 25, at least 30, at least 35, at least 40, at least 45, at least 50 or more consecutive nucleotides of target nucleic acid sequence (such as a CSPG5, FKBP6, FOSB, STMN1, or TTC27, such as any one of SEQ ID NOS: 1-5).

Prognosis: A prediction of the course of a disease, such as prostate cancer. The prediction can include determining the likelihood of a subject to develop aggressive, recurrent disease, to survive a particular amount of time (e.g. determine the likelihood that a subject will survive 1, 2, 3 or 5 years), to respond to a particular therapy (e.g., ADT), or combinations thereof.

Prostate cancer: Also known as carcinoma of the prostate, prostate cancer is the development of cancer in the prostate, a gland in the male reproductive system. Most prostate cancers are slow growing; however, some grow relatively quickly. The cancer cells may spread from the prostate to other parts of the body, particularly the bones and lymph nodes. Prostate cancer aggressiveness can be categorized as different risk categories for growth and spreading, including low-, intermediate-, and high-risk prostate cancers, which means that a patient has a low-, intermediate-, and high-risk, respectively, of pathological and biochemical outcomes after radical prostatectomy; metastasis; prostate cancer-specific mortality; and all-cause mortality (Cooperberg et al., J Cancer Inst., 101(12):878-887, 2009). For example, low-risk prostate cancer is slow-growing and not likely to spread quickly; however, high-risk prostate cancer is aggressive, meaning it is likely to spread quickly outside the prostate. Intermediate-risk patients are a heterogeneous group with cancers that tend to grow, but are not advanced or metastatic. Current means of assessing the risk uses Gleason scoring: low-risk prostate cancer, Gleason score sum less than or equal to 6; intermediate-risk prostate cancer, Gleason score sum at 7; and high-risk prostate cancer, Gleason score sum greater than 7.

Prostate cancer can also be assessed through staging, such as early or late stage prostate cancer. Early stage cancer includes cancers with a small tumor size, low levels of prostate-specific antigen (PSA), and/or low Gleason score (such as prostate cancer stages I and II using the four-stage Tumor/Nodes/Metastases system, or TNM system). In late stage prostate cancer (such as prostate cancer stages III and IV using the TNM system), difficulty urinating, blood in the urine, or pain in the pelvis, back or when urinating or to feeling tired due to low levels of red blood cells can be symptoms.

Prostate cancer can be diagnosed by biopsy. Medical imaging may then be done to determine if the cancer has spread to other parts of the body. Prostate cancer screening is controversial. Prostate-specific antigen (PSA) testing increases cancer detection but does not decrease mortality. Some cases can be safely followed with active surveillance or watchful waiting. Other treatments may include one or more of surgery (such as cryotherapy), radiation therapy, hormone therapy (e.g., ADT), and chemotherapy.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified mRNA preparation is one in which the mRNA is more pure than in an environment including a complex mixture of nucleic acid molecules.

Sample: A biological specimen containing genomic DNA, RNA (e.g., mRNA), protein, or combinations thereof, obtained from a subject. Examples include, but are not limited to, peripheral blood, serum, plasma, urine, ejaculate, saliva, tissue biopsy, fine needle aspirate, surgical specimen, and autopsy material. In one example, a sample is a prostate cancer sample. In some examples, samples are used directly in the methods provided herein. In some examples, samples are manipulated prior to analysis using the disclosed methods, such as through concentrating, filtering, centrifuging, diluting, desalting, denaturing, reducing, alkylating, proteolyzing, or combinations thereof. In some examples, components of the samples are isolated or purified prior to analysis using the disclosed methods, such as isolating cells, proteins, and/or nucleic acid molecules from the samples.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Queries searched with the blastn program are filtered with DUST (Hancock and Armstrong, 1994, *Comput. Appl. Biosci.* 10:67-70). Other programs may use SEG. In addition, a manual alignment can be performed. Proteins with even greater similarity will show increasing percentage identities when assessed by this method. Thus, in some examples, expression of a CSPG5, FKBP6, FOSB, STMN1, or TTC27 protein having at least 80%, at least 85%, at least 90%, at least 95%, at least 98%, or at least 99% sequence identity to a native CSPG5, FKBP6, FOSB, STMN1, or TTC27 protein sequence, while retaining the biological function of the protein, can be examined using the disclosed methods.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid. Thus, in some examples, expression of a CSPG5, FKBP6, FOSB, STMN1, or TTC27 nucleic acid (such as mRNA, cDNA, or gene) having at least 80%, at least 85%, at least 90%, at least 95%, at least 98%, or at least 99% sequence identity to a native CSPG5, FKBP6, FOSB, STMN1, or TTC27 nucleic acid (such as mRNA, cDNA, or gene, such as one that includes any of SEQ ID NOS: 1-5) sequence can be examined using the disclosed methods. One of skill in the art will appreciate that the particular sequence identity ranges are provided for guidance only.

Specific binding agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of CSPG5, FKBP6, FOSB, STMN1, and TTC2.

Thus, a nucleic acid-specific binding agent binds substantially only to the defined nucleic acid, such as mRNA or a gene sequence, or to a specific region within the nucleic acid. A protein-specific binding agent binds substantially only the defined protein, or to a specific region within the protein. For example, a "specific binding agent" includes antibodies and other agents that bind substantially to a specified polypeptide. Antibodies include monoclonal or polyclonal antibodies that are specific for the polypeptide, as well as immunologically effective portions ("fragments") thereof. The determination that a particular agent binds substantially only to a specific target may readily be made, for example by Western blotting and nucleic acid hybridization procedures.

Stathmin (STMN1): e.g., OMIM 151442. Includes mammalian (such as human) STMN1 nucleic acid molecules (e.g., gene, cDNA, and mRNA) and proteins. STMN1, also known as metablastin and oncoprotein 18, is a highly conserved protein that regulate the cell cytoskeleton. The protein includes an N-terminal domain, a coil-coil region, and a short C-terminal domain. STMN1 regulates microtubule dynamics by promoting depolymerization of microtubules or preventing polymerization of tubulin heterodimers. There are at least 4 transcript variants of STMN1 (e.g., GenBank Accession Nos. NM_203401.1, NM_203399.1, NM_005563.3, and NM_001145454.2 variants 1-4, respectively). In particular examples, STMN1 expression, along with CSPG5, FKBP6, FOSB, and TTC27 is correlated with prostate cancer responsiveness to ADT.

STMN1 sequences are publically available. For example, GenBank Accession Nos. NM_203401.1, NM_017166.1 and NM_019641.4 disclose exemplary human, rat, and mouse STMN1 coding sequences, respectively. GenBank Accession Nos. NP_005554.1, AAH62234.1, and AAH54396.1 disclose exemplary human, rat, and mouse FOSB protein sequences, respectively. One skilled in the art will appreciate that FOSB nucleic acid and protein molecules analyzed using the disclosed methods can vary from those publicly available, while still being STMN1 (e.g., one whose DNA methylation and/or expression, along with DNA methylation and/or expression of CSPG5, FKBP6, FOSB, and TTC27, is correlated with prostate cancer responsiveness to ADT).

Subject: Living multi-cellular vertebrate organisms, a category that includes human and non-human mammals. In one example, a subject is a male with prostate cancer. In one example, a subject has had a prostatectomy.

Target sequence: A sequence of nucleotides located in a particular region in a mammalian (e.g., human) genome that corresponds to a desired sequence, such as a ADT-associated gene, for example, CSPG5, FKBP6, FOSB, STMN1, or TTC27. Target sequences can encode target proteins, or can be a non-coding RNA. The target can be for instance a coding sequence, the non-coding strand that corresponds to a coding sequence, or a promoter region. Examples of target sequences include those sequences associated with responsiveness of prostate cancer to ADT.

Tetratricopeptide repeat domain 27 (TTC27): Includes mammalian (such as human) TTC27 nucleic acid molecules (e.g., gene, cDNA, and mRNA) and proteins. There are at least three transcript variants of TTC27 (e.g., GenBank Accession Nos. NM_017735.4, NM_001193509.1, and XR_002959314.1 variants 1-3, respectively). In particular examples, TTC27 expression, along with CSPG5, FKBP6, FOSB, and, STMN1 is correlated with prostate cancer responsiveness to ADT.

TTC27 sequences are publically available. For example, GenBank Accession Nos. NM_017735.4, NM_001106706.1, and NM_152817.4 disclose exemplary human, rat, and mouse TTC27 coding sequences, respectively. GenBank Accession Nos. AAH63791.1, NP_001100176.1, and AAH21912.1 disclose exemplary human, rat, and mouse TTC27 protein sequences, respectively. One skilled in the art will appreciate that FOSB nucleic acid and protein molecules analyzed using the disclosed methods can vary from those publicly available, while still being TTC27 (e.g., one whose DNA methylation and/or expression, along with DNA methylation and/or expression of CSPG5, FKBP6, FOSB, and, STMN1 is correlated with prostate cancer responsiveness to ADT).

Therapeutically effective amount: An amount of a composition that alone, or together with an additional therapeutic agent(s) (for example a chemotherapeutic agent, radiation therapy, or ADT), induces the desired response (e.g., treatment of a tumor). The preparations disclosed herein are administered in therapeutically effective amounts. In one example, a desired response is to decrease prostate cancer size or volume or metastasis in a subject to whom the therapy is administered. The prostate cancer or metastasis thereof does not need to be completely eliminated for the composition to be effective. For example, a composition can decrease the size or volume of a prostate tumor or the metastasis of the tumor by at least 20%, at least 50%, at least 60%, at least 70%, at least 80%, at least 90%, at least 95%, at least 98%, or even at least 100% (elimination of the tumor), as compared to the size or volume of the tumor or metastasis in the absence of the therapy.

In particular examples, it is an amount of the therapeutic agent effective to decrease the number of prostate cancer cells, such as the number of tumor cells in a patient with prostate cancer. The tumor cells do not need to be completely eliminated for the composition to be effective. For example, a composition can decrease the number of tumor cells by a desired amount, for example by at least 20%, at least 50%, at least 60%, at least 70%, at least 80%, at least 90%, at least 95%, at least 98%, or even at least 100% (elimination of detectable prostate cancer cells), as compared to the number of prostate cancer cells in the absence of the composition.

A therapeutically effective amount of a therapeutic agent can be administered in a single dose, or in several doses, for example daily, weekly, monthly, or yearly, during a course of treatment. However, the therapeutically effective amount can depend on the subject being treated, the severity and type of the condition being treated, the manner of administration and the type of therapeutic agent being administered.

Tissue: A plurality of functionally related cells. A tissue can be a suspension, a semi-solid, or solid. Tissue includes cells collected from a subject, such as from the liver.

Treating a disease: "Treatment" refers to a therapeutic intervention that ameliorates a sign or symptom of a disease or pathological condition, such as a sign or symptom of prostate cancer. Treatment can also induce remission or cure of a condition, such as prostate cancer. Treatment of a disease does not require a total absence of disease. For example, reduction in tumor size and/or volume, and/or decreases in the number metastases, size and/or volume of a metastasis, such as a decrease of at least 20%, at least 50%, at least 75%, or at least 90% can be sufficient. In some examples, treating a disease improves the prognosis of the prostate cancer patient, for example by increasing the predicted survival time of the prostate cancer patient (for example increases survival time by at least 6 months, at least 1 year, at least 3 years, or at least 5 years).

Tumor: All neoplastic cell growth and proliferation, whether malignant or benign, and all pre-cancerous and cancerous cells and tissues. In an example, a tumor is a prostate tumor.

Under conditions sufficient for: A phrase that is used to describe any environment that permits the desired activity. In one example, includes administering ADT to a subject with prostate cancer found using the methods provided herein to have a prostate cancer that will respond to ADT, sufficient to allow the desired activity, such as treatment of the prostate cancer. In one example, includes incubating or contacting binding agents specific for CSPG5, FKBP6, FOSB, STMN1, and TTC27 with a prostate cancer sample sufficient to allow the binding agents to bind or hybridize to CSPG5, FKBP6, FOSB, STMN1, and TTC27 nucleic acid molecules or proteins, respectively, in the prostate cancer sample.

Upregulated, activated, or increased: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Gene upregulation includes any detectable increase in the production of a gene product. In certain examples, production of a gene product increases by at least 20%, at least 50%, at least 75%, at least 90%, at least 2-fold, at least 3-fold or at least 4-fold, as compared to a control (such an amount of gene expression in a prostate cancer sample known to respond to ADT). In one example, a control is a relative amount of gene expression in a biological sample, such as in a prostate cancer sample (or plurality of such samples) obtained from a subject that responded to ADT.

When used in reference to the DNA methylation of a nucleic acid molecule (e.g., gene), refers to any process which results increase in the amount of DNA methylation observed or detected in a gene (such as a CSPG5, FKBP6, FOSB, STMN1, or TTC27). Increased DNA methylation includes any detectable increase in the DNA methylation of a gene. In certain examples, DNA methylation of a gene product increases by at least 20%, at least 50%, at least 75%, at least 90%, at least 2-fold, at least 3-fold or at least 4-fold, as compared to a control (such an amount of DNA methylation in a prostate cancer sample from a patient(s) known to respond to ADT). In one example, a control is a relative amount of gene expression in a biological sample, such as in a prostate cancer sample (or plurality of such samples) obtained from a subject that responded to ADT.

II. Overview

Disclosed is a systematic genome-wide integrative approach to analyze DNA methylation and its causal effect on mRNA gene expression to predict response to therapeutic intervention in cancer patients (see schematics in FIG. 1). This algorithm is termed Epi2GenR (Epigenomic and Genomic mechanisms of treatment Resistance). Genomic profiles from primary tumors of prostate cancer patients with poor (i.e., non-responders) and favorable (i.e., responders) response to androgen-deprivation therapy (ADT) were compared, which identified a panel of five differentially methylated sites, whose methylation changes explain expression variation in their site-harboring genes (CSPG5, FKBP6, FOSB, STMN1, and TTC27).

The five site-gene panel (CSPG5, FKBP6, FOSB, STMN1, and TTC27) was able to differentiate patients with predisposition to ADT failure from patients with favorable treatment response in TCGA-PRAD (Abeshouse et al., 2015) (log-rank p=0.0191, hazard ratio=4.37) and other (Grasso et al., 2012, Robinson et al., 2015, Cai et al., 2013, Beltran et al., 2011, Kohli et al., 2015) patient cohorts (sensitivity=100%, AUROC=0.83, AUROC=0.98). Significant non-random predictive ability of the five site-gene panel and its robustness to increased false positive (FP) and false negative (FN) rates was confirmed through random modeling and robustness analysis, respectively. Furthermore, this panel predicts therapeutic response and does not depend on commonly used prognostic variables, such as pathological and clinical T-stage, Gleason score (i.e., pathology-based grading system of prostate tissues), age, and therapy subtype.

This panel can be used to pre-screen patients to prioritize those who would benefit from ADT and patients at risk of developing resistance. The method can improve therapeutic management of cancer patients and builds a foundation for personalized therapeutic advice for patients with advanced malignancies.

Several features of this method distinguish it from previously utilized methods used for data analysis in oncology. Firstly, it introduces a systematic (epi) genomic data driven method for predictive analysis of therapeutic resistance and is an original method of its kind to the best of our knowledge. Second is its ability to identify functional "cause-effect" relationships between DNA methylation sites and mRNA expression of the site-harboring genes, which outperformed genomic approaches that rely on single data type (e.g., expression or methylation data alone) or their correlation alone, and significantly increases the probability of identifying (epi) genomic markers with functional role in therapeutic resistance. Thirdly, the approach introduces a highly non-random robust technique to classify patients at risk of resistance and those who would benefit from the specific therapeutic intervention.

III. ADT Molecular Markers

Current standard of care (SOC) for prostate cancer patients is that all patients with advanced prostate cancer are administered androgen-deprivation therapy (ADT). No criteria (either molecular or clinical) are used to prioritize/select patients to receive or not to receive this therapy. The disclosed five gene panel improves the SOC, as patients can be prioritized for androgen-deprivation treatment based on their risk of developing resistance or favorable response. In some examples, a subject identified as having a tumor that is responsive to ADT is administered ADT as a first-line of treatment, such as a subject with a with low risk of resistance, improving their disease course and outcome. For patients with high risk of ATD resistance, other regiments can be administered, such as radiation therapy and/or chemotherapy (as for such patients androgen-deprivation can lead to prostate cancer becoming more aggressive and turning into a castration-resistant prostate cancer, which is nearly always metastatic and lethal). In some examples, the subject analyzed or treated with the disclosed methods has advanced prostate cancer. In contrast to current SOC, where all advanced-stage prostate cancer patients receive AD therapy, such an advanced-stage prostate cancer subject would not receive ADT if they are found to not likely have a favorable response to such therapy using the disclosed methods. In other examples, the subject analyzed or treated with the disclosed methods has an early-stage prostate cancer, and is administered ADT if they are found to likely have a favorable response to such therapy. This is in contrast to current SOC, where early-stage prostate cancer is not treated with ADT.

The systematic integrative analysis of the ADT resistance in prostate cancer identified a panel of five differentially methylated sites harbored by FKBP6, TTC27, CSPG5, FOSB, and STMN1 genes. FOSB is a member of FOS gene family AP1 complexes, which bind to the promoter or enhancer regions of target genes (Lamph et al., 1988, Shahzad et al., 2010) and regulate cell survival, proliferation, angiogenesis, invasion, and metastasis (Shahzad et al., 2010, Shaulian and Karin, 2001, Shaulian and Karin, 2002, Tulchinsky, 2000, van Dam and Castellazzi, 2001). FOSB contributes towards increased concentration of IL-8 (interleukin-8) which influence angiogenesis, affecting cellular proliferation and metastases in ovarian cancer (Shahzad et al., 2010).

In recent years, clinical oncology has witnessed the emergence of a so-called neuroendocrine prostate cancer phenotype, with strong ties to failed response to ADT (Beltran et al., 2016, Lee et al., Akamatsu et al.). In fact, a substantial number of patients treated with enzalutamide or abiraterone relapse and develop neuroendocrine features (Epstein et al., 2014, Beltran et al., 2011).

The identified (epi) genomic panel of five site-genes are predictive of response to ADT. This panel can be utilized to pre-screen patients and identify those (i) who are at higher risk of developing resistance to ADT and who should potentially be advised an alternative therapeutic regimen (such as chemotherapy, radiation therapy etc.), thereby avoiding ADT side effects and improving disease-course; and (ii) who would benefit from ADT, making it their priority therapy choice. Furthermore, this panel can be utilized to prioritize patients for clinical trials.

Thus, provided herein are methods, which can be used to predict whether a subject diagnosed with prostate cancer will respond to ADT; to treat a subject diagnosed with prostate cancer (for example with ADT or not (and instead administer a non-ADT therapy, such as chemotherapy and/or radiation); or combinations thereof. In some examples, markers analyzed using the disclosed methods include, consist of, or consist essentially of CSPG5, FKBP6, FOSB, STMN1, and TTC27.

Provided herein are methods of detecting expression, DNA methylation, or both, of a plurality of markers. Such methods can include measuring or expression of CSPG5, FKBP6, FOSB, STMN1, and TTC27 in a prostate cancer sample, measuring or detecting DNA methylation of CSPG5, FKBP6, FOSB, STMN1, and TTC27 in a prostate cancer sample, or both.

Also provided herein are methods of identifying a subject with prostate cancer who will respond to ADT. Such methods can include measuring or detecting expression of CSPG5, FKBP6, FOSB, STMN1, and TTC27 in a prostate cancer sample from the subject relative to a control and/or measuring or detecting DNA methylation of CSPG5, FKBP6, FOSB, STMN1, and TTC27 in a prostate cancer sample from the subject relative to a control. The methods also include determining that the subject with prostate cancer will not respond to ADT when it is determined that (i) TTC27, STMN1, and CSPG5 have increased expression in the prostate cancer sample from the subject relative to the control and that FOSB and FKBP6 have decreased expression in the prostate cancer sample from the subject relative to the control and/or (ii) FKBP6 has increased DNA methylation in the prostate cancer sample from the subject relative to the control and that FOSB, TTC27, STMN1, and CSPG5 have decreased DNA methylation in the prostate cancer sample from the subject relative to the control. Alternatively, it is determined that the subject with prostate cancer will respond to ADT when it is determined that (i) TTC27, STMN1, and CSPG5 have decreased expression in the prostate cancer sample from the subject relative to the control and that FOSB and FKBP6 have increased expression in the prostate cancer sample from the subject relative to the control and/or (ii) FKBP6 has decreased DNA methylation in the prostate cancer sample from the subject relative to the control and that FOSB, TTC27, STMN1, and CSPG5 have increased DNA methylation in the prostate cancer sample from the subject relative to the control.

Methods of treating prostate cancer are provided. Such methods can include measuring or detecting expression of CSPG5, FKBP6, FOSB, STMN1, and TTC27 in a prostate cancer sample from the subject relative to a control and/or measuring or detecting DNA methylation of CSPG5, FKBP6, FOSB, STMN1, and TTC27 in a prostate cancer sample from the subject relative to a control. The methods also include determining that the subject with prostate cancer will not respond to ADT when it is determined that (i) TTC27, STMN1, and CSPG5 have increased expression in the prostate cancer sample from the subject relative to the control and that FOSB and FKBP6 have decreased expression in the prostate cancer sample from the subject relative to the control and/or (ii) FKBP6 has increased DNA methylation in the prostate cancer sample from the subject relative to the control and that FOSB, TTC27, STMN1, and CSPG5 have decreased DNA methylation in the prostate cancer sample from the subject relative to the control. Alternatively, it is determined that the subject with prostate cancer will respond to ADT when it is determined that (i) TTC27, STMN1, and CSPG5 have decreased expression in the prostate cancer sample from the subject relative to the control and that FOSB and FKBP6 have increased expression in the prostate cancer sample from the subject relative to the control and/or (ii) FKBP6 has decreased DNA methylation in the prostate cancer sample from the subject relative to the control and that FOSB, TTC27, STMN1, and CSPG5 have increased DNA methylation in the prostate cancer sample from the subject relative to the control. The method also includes administering ADT (such as chemical castration, anti-androgen therapy, or both) to the subject if it is determined that they will respond to ADT, or not administering ADT to the subject if it is determined that they will not respond to ADT (instead such subjects may be administered an alternative therapy, such as radiation therapy, chemotherapy (e.g., docetaxel, prednisone, cabazitaxel, mitoxantrone, and/or estramustine) or both).

In some examples, the method of treating prostate cancer in a subject with prostate cancer includes measuring or detecting (i) decreased expression of TTC27, STMN1, and CSPG5 and increased expression of FOSB and FKBP6 in a prostate cancer sample from the subject relative to a control and/or (ii) decreased DNA methylation of FKBP6 and increased DNA methylation FOSB, TTC27, STMN1, and CSPG5 in a prostate cancer sample from the subject relative to a control, and then administering ADT to the subject, thereby treating the prostate cancer.

The disclosed methods can further include measuring prostate specific antigen (PSA) in a blood sample from the subject, determining a Gleason score for the prostate cancer, or combinations thereof. In some examples, the methods further include obtaining the prostate cancer sample from the subject, contacting the prostate cancer sample from the subject (and in some examples a control prostate cancer sample from a subject(s) who responded to ADT) with one or more binding agents (e.g., nucleic acid probes, nucleic acid primers, antibodies) specific for CSPG5, FKBP6, FOSB, STMN1, and TTC27, or combinations thereof.

Measuring expression of CSPG5, FKBP6, FOSB, STMN1, and TTC27 can include measuring nucleic acid expression (e.g., mRNA, gene, cDNA), protein expression, or both. For example, polymerase chain reaction, sequencing, ELISA, and mass spectrometric methods can be used. In some examples, a microscope device is used.

In some examples, in addition to measuring CSPG5, FKBP6, FOSB, STMN1, and TTC27 expression and/or DNA methylation, expression, DNA methylation, or both, of at least one housekeeping molecule (e.g., beta-actin, tubulin) is also measured as a control (such as 1, 2, 3, 4, 5, 6, 7, 8, 9 or 10 housekeeping genes).

In some examples, the control is a reference value (or range of values) for an expected amount of CSPG5, FKBP6, FOSB, STMN1, and TTC27 expression and/or DNA methylation from a subject with a prostate cancer that will respond to ADT. In some examples, the control is a prostate cancer sample known to respond to ADT (which can be analyzed in parallel with a test sample).

The prostate cancer analyzed or treated with the disclosed methods can be a primary prostate cancer or a metastatic prostate cancer. In some examples, the prostate cancer is an early stage cancer, or a late stage cancer. In some examples, the prostate cancer is an aggressive cancer. In some examples, the prostate cancer is a low-, intermediate-, or high-risk prostate cancer. In some examples, the subject analyzed or treated with the disclosed methods has or will receive a prostatectomy.

The altered expression of CSPG5, FKBP6, FOSB, STMN1, and TTC27 can be any measurable increase or decrease in expression that is correlated with likely responsiveness to ADT. In some embodiments, the increase or decrease in expression (such as mRNA, cDNA, or protein expression) is at least 2.5%, at least 3%, at least 4%, at least 5%, at least 6%, at least 7%, at least 8%, at least 9%, at least 10%, at least 15%, 20%, at least 30%, at least 40%, at least 50%, at least 75%, at least 90%, at least 99%, at least 100%, at least 1.5 fold, at least 2-fold, at least 3-fold, at least 4-fold, at least 5-fold, at least 7-fold or at least 10-fold, such as about 1.5-fold, about 2-fold, about 2.5-fold, about 3-fold, about 4-fold, about 5-fold, about 7-fold or about 10-fold. The relative increase or decrease in expression level amongst CSPG5, FKBP6, FOSB, STMN1, and TTC27 can vary within a tumor and can also vary between tumor samples.

The altered DNA methylation of CSPG5, FKBP6, FOSB, STMN1, and TTC27 can be any measurable increase or decrease in DNA methylation that is correlated with likely responsiveness to ADT. In some embodiments, the increase or decrease in DNA methylation is at least 2.5%, at least 3%, at least 4%, at least 5%, at least 6%, at least 7%, at least 8%, at least 9%, at least 10%, at least 15%, at least 20%, at least 30%, at least 40%, at least 50%, at least 75%, at least 90%, at least 99%, at least 100%, at least 1.5 fold, at least 2-fold, at least 3-fold, at least 4-fold, at least 5-fold, at least 7-fold or at least 10-fold, such as about 1.5-fold, about 2-fold, about 2.5-fold, about 3-fold, about 4-fold, about 5-fold, about 7-fold or about 10-fold. The relative increase or decrease in DNA methylation level amongst CSPG5, FKBP6, FOSB, STMN1, and TTC27 can vary within a tumor and can also vary between tumor samples.

TABLE 1

Example gene expression and/or DNA methylation in subjects that will respond to ADT

| Gene | Percent increase or decrease in expression | Percent increase or decrease in DNA methylation |
| --- | --- | --- |
| CSPG5 | At least a 2.5% decrease, such as a decrease of at least 3%, at least 4%, at least 5%, such as a 5.05% decrease | At least a 2.5% increase, such as an increase of at least 5%, at least 8%, such as a 9% increase |

TABLE 1-continued

Example gene expression and/or DNA methylation in subjects that will respond to ADT

| Gene | Percent increase or decrease in expression | Percent increase or decrease in DNA methylation |
|---|---|---|
| FKBP6 | At least a 2.5% increase, such as an increase of at least 3%, at least 4%, such as a 4.07% increase | At least a 5% decrease, such as a decrease of at least 10%, at least 15%, at least 20%, such as a 26.48% decrease |
| FOSB | At least a 10% increase, such as an increase of at least 15%, at least 20%, at least 25%, such as a 29.9% increase | At least a 5% increase, such as an increase of at least 10%, at least 12%, such as a 12.78% increase |
| STMN1 | At least a 2.5% decrease, such as a decrease of at least 3%, at least 4%, at least 5%, at least 8%, such as a 8.01% decrease | At least a 5% increase, such as an increase of at least 12%, at least 14%, such as a 4.02% increase |
| TTC27 | At least a 2.5% decrease, such as a decrease of at least 3%, at least 4%, at least 5%, such as a 5.29% decrease | At least a 2.5% increase, such as an increase of at least 3%, at least 4%, at least 5%, such as a 5.6% increase |

The control can be any suitable control against which to compare expression of CSPG5, FKBP6, FOSB, STMN1, and TTC27 in a prostate cancer sample. In some embodiments, the control sample is a prostate cancer sample, or plurality of samples, from a subject(s) known to respond to ADT. In other examples, the control sample is a prostate cancer sample, or plurality of samples, from a subject(s) known to not respond to ADT (in which case the increase or decrease in expression and/or DNA methylation correlation to ADT is reversed, that is FKBP6 is over-methylated while TTC27, CSPG5, FOSB, and STMN1 are under-methylated in patients responsive to ADT compared to a prostate cancer samples from a subject(s) known to not respond to ADT, and TTC27, STMN1, and CSPG5 are over-expressed while FOSB and FKBP6 are under-expressed in patients responsive to ADT compared to a prostate cancer samples from a subject(s) known to not respond to ADT). In some embodiments, the control is a reference value. For example, the reference value can be derived from the average expression values obtained from a group of prostate cancer subjects known to respond (or not respond) to ADT.

In some examples, measurement of an increase or a decrease in CSPG5, FKBP6, FOSB, STMN1, and TTC27 expression or DNA methylation (such as in a prostate cancer sample) can a better predictor of response to ADT than genes (such as markers) that are commonly used to predict prostate cancer aggressiveness. For example, measurement of an increase or a decrease in CSPG5, FKBP6, FOSB, STMN1, and TTC27 expression or DNA methylation can a better predictor of response to ADT than an increase or a decrease in expression of androgen receptor (AR), erythroblast transformation-specific (ETS)-related gene (ERG), transmembrane protease serine 2 (TMPRSS2), forkhead box protein A1 (FOXA1), NK3 homeobox 1 (NKX3-1), and/or phosphatase and tensin homolog (PTEN). For example, measurement of an increase or a decrease in CSPG5, FKBP6, FOSB, STMN1, and TTC27 expression or DNA methylation (such as in a prostate cancer sample) can a predict response to ADT with statistical significance (for example, with a p value<0.05, such as a p value at least <0.05, 0.01, 0.009, 0.008, 0.007, 0.006, 0.005, 0.004, 0.003, 0.002, or 0.001, or about 0.01-0.05 or 0.001-0.01, or about 0.005, 0.004, 0.002, 0.03, or 0.45), wherein genes that are commonly used to predict prostate cancer aggressiveness cannot predict response to ADT with statistical significance (for example, with a p value≥0.05, such as a p value at least >0.05, 0.10, 0.20, 0.30, 0.40, 0.50, 0.60, 0.70, 0.80, or 0.90 or about 0.05-0.10, 0.05-0.20, 0.10-0.50, or 0.50-1, or about 0.14, 0.38, 0.40, 0.69, 0.88, or 0.96).

A. Detecting Expression or Methylation

As described herein, expression of the 5 TACE-associated genes (CSPG5, FKBP6, FOSB, STMN1, and TTC27) can be detected using any one of a number of methods. Expression of nucleic acid molecules (e.g., mRNA, cDNA) or protein is contemplated herein. In some examples, DNA methylation of CSPG5, FKBP6, FOSB, STMN1, and TTC27 is measured. In some examples, expression and/or DNA methylation is quantified.

1. Methods for Detecting mRNA

Gene expression can be evaluated by detecting mRNA encoding the gene of interest. Thus, the disclosed methods can include evaluating mRNA encoding CSPG5, FKBP6, FOSB, STMN1, and TTC2. In some examples, the mRNA is quantified.

RNA can be isolated from a sample of a prostate cancer from a subject, for example using commercially available kits, such as those from QIAGEN®. General methods for mRNA extraction are disclosed in, for example, including Ausubel et al., Current Protocols of Molecular Biology, John Wiley and Sons (1997). RNA can be extracted from paraffin embedded tissues (e.g., see Rupp and Locker, *Lab Invest.* 56:A67 (1987), and De Andres et al., *BioTechniques* 18:42044 (1995)). Total RNA from cells in culture (such as those obtained from a subject) can be isolated using QIAGIN® RNeasy mini-columns. Other commercially available RNA isolation kits include MASTERPURE®. Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using northern blotting or in situ hybridization (Parker & Barnes, *Methods in Molecular Biology* 106:247-283, 1999); RNAse protection assays (Hod, Biotechniques 13:852-4, 1992); and PCR-based methods, such as reverse transcription polymerase chain reaction (RT-PCR) (Weis et al., Trends in Genetics 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

In one example, RT-PCR can be used. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, tubulin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Held et al., *Genome Research* 6:986 994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems, 850 Lincoln Centre Drive, Foster City, Calif. 94404 under the trademark ABI PRISM® 7700.

The steps of a representative protocol for quantifying gene expression using fixed, paraffin-embedded tissues as the RNA source, including mRNA isolation, purification, primer extension and amplification are given in various publications (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tumor tissue samples or adjacent non-cancerous tissue. The RNA is then extracted, and protein and DNA are removed. Alternatively, RNA is located directly from a tumor sample or other tissue sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as mRNA encoding CSPG5, FKBP6, FOSB, STMN1, and TTC27. In some embodiments, expression of other genes is also detected. Primers that can be used to amplify CSPG5, FKBP6, FOSB, STMN1, and TTC27 are commercially available or can be designed and synthesized (e.g., based on SEQ ID NOS: 1-5). In some examples, the primers specifically hybridize to a promoter or promoter region of CSPG5, FKBP6, FOSB, STMN1, or TTC27.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some embodiments of this method, the expression of a "housekeeping" gene or "internal control" can also be evaluated. These terms include any constitutively or globally expressed gene whose presence enables an assessment of HCC-associated gene mRNA levels. Such an assessment includes a determination of the overall constitutive level of gene transcription and a control for variations in RNA recovery. Exemplary housekeeping genes include b-actin and tubulin.

In some examples, gene expression is identified or confirmed using a microarray technique. Thus, the expression profile can be measured in either fresh or paraffin-embedded tumor tissue, using microarray technology. In this method, CSPG5, FKBP6, FOSB, STMN1, and TTC27 nucleic acid sequences (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors, and optionally from corresponding noncancerous tissue and normal tissues or cell lines.

In a specific embodiment of the microarray technique, PCR amplified inserts of cDNA clones are applied to a substrate in a dense array. At least probes specific for CSPG5, FKBP6, FOSB, STMN1, and TTC27 (and in some examples one or more housekeeping genes) nucleotide sequences are applied to the substrate, and the array can consist essentially of, or consist of these sequences. The microarrayed nucleic acids are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for CSPG5, FKBP6, FOSB, STMN1, and TTC27. Microarray analysis can be performed by commercially available equipment, following manufacturer's protocols.

Serial analysis of gene expression (SAGE) allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., Science 270:484-7, 1995; and Velculescu et al., Cell 88:243-51, 1997, herein incorporated by reference).

In situ hybridization (ISH) is another method for detecting and comparing expression of CSPG5, FKBP6, FOSB, STMN1, and TTC27. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of CSPG5, FKBP6, FOSB, STMN1, and TTC27.

Sample cells or tissues can be treated to increase their permeability to allow a probe, such as a CSPG5, FKBP6, FOSB, STMN1, or TTC27 gene-specific probe, to enter the cells. The probe is added to the treated cells, allowed to hybridize at pertinent temperature, and excess probe is washed away. The probe can be labeled, for example with a radioactive, fluorescent or antigenic tag, so that the probe's location and quantity in the tissue can be determined, for example using autoradiography, fluorescence microscopy or immunoassay. Since CSPG5, FKBP6, FOSB, STMN1, and TTC27 re known, probes can be designed accordingly such that the probes specifically bind the gene of interest.

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples can be fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products can be achieved by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Gene expression can also be detected and quantitated using the nCounter® technology developed by NanoString (Seattle, Wash.; see, for example, U.S. Pat. Nos. 7,473,767; 7,919,237; and 9,371,563, which are herein incorporated by reference in their entirety). The nCounter® analysis system utilizes a digital color-coded barcode technology that is based on direct multiplexed measurement of gene expression. The technology uses molecular "barcodes" and single molecule imaging to detect and count hundreds of unique transcripts in a single reaction. Each color-coded barcode is attached to a single target-specific probe corresponding to a gene of interest (such as a TACE-response gene). Mixed together with controls, they form a multiplexed CodeSet.

Each color-coded barcode represents a single target molecule. Barcodes hybridize directly to target molecules and can be individually counted without the need for amplification. The method includes three steps: (1) hybridization; (2) purification and immobilization; and (3) counting. The technology employs two approximately 50 base probes per mRNA that hybridize in solution. The reporter probe carries the signal; the capture probe allows the complex to be immobilized for data collection. After hybridization, the excess probes are removed and the probe/target complexes are aligned and immobilized in the nCounter® cartridge. Sample cartridges are placed in the digital analyzer for data collection. Color codes on the surface of the cartridge are counted and tabulated for each target molecule. This method is described in, for example, U.S. Pat. No. 7,919,237; and U.S. Patent Application Publication Nos. 20100015607; 20100112710; 20130017971, which are herein incorporated by reference in their entirety. Information on this technology can also be found on the company's website (nanostring.com).

2. Arrays for Profiling Gene Expression

In particular embodiments, arrays (such as a solid support) are provided that can be used to evaluate gene expression, for example to determine if a patient with prostate cancer will respond to ADT. Such arrays can include a set of specific binding agents (such as nucleic acid probes and/or primers specific for CSPG5, FKBP6, FOSB, STMN1, and TTC27) provided herein. When describing an array that consists essentially of probes or primers specific for CSPG5, FKBP6, FOSB, STMN1, and TTC27, such an array includes probes or primers specific for these five genes, and can further include control probes or primers, such as 1-10 control probes or primers (for example to confirm the incubation conditions are sufficient). In some examples, the array may further comprise additional, such as 1, 2, 3, 4 or 5 additional probes for other genes. In some examples, the array includes 1-10 housekeeping-specific probes or primers. In one example, an array is a multi-well plate (e.g., 98 or 364 well plate).

In one example, the array includes, consists essentially of, or consists of probes or primers (such as an oligonucleotide or antibody) that can recognize CSPG5, FKBP6, FOSB, STMN1, and TTC27 (and in some examples also 1-10 housekeeping genes). The oligonucleotide probes or primers can further include one or more detectable labels, to permit detection of hybridization signals between the probe and target sequence (such as CSPG5, FKBP6, FOSB, STMN1, and TTC27).

a. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluoride, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In one example, the solid support surface is polypropylene. In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

b. Array Formats

A wide variety of array formats can be employed. One example includes a linear array of oligonucleotide bands, generally referred to in the art as a dipstick. Another suitable format includes a two-dimensional pattern of discrete cells (such as 4096 squares in a 64 by 64 array). Other array formats including, but not limited to slot (rectangular) and circular arrays are equally suitable for use. In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats can be included in a variety of different types of formats. A "format" includes any format to which probes, primers or antibodies can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides.

The arrays of can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are describe in Matson et al., Anal. Biochem. 217:306-10, 1994. In one example, the oligonucleotides are synthesized onto the support using chemical techniques for preparing oligonucleotides on solid supports (such as see PCT applications WO 85/01051 and WO 89/10977, or U.S. Pat. No. 5,554,501).

The oligonucleotides can be bound to the polypropylene support by either the 3' end of the oligonucleotide or by the 5' end of the oligonucleotide. In one example, the oligonucleotides are bound to the solid support by the 3' end. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

3. Methods for Detecting Protein Expression

In some examples, expression of CSPG5, FKBP6, FOSB, STMN1, and TTC27 proteins is analyzed. Suitable biological samples include samples containing protein obtained from a prostate cancer of a subject. An alteration in the amount of CSPG5, FKBP6, FOSB, STMN1, and TTC27 proteins in a tumor from the subject relative to a control, such as an increase or decrease in proteins expression, indicates whether the prostate cancer will respond to ADT, as described herein.

Antibodies specific for CSPG5, FKBP6, FOSB, STMN1, and TTC27 proteins can be used for protein detection and quantification, for example using an immunoassay method, such as those presented in Harlow and Lane (*Antibodies, A Laboratory Manual*, CSHL, New York, 1988).

Exemplary immunoassay formats include ELISA, Western blot, and RIA assays. Thus, CSPG5, FKBP6, FOSB, STMN1, and TTC27 protein levels in a prostate cancer sample can be evaluated using these methods. Immunohistochemical techniques can also be utilized protein detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

To quantify proteins, a biological sample of the subject that includes cellular proteins can be used. Quantification of CSPG5, FKBP6, FOSB, STMN1, and TTC27 proteins can be achieved by immunoassay methods. The amount CSPG5, FKBP6, FOSB, STMN1, and TTC27 protein can be assessed in a prostate cancer sample and optionally in prostate cancer samples from patients known to respond to ADT (or not respond). The amounts of CSPG5, FKBP6, FOSB, STMN1, and TTC27 protein in the tumor can be compared to levels of the protein found in prostate cancer samples from patients known to respond to ADT (or not respond) or other control (such as a standard value or reference value). A significant increase or decrease in the amount can be evaluated using statistical methods.

Quantitative spectroscopic approaches, such as SELDI, can be used to analyze CSPG5, FKBP6, FOSB, STMN1, and TTC27 expression in a sample (such as a prostate cancer sample). In one example, surface-enhanced laser desorption-ionization time-of-flight (SELDI-TOF) mass spectrometry is used to detect protein expression, for example by using the ProteinChip™ protein analysis system (Ciphergen Biosystems, Palo Alto, Calif.). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

The surface chemistry allows the bound analytes to be retained and unbound materials to be washed away. Subsequently, analytes bound to the surface (such as tumor-associated proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind CSPG5, FKBP6, FOSB, STMN1, and TTC27. In other examples, the chromatographic surface consists essentially of, or consists of, antibodies that specifically bind CSPG5, FKBP6, FOSB, STMN1, and TTC27. In some examples, the chromatographic surface includes antibodies that bind other molecules, such as housekeeping proteins (e.g., tubulin, b-actin).

In another example, antibodies are immobilized onto the surface using a bacterial Fc binding support. The chromatographic surface is incubated with a sample, such as a sample of a prostate tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

4. Method of Detecting DNA Methylation

DNA methylation can be determined for each of CSPG5, FKBP6, FOSB, STMN1, and TTC27 in a prostate cancer sample, and in some examples also a control sample (e.g., prostate cancer samples from patients known to respond to ADT (or not respond)). Exemplary methods of detecting DNA methylation in a sample include bisulfite sequencing or conversion, pyrosequencing, HPLC-UV, LC-MS/MS, ELISA-based methods, and array or bead hybridization. In one example, the VeraCode® Methylation technology from Illumina is used. For a review of such methods see Kurdyukov and Bullock (*Biology* 5:3, 2016). Thus, in some examples, prostate cancer samples (or DNA isolated from such samples) are contacted with bisulfite, and can also be subjected to amplification and sequencing.

B. Prostate Cancer Samples

The methods provided herein include detecting expression and/or DNA methylation of CSPG5, FKBP6, FOSB, STMN1, and TTC27 in prostate cancer samples. In some embodiments, the prostate cancer samples are obtained from subjects diagnosed with prostate cancer. A "sample" refers to part of a tissue that is either the entire tissue, or a diseased or healthy portion of the tissue. As described herein, prostate cancer samples can be compared to a control. In some embodiments, the control is a prostate cancer sample obtained from a subject or group of subjects known to have favorably responded to ADT (or not to have responded). In other embodiments, the control is a standard or reference value based on an average of historical values. In some examples, the reference values are an average expression or DNA methylation value for each of CSPG5, FKBP6, FOSB, STMN1, and TTC27 in a prostate cancer sample obtained from a subject or group of subjects known to have favorably responded to ADT (or not to have responded).

Tissue samples can be obtained from a subject, for example from prostate cancer patients who have undergone tumor resection (e.g., prostatectomy) as a form of treatment. In some embodiments, prostate cancer samples are obtained by biopsy. Biopsy samples can be fresh, frozen or fixed, such as formalin-fixed and paraffin embedded. Samples can be removed from a patient surgically, by extraction (for example by hypodermic or other types of needles), by microdissection, by laser capture, or by other means.

In some examples, proteins and/or nucleic acid molecules (e.g., DNA, RNA, mRNA, and cDNA) are isolated or purified from the prostate cancer sample, which are then analyzed using the disclosed methods. In some examples, the prostate cancer is use directly, or is concentrated, filtered, or diluted.

C. Treatment

Patients with a prostate cancer identified using the disclosed methods as likely to respond to ADT, can receive ADT treatment. Thus, the disclosed methods can include administration of ADT. In contrast, patients with a prostate cancer identified using the disclosed methods as likely to not respond to ADT, do not receive ADT treatment. Instead, such subjects can received a non-ADT therapy, such as radiation therapy and/or chemotherapy.

Treatment of prostate cancer can include reducing signs or symptoms associated with the presence of such a tumor (for example by reducing the size or volume of the tumor or a metastasis thereof). Such reduced growth can in some examples decrease or slow metastasis of the tumor, reduce the size or volume of the tumor, or combinations thereof, by at least 10%, at least 20%, at least 40%, at least 50%, at least 75%, or at least 90%. In some examples, the methods include measuring the size and/or volume of a tumor (such as before and after ADT). In some examples, the subject receives additional therapy, such as surgical resection of the tumor (such as a prostatectomy).

1. Drug-Based ADT

There are two methods of ADT based on drugs. One works preventing the pituitary gland from releasing luteinizing hormone (LH) (chemical castration) and the other one blocks the body's ability to use androgens (anti-androgen).

Chemical castration uses LHRH agonists and antagonists, which both lower the amount of testosterone made by the testicles. They work inhibiting the formation of LH in the pituitary gland. LHRH agonists produce a sudden increase on levels of testosterone followed by a huge falling, process called flare, whereas LHRH antagonists decrease directly the amount of testosterone. Exemplary LHRH agonists that can be administered include leuprolide, goserelin, triptorelin, and histrelin. Exemplary LHRH antagonists that can be administered include a CYP17 inhibitor (such as abiraterone) and degarelix. In some examples, LHRH agonists and antagonists are administered via injection, such as subcutaneously. In some examples, LHRH agonists and antagonists are administered as an implant under the skin. In some examples, LHRH agonist and antagonists are administered monthly, every other month, or yearly.

Anti-androgen therapies block the body's ability to use any androgens. Prostate cells contain androgen receptor (AR), that when stimulated by androgens like testosterone, promotes growth and maintains prostatic differentiation. Antiandrogens can enter cells and reduce or prevent the binding of testosterone to the receptors. Exemplary antiandrogens that can be administered include cyproterone acetate, flutamide, nilutamide, bicalutamide, and enzalutamide (which can be administered orally, such as in oral pill form). In one example, the antiandrogen therapy targets testosterone synthesis (e.g., abiraterone acetate and seviteronel). In one example, the antiandrogen therapy targets AR nuclear translocation (e.g., enzalutamide, apalutamide, and darolutamide). In one example, the antiandrogen therapy is a combined therapy (e.g., galeterone). In one example, the antiandrogen therapy uses ketoconzaole. In some examples, one or more antiandrogens are administered daily, for example orally.

In some examples, a subject is treated with both androgen deprivation (orchiectomy or an LHRH agonist or antagonist) in combination with an anti-androgen. In some examples, a subject is treated with androgen deprivation (orchiectomy or an LHRH agonist or antagonist) in combination with an anti-androgen drug and with a 5-alpha reductase inhibitor (e.g., finasteride or dutasteride).

2. Surgical ADT

In some examples, a subject analyzed using the disclosed five gene panel is found to have a prostate cancer likely to respond to ADT, receives orchiectomy. Alternatively, a subject analyzed using the disclosed five gene panel is found to have a prostate cancer not likely to respond to ADT, does not receive orchiectomy.

3. Radiation Therapy

In some examples, a subject analyzed using the disclosed five gene panel is found to have a prostate cancer likely to respond to ADT, but can also be administered radiation therapy as an adjunctive therapy. In some examples, a subject analyzed using the disclosed five gene panel is found to have a prostate cancer not likely to respond to ADT, and instead is administered radiation therapy (for example in combination with chemotherapy).

Radiation therapy can use ionizing radiation to kill prostate cancer cells. In some examples, subjects are treated using brachytherapy, for example, where small radioactive particles, such as iodine-125 or palladium-103, are directly injected into the tumor, providing localized X-rays at the site of the tumor. In additional examples, ultrasound, such as high-intensity focused ultrasound (HIFU) is used.

3. Chemotherapy

In some examples, a subject analyzed using the disclosed five gene panel is found to have a prostate cancer likely to respond to ADT, but can also be administered chemotherapy as an adjunctive therapy. In some examples, a subject analyzed using the disclosed five gene panel is found to have a prostate cancer not likely to respond to ADT, and instead is administered chemotherapy (for example in combination with radiation therapy).

In one example the therapy includes administration of one or more chemotherapy immunosuppressants (such as Rituximab, steroids) or cytokines (such as GM-CSF). Exemplary chemotherapeutic agents are disclosed in Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993. Exemplary chemotherapeutic agents that can be administered include but are not limited to, carboplatin, cisplatin, paclitaxel, docetaxel, doxorubicin, epirubicin, cabaziatxel, estramustine, vinblastine, topotecan, irinotecan, gemcitabine, iazofurine, etoposide, vinorelbine, tamoxifen, valspodar, cyclophosphamide, methotrexate, fluorouracil, mitoxantrone, and Doxil® (liposome encapsulated doxiorubicine). In one example the therapy includes docetaxel and prednisone. In one example the therapy includes cabaziatxel, mitoxantrone, or estramustine.

In one example, the chemotherapy includes administering one or more of a microtubule binding agent, DNA intercalator or cross-linker, DNA synthesis inhibitor, DNA and/or RNA transcription inhibitor, antibodies, enzymes, enzyme inhibitors, and gene regulators.

Microtubule binding agents interact with tubulin to stabilize or destabilize microtubule formation thereby inhibiting cell division. Examples of microtubule binding agents that can be used include, without limitation, paclitaxel, docetaxel, vinblastine, vindesine, vinorelbine (navelbine), the epothilones, colchicine, dolastatin 10, nocodazole, and rhizoxin. Analogs and derivatives of such compounds also can be used. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds can be used as chemotherapy: DNA and/or RNA transcription regulators, including, without limitation, anthracycline family members (for example, daunorubicin, doxorubicin, epirubicin, idarubicin, mitoxantrone, and valrubicin) and actinomycin D, as well as derivatives and analogs thereof. DNA intercalators and cross-linking agents that can be administered to a subject include, without limitation, platinum compounds (for example, carboplatin, cisplatin, oxaliplatin, and BBR3464), mitomycins, such as mitomycin C, bleomycin, chlorambucil, cyclophosphamide, as well as busulfan, dacarbazine, estramustine, and temozolomide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, exemestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone, and derivatives and analogs thereof. Kinase inhibitors include imatinib, gefitinib, and erolitinib that prevent phosphorylation and activation of growth factors.

In one example, the therapy includes folic acid (for example, methotrexate and pemetrexed), purine (for example, cladribine, clofarabine, and fludarabine), pyrimidine (for example, capecitabine), cytarabine, fluorouracil, gemcitabine, and derivatives and analogs thereof. In one example, the therapy includes a plant alkaloid, such as *Podophyllum* (for example, etoposide) and derivatives and analogs thereof. In one example, the therapy includes an antimetabolite, such as cytotoxic/antitumor antibiotics, bleomycin, hydroxyurea, mitomycin, and derivatives and analogs thereof. In one example, the therapy includes a topoisomerase inhibitor, such as a topoisomerase I inhibitor (e.g., topotecan, irinotecan, indotecan, indimitecan, camptothecin and lamellarin D) or a topoisomerase II inhibitor (e.g., etoposide, doxorubicin, daunorubicin, mitoxantrone, amsacrine, ellipticines, aurintricarboxylic acid, ICRF-193, genistein, and HU-331), and derivatives and analogs thereof. In one example, the therapy includes a photosensitizer, such as aminolevulinic acid, methyl aminolevulinate, porfimer sodium, verteporfin, and derivatives and analogs thereof. In one example, the therapy includes a nitrogen mustard (for example, chlorambucil, estramustine, cyclophosphamide, ifosfamide, and melphalan) or nitrosourea (for example, carmustine, lomustine, and streptozocin), and derivatives and analogs thereof.

Other therapeutic agents, for example anti-tumor agents, that may or may not fall under one or more of the classifications above, also are suitable for chemotherapy. By way of example, such agents include adriamycin, apigenin, rapamycin, zebularine, cimetidine, amsacrine, anagrelide, arsenic trioxide, axitinib, bexarotene, bevacizumab, bortezomib, celecoxib, estramustine, hydroxycarbamide, lapatinib, pazopanib, masoprocol, mitotane, tamoxifen, sorafenib, sunitinib, vandetanib, tretinoin, and derivatives and analogs thereof.

In one example, the chemotherapy includes one or more biologics, such as a therapeutic antibody, such as monoclonal antibodies. Examples of such biologics that can be used include one or more of bevacizumab, cetuximab, panitumumab, pertuzumab, trastuzumab, bevacizumab (Avastin®), ramucirumab, and the like. In specific examples, the antibody or small molecules used as part of the therapy include one or more of the monoclonal antibodies cetuximab, panitumumab, pertuzumab, trastuzumab, bevacizumab (Avastin® monoclonal antibodies), ramucirumab, or a small molecule inhibitor such as gefitinib, erlotinib, and lapatinib.

In some examples the chemotherapy includes administration of one or more immunotherapies, which may include the biologics listed herein. In specific examples, the immunotherapy includes therapeutic cancer vaccines, such as those that target PSA (e.g., ADXS31-142), pro static acid phosphatase (PAP) antigen, TARP, telomerase (e.g., GX301) or that deliver 5T4 (e.g., ChAdOx1 and MVA); antigens NY-ESO-1 and MUC1; antigens hTERT and survivin; prostate-specific antigen (PSA) and costimulatory molecules (e.g., LFA-3, ICAM-1, and B7.1) directly to cancer cells, such as rilimogene galvacirepvac. Other examples of therapeutic vaccines include DCVAC, sipuleucel-T, pTVG-HP DNA vaccine, pTVG-HP, JNJ-64041809, PF-06755992, PF-06755990, and pTVG-AR. In other examples, the immunotherapy includes oncolytic virus therapy, such as aglatimagene besadenovec, HSV-tk, and valacyclovir. In additional examples, the immunotherapy can include checkpoint inhibitors, such as those that target PD-1 (e.g., nivolumab, pembrolizumab, durvalumab, and atezolizumab), CTLA-4 (e.g., tremelimumab and ipilimumab), B7-H3 (e.g., MGA271), and CD27 (e.g., CDX-1127). The protein MGD009 may also be used in another example. In specific examples, the immunotherapy can also include adoptive cell therapy, such as those that include T cells engineered to target NY-ESO-1 and those that include natural killer (NK) cells. In some examples, the immunotherapy can include adjuvant immunotherapies, such as sipuleucel-T, indoximod, and mobilan. In other specific examples, the immunotherapy includes one or more of tisotumab vedotin, sacituzumab govitecan, LY3022855, BI 836845, vandortuzumab vedotin, and BAY2010112, and MOR209/ES414. In additional examples, the immunotherapy can include cytokines, such as CYT107, AM0010, and IL-12.

In some examples, the subject receiving chemotherapy is administered interleukin-2 (IL-2), as part of the therapy, for example via intravenous administration. In particular examples, IL-2 is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the subject receiving chemotherapy is administered a fully human antibody to cytotoxic T-lymphocyte antigen-4 (anti-CTLA-4) as part of the therapy, for example via intravenous administration. In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one specific example the chemotherapy can include one or more of abiraterone acetate, bicalutamide, cabazitaxel, casodex (bicalutamide), degarelix, docetaxel, enzalutamide, flutamide, goserelin acetate, jevtana (cabazitaxel), leuprolide acetate, lupron (leuprolide acetate), lupron depot (leuprolide acetate), lupron depot-3 month (leuprolide acetate), lupron depot-4 month (leuprolide acetate), lupron depot-ped (leuprolide acetate), mitoxantrone hydrochloride, nilandron (nilutamide), nilutamide, provenge (sipuleucel-t), radium 223 dichloride, sipuleucel-T, taxotere (docetaxel), viadur (leuprolide acetate), xofigo (radium 223 dichloride), xtandi (enzalutamide), zoladex (goserelin acetate), and zytiga (abiraterone acetate).

In another specific example the chemotherapy can include one or more of cabazataxel (Jevtana® therapy), docetaxel (Taxotere® therapy), mitoxantrone (Teva® therapy), or androgen deprivation therapy (ADT), such as with abiraterone Acetate (Zytiga® therapy), bicalutamide (Casodex® therapy), buserelin Acetate (Suprefact® therapy), cyproterone Acetate (Androcur® therapy), degarelix Acetate (Firmagon® therapy), enzalutamide (Xtandi® therapy), flutamide (Euflex® therapy), goserelin Acetate (Zoladex® therapy), histrelin Acetate (Vantas® therapy), leuprolide Acetate (Lupron® therapy, Eligard® therapy), triptorelin Pamoate (Trelstar® therapy). The therapy can also include drugs to treat bone metastases (bisphosphate therapy), such as alendronate (Fosamax® therapy), denosumab (Xgeva® therapy), pamidronate (Aredia® therapy), zoledronic acid (Zometa® therapy), or radiopharmaceuticals, such as radium 223 (Xofigo® therapy), strontium-89 (Metastron® therapy), and samarium-153 (Quadramet® therapy).

The therapy can be administered in cycles (such as 1 to 6 cycles), with a period of treatment (usually 1 to 3 days) followed by a rest period. But some therapies can be administered every day.

IV. Specific Binding Agents and Kits

Also provided are sets of specific binding agents, such as sets of nucleic acid probes, nucleic acid primers, and antibodies (or antibody fragments), such as a set that includes a nucleic acid probe specific for each of CSPG5, FKBP6, FOSB, STMN1, and TTC27, a nucleic acid primer specific for each of CSPG5, FKBP6, FOSB, STMN1, and TTC27, an antibody specific for each of CSPG5, FKBP6, FOSB, STMN1, and TTC27, or combinations thereof. Such probes, primers, and antibodies can be in vials, such as a glass or plastic container, or attached or conjugated to an array (e.g., solid substrate) as discussed above. In some examples, the primers, and antibodies are in a carrier, such as a buffer (e.g., saline). In some examples, such sets further include a nucleic acid probe, a nucleic acid primer, or antibody, specific for at least one housekeeping molecule, such as 1, 2, 3, 4, 5, 6, 7, 8, 9 or 10, or about 1 to about 3, or about 1 to about 5, housekeeping molecules (e.g., b-actin, tubulin).

Also provided are kits that include such sets of specific binding agents. Such kits can include other components, such as a buffer (e.g., hybridization buffer).

Also provided are methods of detecting expression or DNA methylation of CSPG5, FKBP6, FOSB, STMN1, and TTC27 in a prostate cancer sample using such kits and sets of binding agents.

Further provided herein are kits that include a probe set disclosed herein, such as a probe set that includes a nucleic acid probe specific for each of CSPG5, FKBP6, FOSB, STMN1, and TTC27. In some examples, the kit further includes a buffer, such as a hybridization buffer. In some examples, the kit further includes reagents for PCR, such as polymerase, dNTPs, reverse transcriptase, $MgCl_2$, or combinations thereof.

The following examples are provided to illustrate certain particular features and/or embodiments. These examples should not be construed to limit the disclosure to the particular features or embodiments described.

Example 1

Materials and Methods

This example describes the materials and methods used to obtain the results described in Examples 2-7 (also see Panja et al., EBioMedicine 31:110-21, 2018, herein incorporated by reference in its entirety).

DNA Methylation and mRNA Expression Resources

Prostate cancer patient cohorts utilized come from the publicly available data sources, including *The Cancer Genome Atlas—Prostate Adenocarcinoma* (*TCGA-PRAD*), *Stand up to Cancer* (*SU2C*), Grasso et al (GSE35988), Cai et al (GSE32269), Sboner et al (GSE16560), Beltran et al, and *Prostate Cancer Medically Optimized Genome-Enhanced Therapy* (*PROMOTE*) datasets: (i) TCGA-PRAD (Abeshouse et al., 2015) cohort was downloaded from Genomics Data Commons (GDC, gdc.nci.nih.gov) on Nov. 15, 2016. Information about type and time of treatment was obtained and synthesized from the clinical, follow-up, and the treatment data files, obtained from the TCGA GDC legacy archive (portal.gdc.cancer.gov). For the purpose of this study, patients with primary tumors (obtained after radical prostatectomy), which were treated with adjuvant androgen deprivation therapy (ADT) and further monitored for disease progression (n=66), which were suited to studying primary ADT resistance, were selected. TCGA-PRAD DNA methylation was profiled on Illumina Infinium Human Methylation (HM450) array and RNA-seq was profiled on Illumina HiSeq 2000; (ii) *Stand up to Cancer* (*SU2C*) (Robinson et al., 2015) contained tumors from metastatic castration-resistant prostate cancer (CRPC, n=51, raw sequencing data for 51 patients were available for download from dbGaP phs000915.v1.p1) obtained from bone or soft tissue biopsies, profiled on Illumina HiSeq 2500 platform; (iii) Grasso et al (Grasso et al., 2012) dataset was obtained from Gene Expression Omnibus (GEO) GSE35988 and contained prostatectomy samples of primary tumors from patients with hormone-naïve prostate cancer (n=58) and metastatic CRPC samples at rapid autopsy (n=33), profiled on Agilent-014850 Whole Human Genome Microarray 4×44K G4112F; (iv) Cai et al (Cai et al., 2013) dataset was obtained from GEO GSE32269 and contained primary tumors from patients with hormone-naïve prostate cancer isolated by laser capture microdissection (LCM) from frozen biopsies (n=21) and CRPC bone metastasis obtained through CT guided bone marrow biopsies (n=19), profiled on Affymetrix Human Genome U133A array; (v) Beltran et al (Beltran et al., 2011): data were downloaded from dbGaP (phs000909.v1.p1) and contained tumors from metastatic castration-resistant prostate cancer (CRPC, neuroendocrine samples excluded, n=34) obtained from lung, soft tissue and spinal cord biopsies, profiled on Illumina Genome Analyzer II; (vi) Prostate Cancer Medically Optimized Genome-Enhanced Therapy (PROMOTE) (Kohli et al., 2015): data were downloaded from dbGaP (phs001141.v1.p1) and contained tumors from metastatic CRPC that received 12 weeks of Abiraterone acetate and failed this treatment (n=29), obtained from tissue biopsies and profiled on Illumina HiSeq 2500 platform; and as a negative control, we utilized (vii) Sboner et al (Sboner et al., 2010) dataset obtained from GEO GSE16560, which consisted of not treated primary tumors obtained from transurethral resection of the prostate (TURP) (n=281) and profiled on 6 k cDNA-mediated annealing, selection, ligation, and extension (DASL) microarray platform.

DNA Methylation and mRNA Expression Data Analysis and Integration

This study provides a framework (FIG. 1) to effectively integrate DNA methylation with mRNA expression patient profiles to identify markers of primary treatment resistance. DNA methylation profiles on Illumina Infinium Human Methylation depict methylation levels of CpG sites, located across TSS 200/1500 (TSS 1500 and TSS 200), 5' UTR, $1^{st}$ exon, gene body, and 3' UTR regions and are reported as β (Beta) values. β values were converted to M-values (better suited for statistical analysis; Du et al., 2010), where $$M = \log_2 \frac{\text{Beta}}{1 - \text{Beta}}.$$

All statistical computing was performed using R studio version 1.0.143 (R version 3.4.3). Differential methylation signature was defined as a list of methylation sites ranked by their differential methylation between patients with poor and favorable ADT response, using two-tail two-sample Student t-test (t.test function in R). DESeq2 R package (Love et al., 2014) was used for RNAseq data normalization and processing.

The initial step in the analysis was to evaluate if sites from a particular region (i.e., TSS 200/1500, 5' UTR, $1^{st}$ exon, gene body, 3' UTR) were enriched in the differential methylation signature. The Fisher Exact Test (FET) (Fisher, 1922) and Gene Set Enrichment Analysis (GSEA) (Subramanian et al., 2005) were used. For FET, the 500 top most differentially methylated sites were used to evaluate if a specific region is over-represented in the top 500 sites compared to the rest of the signature and was conducted using fisher.test function in R. In GSEA, differential methylation signature was used as a reference and sites associated to specific regions were utilized as query sets. Normalized Enrichment Score (NES) and p-value for significance were estimated using 1,000 site permutations. GSEA was implemented in R studio, v 3.3.2.

To identify differentially methylated sites that have functional effect on the site-harboring genes, their association was measured through Pearson correlation (Mukaka, 2012) (also confirmed with Spearman correlation (Mukaka, 2012)), estimated between differentially methylated sites (M-values) and their site-harboring genes (DESeq2 normalized counts), using cor.test function in R. To further evaluate a potential cause-effect relationship, the linear least squares regression analysis (Chatterjee and Hadi, 2006) was employed, where each methylation M-value was considered as predictor (i.e., independent) variable and an mRNA expression value of the site-harboring gene was considered as response (i.e., dependent) variable, estimated using lm function in R. This analysis identified a panel of five site-gene pairs, which are differentially methylated between patients with poor and favorable treatment response and can explain expression variation in their site-harboring genes, which increases the probability of identifying (epi) genomic markers with functional role in therapeutic resistance.

Evaluation of Clinical Significance

To evaluate ability of the identified five site-gene panel to predict therapeutic response in independent datasets, prostate cancer patient cohorts were subjected to t-distributed stochastic neighbor embedding clustering (t-SNE), a dimensionality reduction technique well suited for visualization of high-dimensional datasets as a two (or three) dimensional space (Maaten and Hinton, 2008). In particular, t-SNE considers all pairs of high-dimensional (i.e., 5-dimensional in our case) points and converts their high-dimensional similarity into conditional probabilities in such a way that similar points (i.e., patient profiles) are assigned a high conditional probability, and dissimilar points are assigned a low conditional probability (i.e., defining Probability Distribution H in a high-dimensional space). Further, t-SNE defines Probability Distribution L over the same pairs of points (i.e., patient profiles) in the low-dimensional (i.e., 2-dimensional) space, and it aims to minimize the Kullback-Leibler divergence (Hershey and Olsen, 2007) between the Probability Distribution H and Probability Distribution L with respect to the locations of the points (i.e., patient profiles) in the space. Therefore, patients with similar five site-gene patterns will be projected as nearby points and patients with dissimilar five-site gene patterns will be projected as distant points in the two-dimensional space. Differences in therapeutic response in the identified patient groups were evaluated through Kaplan-Meier treatment-related survival analysis (Goel et al., 2010) and Cox proportional hazard model (Bender et al., 2005) using survival and survminer packages in R (Kassambara et al., 2017, Therneau, 2015). Log-rank and Wald tests were used to estimate statistical significance of the Kaplan-Meier survival analysis and Cox proportional hazard model, respectively, using R coxph function from survival package (Therneau and Grambsch, 2010).

To compare the ability of the DNA methylation and mRNA expression of the five site-gene panel to effectively classify patient groups, receiver operating characteristics (ROC) analysis (Hajian-Tilaki, 2013) were utilized on multiple (i.e., multivariable) logistic regression model, where identified patient groups were used as a response variable and M-value/RNA-seq distributions of five site-gene panel were used as inputs. ROC curves were evaluated using area under the curve (AUROC) (Hanley and McNeil, 1982), with AUROC=0.5 being a random classifier. The logistic regression analysis was implemented using glm (Zeileis et al., 2008) function and ROC analysis using roc function from pROC package in R (Robin et al., 2011).

To evaluate if expression of the five site-gene panel in primary tumors was comparable to CRPC metastasis and to demonstrate that molecular profiles of patients that received ADT and developed Biochemical Recurrence are similar to patients that failed ADT with metastatic disease, TCGA-PRAD and SU2C datasets were compared, by combining their raw RNAseq counts with subsequent normalization using DESeq2 R package (Love et al., 2014). To compare expression levels of the five site-gene panel across these datasets, each gene was scaled (i.e., each gene was z-scored with respect to the mean expression of this gene across the combined TCGA-SU2C datasets) and defined a composite expression z-score for the five site-gene panel for each patient. In particular, to define the composite expression z-score for each patient, z-scores of the 5 genes from the 5 site-gene panel were combined using Stouffer integration (Stouffer et al., 1949) (stouffer function from vulcan package in R (Alvarez et al., 2016)). Distributions for such composite z-scores were then compared between TCGA-PRAD and SU2C patient cohorts using one-tail two-sample Welch t-test.

Finally, to confirm ability of the disclosed five site-gene panel to identify and distinguish samples with CRPC ADT failure, independent patient cohorts for (i) t-SNE clustering; and (ii) multiple (i.e., multivariable) logistic regression were utilized followed by ROC analysis. In particular, to demonstrate that the five site-gene panel allows the effective identification of the CRPC ADT failure samples, patient cohorts in Grasso et al (Grasso et al., 2012) and Cai et al (Cai et al., 2013) were subjected to t-SNE clustering (Maaten and Hinton, 2008), with all five dimensions considered. Furthermore, to show the ability of the five-site-gene panel to effectively distinguish between CRPC ADT failure samples and TCGA-PRAD samples with favorable response (i.e., group 1), similarly to SU2C cohort, raw counts for patients cohorts in Beltran et al (Beltran et al., 2011) and PROMOTE (Kohli et al., 2015) were combined with the TCGA-PRAD cohort and subjected them to multiple logistic regression (where samples with CRPC ADT failure and samples with favorable ADT response were used as a response variable and gene expression distributions of 5 site-gene panel were used as inputs) followed by ROC analysis.

Multimodal Performance Evaluation

For multimodal performance assessment of the model, (i) advantages of the model over other commonly used methods, such as expression, methylation, and correlation data alone; (ii) non-randomness of its predictive ability through comparison to 5 site-gene pairs selected at random; (iii) robustness of the findings through evaluation of how well the model can classify patients at varying levels of noise was evaluated; and demonstrated that (iv) predictive ability of the panel is not affected by the commonly used prognostic clinical variables, such as pathological and clinical T-stage, Gleason score, age, and therapy subtypes.

Comparative analysis to expression, methylation, and correlation data alone was done using Kaplan-Meier survival analysis, hazard ratio, and concordance index (i.e., c-index), which measures how well our model can predict therapeutic response (with 1.0 being the highest predictive ability, equivalent to AUROC=1 or 100%). C-index was estimated using concordance.index function from survcomp package in R (Schroder et al., 2011).

To evaluate non-randomness of the predictions, a random model built through selection of 5 site-gene pairs at random 10,000 times was utilized. Nominal p-value for the model was estimated as the number of times Kaplan-Meier log-rank p-values for random 5 site-gene pairs reached or outperformed log-rank p-value for the original 5 site-gene panel.

To evaluate the robustness of the model, its predictive ability was tested with the increase of False Negative (FN) and False Positive (FP) rates. Let us define an iteration i=1 . . . 58. For False Negative estimation, at each iteration i, exactly i patients were selected at random and removed from the validation cohort using sample function from R. Each iteration i was repeated 10,000 times (except when i=1 and 2: for i=1, it was run 58 times as total number of ways 1 patient can be chosen from 58 patients is 58; for i=2, it was run 1,000 times as the total number of ways 2 patients can be chosen from 58 patients is ((58 choose 2)=1,653). For False Positive estimation, at each iteration i, exactly i patients were added to the validation cohort: random patients were generated as follows: (1) probability of an event was generated at random based on the actual data from the original un-altered validation set; (2) patient group was chosen at random, based on the probability of choosing a patient from the original un-altered validation set; (3) time to event or follow-up were chosen through random number generator using sample function in R. As FN and FP rates were increased, the newly formed noise-enriched patient set was clustered and subjected it to Kaplan-Meier survival analysis, reporting the median log-rank p-values for each i, sampled from 10,000 iterations.

To confirm that fluctuations in the signature threshold levels do not affect predictive power of the model, performance of the model was evaluated while varying (i) methylation signature threshold (originally p<0.001) between 0.0001 and 0.005; and (ii) correlation threshold (originally p<0.05) between 0.02 and 0.05. For each threshold point, multiple logistic regression was used, where TCGA-PRAD patient groups with poor and favorable treatment response were used as a response variable and M-values of site harboring genes below the corresponding threshold were used as inputs, followed by ROC analysis.

Finally, to assess if the predictive ability of the five site-gene panel is independent of commonly used prognostic variables such as pathological and clinical T-stage, Gleason score, patient age and therapy subtypes, we performed univariable and multivariable Cox proportional hazard model analysis using coxph function from survival package in R (Therneau and Grambsch, 2010).

Example 2

Overview

To identify molecular mechanisms that differentiate favorable and poor ADT treatment response in prostate cancer, DNA methylation profiles of patients that failed ADT (i.e., non-responders) were compared with profiles of patients with favorable response to ADT (i.e., responders) (see schematics FIG. 1), which defined a therapeutic failure signature. Region-based analysis of methylation sites identified TSS 1500, TSS 200, 5' UTR, and $1^{st}$ exon regions with significant contribution (i.e., enrichment) in the therapeutic failure signature. We followed this discovery with the integrative analysis of DNA methylation and gene expression profiles, which identified methylation sites that are significantly associated (i.e., through Pearson correlation) and can explain expression variation (i.e., through linear regression analysis) of their site-harboring genes. Identified candidates were then subjected to validation (i.e., their ability to predict treatment response) in independent non-overlapping clinical patient cohorts, using Kaplan-Meier survival analysis (Goel et al., 2010) (log-rank p=0.0191, hazard ratio=4.37), t-distributed stochastic neighbor embedding clustering (Maaten and Hinton, 2008) (sensitivity=100%), and ROC analysis (Hajian-Tilaki, 2013) (AUROC=0.83, AUROC=0.98). Performance of the disclosed model was compared to methylation, expression, and correlation alone and demonstrated that this model outperforms these data types in correctly classifying patients at risk of ADT resistance. Furthermore, the statistical significance of these predictions were evaluate through random modeling (random model 1 p=0.010, random model 2 p=0.011) and robustness analysis (FN threshold=31%, 18/58; FP threshold=9%, 5/58) to demonstrate non-random robust classification of patients into ADT response groups. Finally, to demonstrate that the model is not affected by commonly used prognostic clinical variables, such as pathological and clinical T-stage, Gleason score, age, and therapy subtypes, multivariable Cox proportional hazard model (Bender et al., 2005) was utilized, demonstrating that none of these variables were predictive of ADT response and they did not affect predictive ability of the five site-gene panel.

Example 3

Time-Course Analysis of Treatment Response Identifies Signature of Therapeutic Failure To evaluate treatment response to ADT in prostate cancer patients, HumanMethylation450 (Morris and Beck, 2015) DNA methylation profiles of primary prostate tumors from The Cancer Genome Atlas (TCGA-PRAD) (Abeshouse et al., 2015) patient cohort were analyzed. While relatively recent, TCGA-PRAD represents the most comprehensive cohort of ADT treatment administration with clinical follow-up to date. Samples in TCGA-PRAD study represent localized prostate cancer samples that had been obtained through radical prostatectomy from patients that did not receive any neo-adjuvant (i.e., prior to prostatectomy) treatment. Following prostatectomy, patients were monitored for adjuvant (i.e., post-operative) ADT administration and disease progression, such as Biochemical Recurrence (BCR, defined by a rapid rise of prostate-specific antigen, PSA, in patient blood), local or distant metastases, and prostate cancer-related lethality (i.e., death due to prostate cancer). This study focused on patients that received adjuvant ADT and had available follow-up clinical data (n=66), suited to study primary ADT resistance.

Figure 2C:
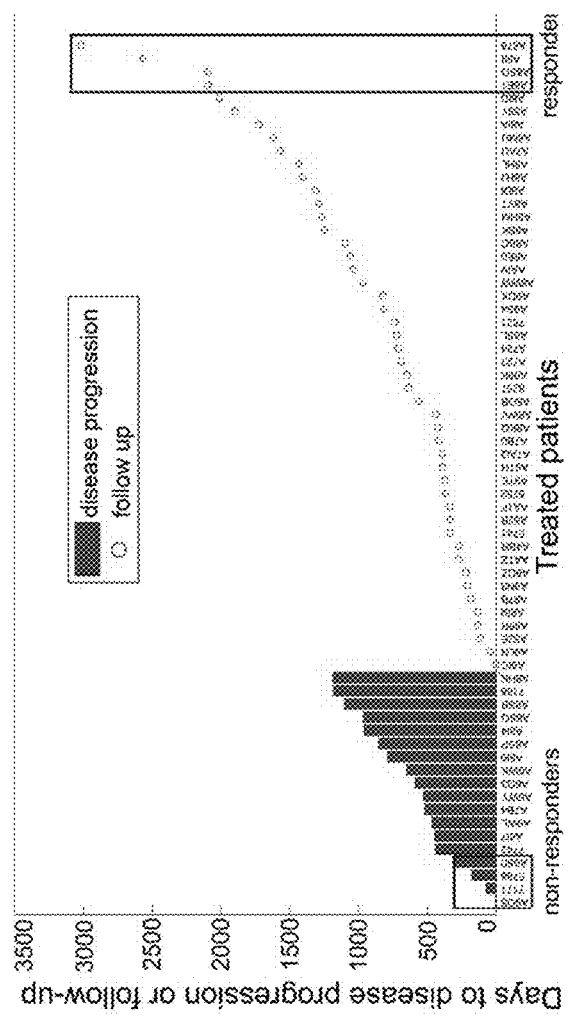
FIGS. 2A-2C. Analysis of therapeutic response defines signature of ADT resistance.
Figure 2A:
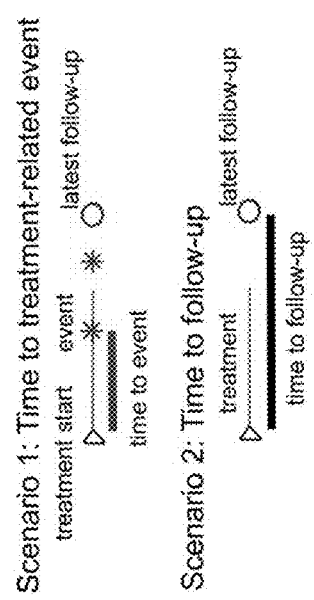
Figure 2B:
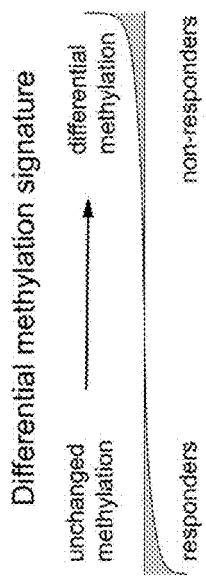

Each patient was evaluated with respect to the start of his androgen-deprivation regimen and time to disease progression (BCR, local or distant metastasis, or lethality) or time to follow-up (if no event occurred, such patients were considered censored). If a patient had an event during the course of the treatment or within 1.5 years after the end of the treatment (FIG. 2a, Scenario 1), time to treatment failure was defined as time between the treatment start and such an event (FIG. 2B, red bars). At the same time, if a patient did not experience a treatment-related event, time for his treatment-related disease-free survival was estimated as time between the treatment start and time to his latest follow-up (FIG. 2A, Scenario 2, FIG. 2B, blue circles).

To define epigenomic changes that differentiate therapeutic failure and success, DNA methylation profiles of patients with most rapid treatment failure were compared to patients with longest treatment-related disease-free survival. For this, we ranked patients based on their treatment-related disease-free survival time (FIG. 2B) and compared those that fall into the most left and right distribution tails (roughly, patients outside of a 90% confidence interval), which defined (i) non-responders as patients that experienced treatment failure within 1 year of treatment (n=4) and (ii) responders as patients with treatment-related disease-free survival over 5.5 years (n=4) (FIG. 2B).

Figure 3:
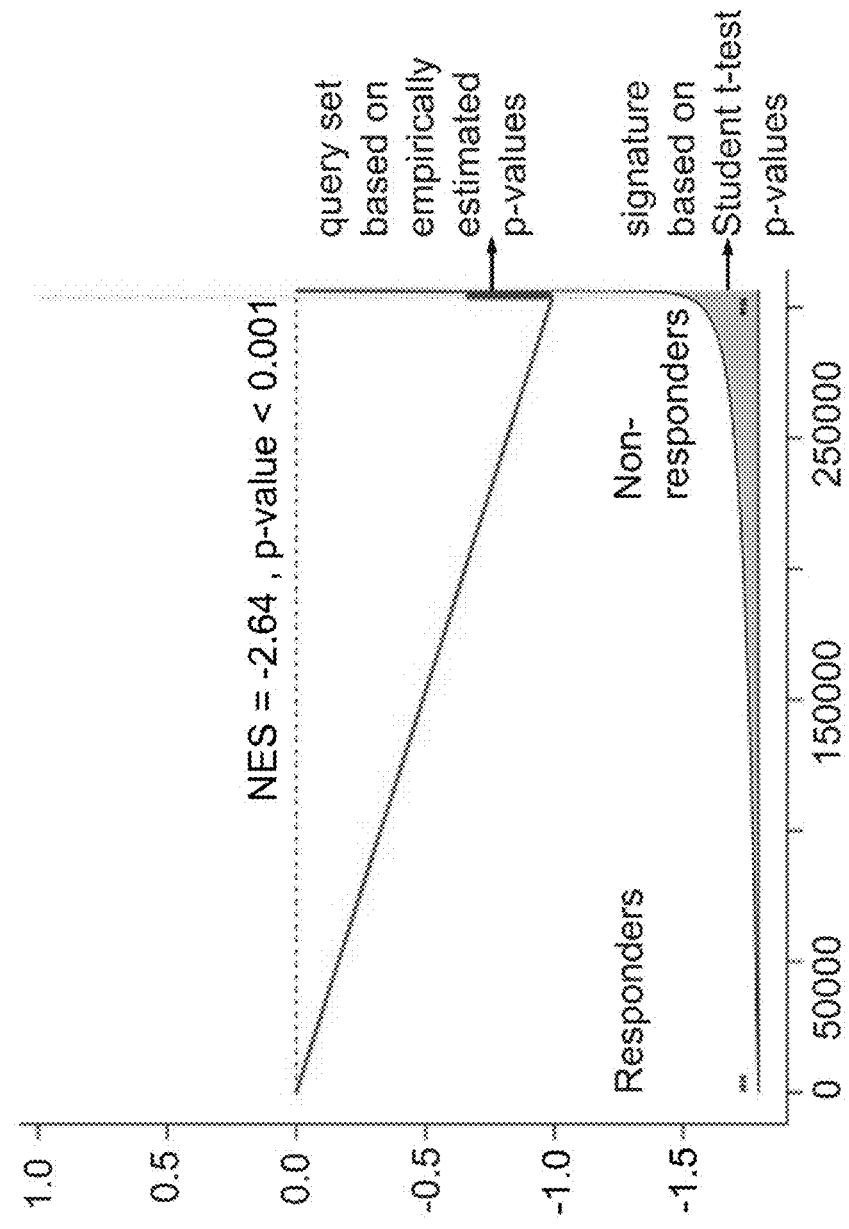
FIG. 3: GSEA comparison of parametric and non-parametric differential methylation signatures. GSEA comparing a parametric ADT resistance differential methylation signature, based on two-sample two-tail Student t-test p-values (used as a reference signature), and a non-parametric ADT resistance differential methylation signature, based on empirically estimated p-values (from 10,000 site permutations, sites with p<0.001, used as a query gene set).
Figures 4A, 4B, 4C:
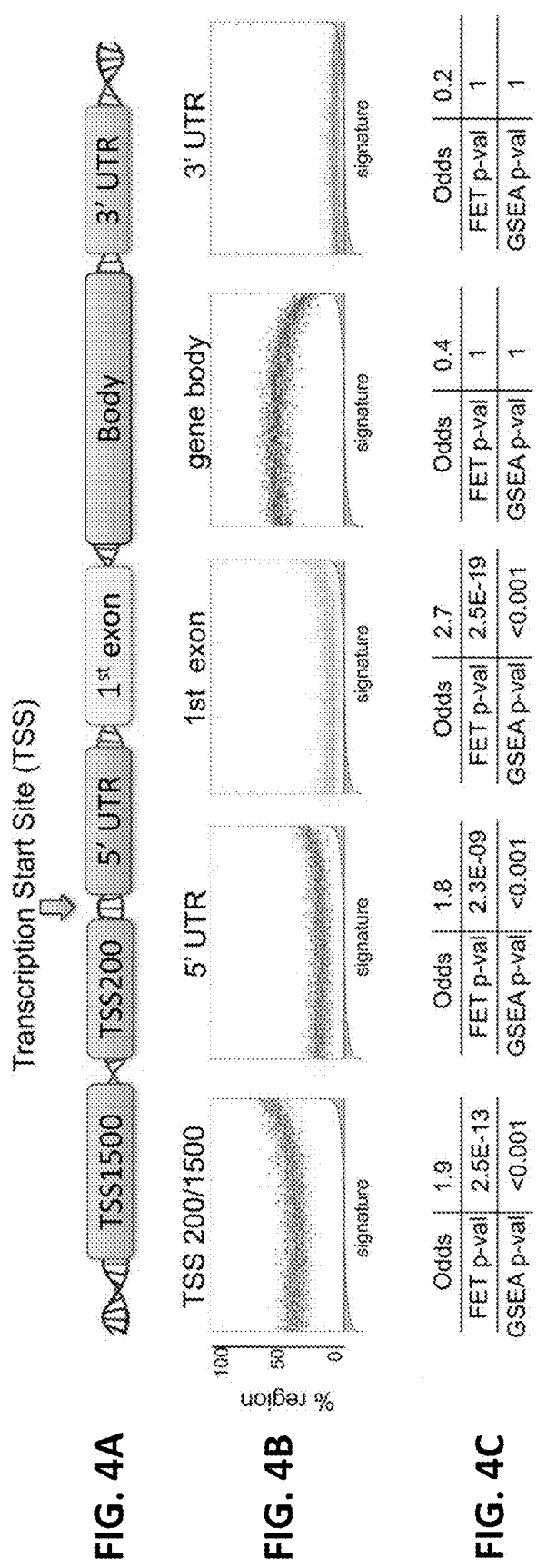
FIGS. 4A-4C. Methylation sites from TSS 200/1500, 5'UTR, and $1^{st}$ exon regions are enriched in methylation signature of ADT resistance.

Age, Gleason score, and tumor aggressiveness at diagnosis (which includes pathological and clinical T-stage) were compared between the two groups (Table 2) and no significant difference in clinical aggressiveness was observed in non-responder compared to responder groups (average age in non-responders group=60.5 and in responders group=60.0; average Gleason score in non-responders group was 8.25 and in responders group=9.0). M-value transformed DNA methylation profiles of non-responders and responders was compared using two-sample two-tail t-test, followed by ranking of the methylation sites based on the t-test p-values, from the least differentially methylated (FIG. 2C, left tail) to the most differentially methylated (FIG. 2C, right tail), which defined a "differential methylation signature" of ADT resistance (i.e., treatment failure). This analysis was paralleled with a non-parametric signature reconstruction, where an empirical p-value for each site was estimated after 10,000 random site permutations (followed by an FDR correction) and obtained virtually identical results (NES=−2.64, p<0.001), confirming robustness of the signature reconstruction (FIG. 3).

tially methylated part of the signature (i.e., right tail), as is evident from analysis for TSS 200/1500, 5' UTR, and $1^{st}$ exon regions (FIG. 3B). The statistical significance of such enrichments was evaluated using Fisher Exact Test (FET) (Fisher, 1922) and Gene Set Enrichment Analysis (GSEA) (Subramanian et al., 2005) (see Materials and Methods), which confirmed statistical significance of enrichment for TSS 200/1500 (FET p=2.5E-13, GSEA p<0.001), 5'UTR (FET p=2.3E-09, GSEA p<0.001), and 1st exon (FET p=2.5E-19, GSEA p<0.001) regions in the differential methylation signature, while body and 3' UTR regions did not show any enrichment (FIG. 4C). Given these results, TSS 200/1500, 5' UTR and $1^{st}$ exon regions were considered for the subsequent therapeutic failure analysis.

TABLE 2

Clinical characteristics of non-responders (n = 4) and responders (n = 4).

| Category | Patient ID | Gleason score | Pathological T-stage | Clinical T-stage | Age | Time to treatment-related event or follow-up (days) | Observed treatment-related event or follow-up |
|---|---|---|---|---|---|---|---|
| Non-responders | A9S0 | 8 | T3b | T2a | 53 | 314 | BCR |
| | 5788 | 7 | T3b | NA | 69 | 177 | BCR |
| | 7171 | 9 | T3b | T3a | 56 | 72 | BCR |
| | A9O5 | 9 | T4 | T2b | 64 | 6 | BCR |
| Responders | A6E1 | 9 | T3b | T2c | 57 | 2,091 | Latest follow-up |
| | A8SO | 9 | T3a | T1a | 64 | 2,092 | Latest follow-up |
| | A8II | 9 | T3a | T2c | 61 | 2,563 | Latest follow-up |
| | A878 | 9 | T2c | T1c | 58 | 3,015 | Latest follow-up |

BCR = Bio Chemical Recurrence

Example 4

TSS 200/1500, 5' UTR, and 1st Exon Regions are Enriched in Treatment Resistance Signature Following reconstruction of the differential methylation signature, the contribution of each region (profiled on HumanMethylation450 array, FIG. 4A) to resistance to ADT was evaluated. Regions profiled on the HumanMethylation450 include TSS 200 (i.e., −200 base pairs upstream of the Transcription Start Site, TSS) or TSS 1500 (i.e., between −200 and −1500 base pairs upstream of the TSS), 5'UTR (5' untranslated region), $1^{st}$ exon, gene body, and 3'UTR (3' untranslated region) (FIG. 4A). Not to overlook proximal and distal regulatory elements, TSS 200 and TSS 1500 were considered together for subsequent analysis (i.e., referred to as TSS 200/1500). A single site can be associated to several regions due to possible multiple splice variants of a site-bearing gene.

To evaluate contribution of each region, its enrichment in the differential methylation signature was determined. To visualize enrichment of each region, the differential methylation signature was divided into 100 site-long steps. Each step was evaluated with respect to the percentage (i.e., fraction) of sites that fall into TSS 200/1500, 5'UTR, 1st exon, body, or 3'UTR regions (FIG. 4B). Right-side upward-pointing "horn" indicates over-representation (i.e., enrichment) of sites from a specific region in the most differen- Example 5

Integrative (Epi) Genomic Analysis Identifies a 5 Site-Gene Panel of ADT Resistance To elucidate markers of ADT resistance, the differentially methylated sites were characterized and used to identify those that have a significant association and explain variation in the expression of the site-harboring genes (general strategy in FIG. 5A). For this, sites from TSS 200/1500, 5' UTR, and $1^{st}$ exon regions with significant differential methylation (t-test p<0.001, n=144, Dataset S1) between non-responders and responders (FIG. 5B) were focused on. The goal was to identify a "cause-effect" relationship, where differentially methylated sites (n=144) would have a potential functional "causal" effect on the expression changes in the site-harboring genes. As a pre-screen for such relationship, Pearson correlation analysis (Mukaka, 2012) between methylation M-values for each site and mRNA expression levels (i.e., DESeq2 (Love et al., 2014) normalized counts) for each corresponding site-harboring gene were utilized. Such analysis was done for each site-gene pair and identified differentially methylated sites with significant positive (or negative) association to their corresponding genes (i.e., Pearson correlation p<0.05, n=8) (FIG. 5C).

The next step was to test these site-gene pairs to determine the extent to which methylation values can explain variation in the expression changes of their site-harboring genes. For this, linear least squares regression analysis (Chatterjee and Hadi, 2006) was utilized, where a methylation M-value was considered as predictor (i.e., independent) variable and an mRNA expression value was considered as response (i.e., dependent) variable. Linear regression analysis identified a panel of 5 site-gene pairs (FIG. 5D), where differentially methylated sites could explain from 51% to 80% variation (i.e., as defined by the coefficient of determination, $R^2$) of the site-harboring genes: TTC27 ($R^2$=0.80, p=0.002), STMN1 ($R^2$=0.76, p=0.004), FOSB ($R^2$=0.75, p=0.005), FKBP6 ($R^2$=0.56, p=0.03), and CSPG5 ($R^2$=0.51, p=0.045). Interestingly, the differentially methylated site harbored by FOSB showed a positive relationship (i.e., positive slope) with FOSB mRNA expression while sites harbored by FKBP6, TTC27, CSPG5 and STMN1 showed a negative relationship (i.e., negative slope) (FIG. 5D), which indicates that changes in methylation levels might interfere with transcriptional regulation by a repressor or an activator, respectively.

Example 6

Validation in Independent Patient Cohorts

The ability of the five site-gene panel to predict therapeutic response to ADT in independent non-overlapping patient cohorts was examined. The validation sets were chosen to demonstrate (i) the 5 site-gene panel is capable of distinguishing between primary tumors with poor and favorable treatment response; (ii) molecular profiles of patients that were administered ADT and developed Biochemical Recurrence are similar to profiles of patients that genuinely failed the ADT with metastases and developed CRPC; (iii) the 5 site-gene panel can effectively identify CRPC samples; and (iv) the 5 site-gene panel can accurately distinguish between the primary prostate cancer samples with favorable treatment response and CRPC samples that failed ADT treatment.

A TCGA-PRAD cohort (n=58, TCGA-PRAD validation set) of ADT treated patients, excluding non-responders (n=4) and responders (n=4) was used to avoid over-fitting. T-distributed stochastic neighbor embedding clustering (t-SNE), a widely-used dimensionality reduction technique (Maaten and Hinton, 2008), done on the methylation levels of the identified 5 site-gene panel, classified patients from the validation set into two groups (i.e., group 1 and group 2) (see STAR Methods, FIG. 6A).

The next step in the predictive analysis was to evaluate if these patient groups significantly differed in their response to androgen-deprivation treatment. For this, treatment-related disease-free survivals (as defined previously, FIGS. 2A-2B) were compared between the groups using Kaplan-Meier survival analysis (Goel et al., 2010), which demonstrated significant difference in treatment response between the groups (see STAR Methods, FIG. 6B) (log-rank p=0.0191). Patients in groups 1 (aquamarine) experienced treatment-related disease progression events at a slower rate, while events related to androgen-deprivation therapy in group 2 (coral) occurred at a much faster rate (hazard ratio=4.37, p=0.031).

Whether patient separation was effected by Gleason score, a commonly used clinical prognostic variable, was determined. Patients with Gleason score 7 and Gleason score 8+9 were analyzed separately and it was observed that they did not affect treatment differences between the group 1 and group 2 (FIG. 7A, Gleason score 7 log-rank p=0.048; Gleason score 8+9 log-rank p=0.017) patient classification.

Given potential cause-effect relationship in the 5 site-gene panel, the effect of the expression of site-harboring genes on the separation between the two groups was further confirmed through Receiver Operating Characteristic (ROC) analysis (Hajian-Tilaki, 2013), whose performance was evaluated using area under the ROC, AUROC (Hanley and McNeil, 1982) (see STAR Methods, FIG. 6C), where AUROC=0.5 indicates a random classifier and AUROC=1 indicates a complete separation of the patient groups. ROC analysis demonstrated that both methylation levels of five sites (AUROC=0.98) as well as expression levels of site-harboring genes (AUROC=0.74) significantly contributed to the group separation and thus can be utilized for patient classification.

Figure 7B:
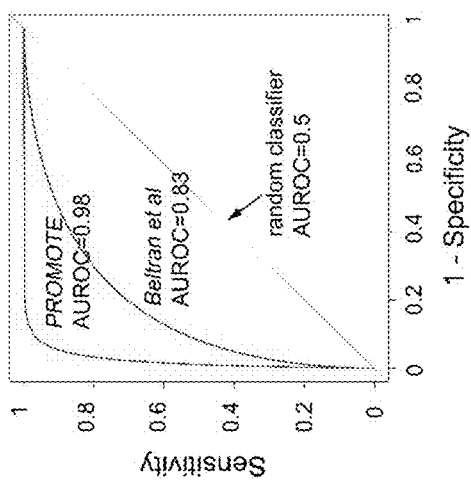
FIGS. 7A-7B. Treatment-related survival analysis of candidate 5 site-gene panel in TCGA, Beltran et al, and PROMOTE patient cohorts.
Figure 7A:
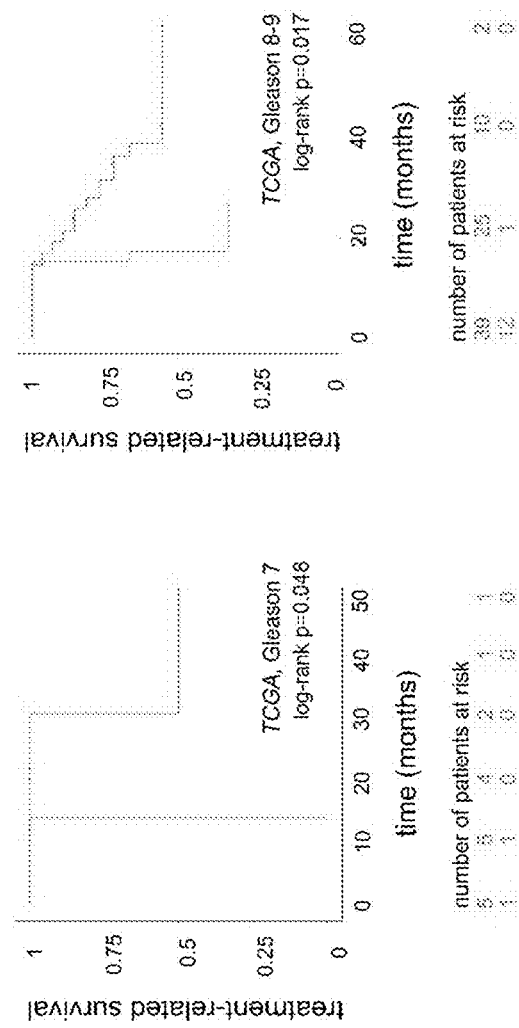

In addition to validation in the TCGA-PRAD cohort, it was determined whether the 5 site-gene panel can determine failed ADT response in (i) *Stand Up To Cancer* (*SU2C*) (Robinson et al., 2015) patient cohort with castration-resistant prostate cancer (CRPC) metastatic samples (n=51); (ii) Grasso et al (Grasso et al., 2012) patient cohort with androgen-naive primary tumors (n=58) and CRPC metastatic samples (n=33); (iii) Cai et al (Cai et al., 2013) patient cohort with androgen-naïve primary tumors (n=21) and CRPC bone metastasis (n=19) (FIGS. 6D-6F); (iv) Beltran et al (Beltran et al., 2011) patient cohort with CRPC metastatic samples (n=34); and (v) *Prostate Cancer Medically Optimized Genome-Enhanced Therapy* (*PROMOTE*) (Kohli et al., 2015) patient cohort with CRPC metastatic samples that were treated with Abiraterone acetate for 12 weeks with subsequent treatment failure (n=29) (FIG. 7B). First, to evaluate if expression levels of the 5 site-gene panel in primary tumors with poor ADT response (i.e., group 2) are comparable to metastatic CRPC samples (i.e., metastatic samples with ADT failure) and demonstrate that profiles of patients that received ADT after surgery with subsequent BCR are similar to the profiles of patients who have failed ADT with metastatic disease, expression levels from the 5 site-gene panel in the TCGA-PRAD patient cohort (group 1 and group 2, primary tumors) and SU2C (CRPC metastatic samples) (FIG. 6D), which demonstrated that genes from the 5 site-gene panel (i) substantially differ between patient with favorable ADT response (i.e., group 1) and poor ADT response (i.e., group 2) (p=0.01) as well as between patients with favorable ADT response (i.e., group 1) and CRPC metastasis (p=0.00006); and (ii) have similar expression patterns in patients with poor ADT response (i.e., group 2) and CRPC metastatic samples (p=0.26) (FIG. 6D), demonstrating that 5-site gene panel has comparable expression levels in primary tumors with poor ADT response and metastatic CRPC samples. Subsequently, to further confirm the ability of the 5 site-gene panel to identify samples with CRPC ADT failure, expression profiles from patient cohorts in Grasso et al (Grasso et al., 2012) and Cai et al (Cai et al., 2013) were subjected to t-SNE clustering, which demonstrated the ability of the five gene panel to separate CRPC (grey) from androgen sensitive (AS) (light blue) samples (sensitivity to cluster CRPC into one group was 100% in both datasets) (FIGS. 6E-6F). Finally, to confirm the ability of the 5-site-gene panel to effectively distinguish between CRPC ADT failure samples and TCGA-PRAD samples with favorable ADT response, patient profiles in Beltran et al (Beltran et al., 2011) and PROMOTE (Kohli et al., 2015) were compared to the patients from the TCGA-PRAD with favorable treatment response (i.e., group 1) through multiple logistic regression followed by ROC analysis, which demonstrated that the 5 site-gene panel can effectively distinguish between TCGA-PRAD with favorable ADT response and Beltran et al (Beltran et al., 2011) (AUROC=0.83) and PROMOTE (Kohli et al., 2015) (AUROC=0.98) (FIG. 7B).

Taken together, these observations indicate a significant ability of the 5-site gene panel to predict ADT failure in diverse prostate cancer cohorts.

Example 7

Multimodal Comparative Analysis Demonstrates Statistical Significance of the Predictive Model For multimodal performance assessment of the model, the following were evaluated (i) advantages of the model over methylation, expression, and correlation data alone; (ii) non-randomness of its predictive ability through comparison to 5 site-gene pairs selected at random; (iii) robustness of the findings through evaluation of how well the model can classify patients at varying levels of noise; and demonstrated that (iv) predictive ability of the panel is not affected by the commonly used prognostic clinical variables, such as pathological and clinical T-stage, Gleason score, age, and therapy subtypes.

To assess advantages of the model over other commonly used methods, the ability of the 5 site-gene panel to predict ADT failure was compared to (i) differentially methylated sites alone (two-tail two-sample Student t-test $p<0.001$); (ii) differentially expressed genes alone (two-tail two-sample Student t-test $p<0.001$); and (iii) site-gene pairs identified from the correlation analysis (Pearson correlation $p<0.05$); (iv) top 5 differentially expressed genes; and (v) top 5 differentially methylated genes which have also been utilized by (Wu et al., 2016, Amaro et al., 2014, Geybels et al., 2016, Ryl et al., Benzon et al., 2017, Bibikova et al., 2007, Yu et al., Wang et al., 2015, Mitrofanova et al., Risk et al., 2010, Cai et al., Barfeld et al., Massie et al., 2017, Litovkin et al., 2015, Haldrup et al., 2013) and achieved significant results in predicting disease progression. We have compared the ability of the model to predict ADT response to the therapeutic predictive ability of methylation, expression and correlation alone through Kaplan-Meier survival analysis (results reported through log-rank p-value and hazard ratio) and concordance index (i.e., c-index) in the TCGA-PRAD validation set and observed that the 5 site-gene panel outperforms these data types in correctly classifying patients at risk of ADT resistance (FIG. 8A).

Furthermore, the non-randomness of the predictive ability of the 5 site-gene panel was evaluated through comparison to 5 site-gene pairs selected at random. For this, two random models were defined, where five site-gene pairs were selected at random from the pool of (i) all sites from the HumanMethylation450 platform (FIG. 8B, random model 1, dark grey); and (ii) sites from TSS 200/1500, 5' UTR, and $1^{st}$ exon regions (FIG. 8B, random model 2, light green). Five random sites were sampled 10,000 times in the TCGA-PRAD validation set and then evaluated for their ability to predict therapeutic response through Kaplan-Meier survival analysis. Empirical p-value for each random model was estimated as a number of times log-rank p-values for the randomly selected sites reached or outperformed the log-rank p-value for the original 5 site-gene panel, which demonstrated non-randomness of the 5 site-gene panel predictive ability (random model 1 $p=0.010$; random model 2 $p=0.011$) (FIG. 8B).

To test robustness of the predictive ability for the 5 site-gene panel, noise was introduced into the TCGA-PRAD validation set (excluding samples used for signature reconstruction to avoid overfitting, n=58) and measured how much noise can be "tolerated" and have the 5 site-gene panel can still accurately predict treatment response. For this, ADT treated patients (i.e., introduced False Negatives, FN) were randomly removed or ADT treated patients (i.e., introduced False Positives, FP) were randomly added from or to the validation set (FIG. 8C). Let us denote the number of patients removed or added at each iteration as i (i=1 . . . 58). At each iteration, the ability of the 5 site-gene panel to classify patients and predict therapeutic response using Kaplan-Meier survival analysis was evaluated. Each $i^{th}$ iteration was run 10,000 times and median log-rank p-values across 10,000 runs were reported (FIG. 8C). This analysis demonstrated that the 5 site-gene panel could successfully predict therapeutic response even at 31% FN ($18/58$) and at 9% FP ($5/58$) rates (FIG. 8C), which demonstrates the robustness of its predictive ability even at high noise levels.

Figure 9C:
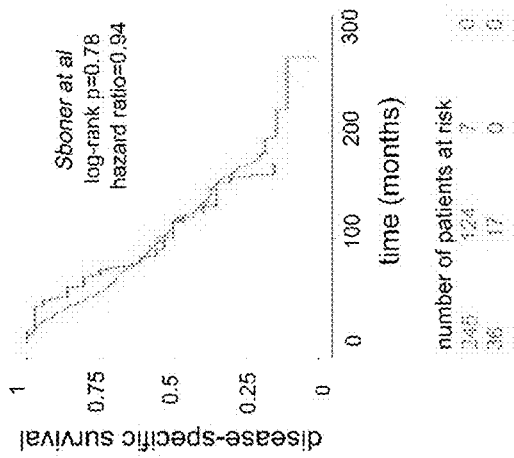
FIGS. 9A-9C. Multimodal analysis of signature thresholds and negative control dataset.
Figure 9B:
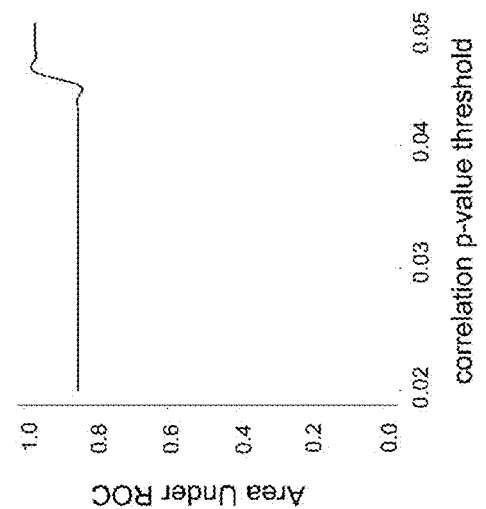
Figure 9A:
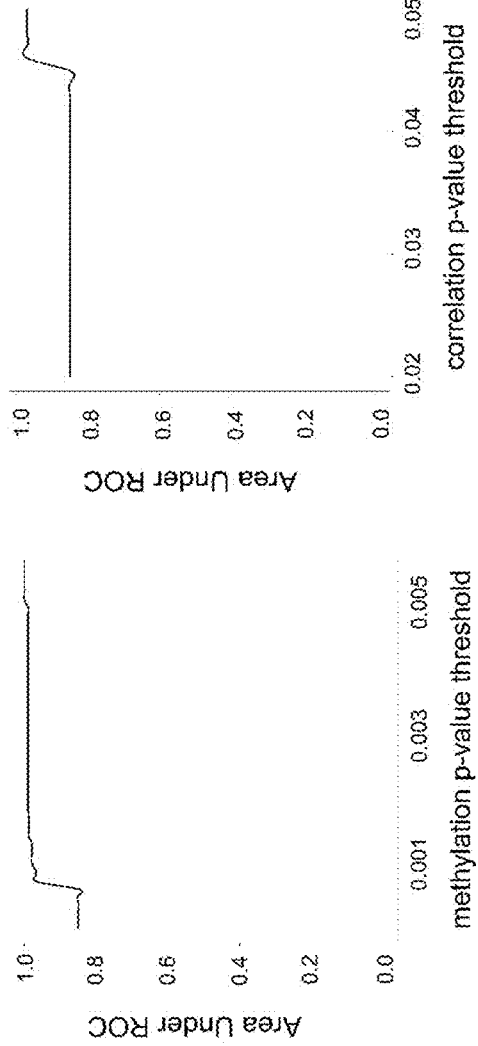

To confirm that fluctuations in the signature threshold levels do not affect power of the model to identify distinct treatment response groups, the predictive ability of the model was evaluated while varying (i) methylation signature threshold ($p<0.001$); and (ii) correlation threshold ($p<0.05$) through multiple logistic regression at each threshold level followed by ROC analysis, which demonstrated that the model kept its predictive power at varying methylation signature (AUROC between 0.85 and 0.99) and correlation (AUROC between 0.85 and 0.98) thresholds (FIGS. 9A-9B).

Finally, to confirm that the 5 site-gene panel is an indicator of primary resistance and not overall disease aggressiveness, as a negative control, it was determined whether the 5 site-gene panel can classify patients based on disease aggressiveness in Sboner et al dataset (Sboner et al., 2010), also known as a Swedish Watchful Waiting cohort with patients up to 30 years of clinical follow not subjected to treatments (n=281, localized prostate tumors). The Kaplan-Meier survival analysis confirmed that predictive ability of the panel is independent of disease aggressiveness (log-rank $p=0.78$, hazard ratio=0.94, prostate cancer-related death was used as a clinical end-point) (FIG. 9C). Furthermore, to confirm this finding, whether the predictive ability of the 5 site-gene panel is independent of commonly used prognostic clinical variables (Halabi et al., 2013, Guinney et al.), such as pathological and clinical T-stage, Gleason score, patient age and therapy subtypes, which include luteinizing hormone releasing hormone (LHRH) agonists (i.e., bind to pituitary LHRH receptor to stimulate the production of luteinizing hormone thus interfering with the yield of testosterone), LHRH antagonists (i.e., block the pituitary LHRH receptor thus completely shutting down the production of testosterone), CYP17 inhibitors (i.e., block CYP17 enzyme essential for androgen synthesis) and anti-androgens (i.e., bind to androgen receptor blocking androgen binding) was evaluated. For this, multivariable Cox proportional hazard model analysis was performed (Bender et al., 2005) in the TCGA-PRAD validation set, which confirmed that (i) none of these variables were predictive of ADT response and (ii) they did not affect predictive ability of the 5 site-gene panel (FIG. 8D).

Given that this model has a highly accurate independent ability to predict ADT response, this panel can be utilized to classify patients at risk of developing resistance to ADT, prioritize patients for ADT intervention, and can be incorporated into personalized and precision therapeutic platforms.

REFERENCES

ABESHOUSE et al., 2015. The Molecular Taxonomy of Primary Prostate Cancer. *Cell*, 163, 1011-1025.

AKAMATSU et al., The Placental Gene <em>PEG10</em> Promotes Progression of Neuroendocrine Prostate Cancer. *Cell Reports*, 12, 922-936.

ALVAREZ et al., 2016. Functional characterization of somatic mutations in cancer using network-based inference of protein activity. *Nature genetics*, 48, 838.

AMARO et al., 2014. Validation of proposed prostate cancer biomarkers with gene expression data: a long road to travel. *Cancer Metastasis Reviews*, 33, 657-671.

BARFELD et al., c-Myc Antagonises the Transcriptional Activity of the Androgen Receptor in Prostate Cancer Affecting Key Gene Networks. *EBioMedicine*, 18, 83-93.

BAXTER et al., 2014. Epigenetic regulation in cancer progression. *Cell & Bioscience*, 4, 45.

BELTRAN et al., 2016. Divergent clonal evolution of castration-resistant neuroendocrine prostate cancer. *Nat Med*, 22, 298-305.

BELTRAN et al., 2011. Molecular Characterization of Neuroendocrine Prostate Cancer and Identification of New Drug Targets. *Cancer discovery*, 1, 487-495.

BENDER, et al., 2005. Generating survival times to simulate Cox proportional hazards models. *Statistics in medicine*, 24, 1713-1723.

BENZON et al., 2017. Correlation of B7-H3 with androgen receptor, immune pathways and poor outcome in prostate cancer: an expression-based analysis. *Prostate Cancer Prostatic Dis*, 20, 28-35.

BIBIKOV et al., 2007. Expression signatures that correlated with Gleason score and relapse in prostate cancer. *Genomics*, 89, 666-672.

BRAY et al., 2013. Global estimates of cancer prevalence for 27 sites in the adult population in 2008. *Int J Cancer*, 132, 1133-45.

BUTLER, M. G. 2009. Genomic imprinting disorders in humans: a mini-review. *Journal of Assisted Reproduction and Genetics*, 26, 477-486.

CAI et al., 2013. ERG induces androgen receptor-mediated regulation of SOX9 in prostate cancer. *J Clin Invest*, 123, 1109-22.

CAI et al., Prognostic Biomarker Identification Through Integrating the Gene Signatures of Hepatocellular Carcinoma Properties. *EBioMedicine*, 19, 18-30.

CHANDRASEKAR, T., YANG, J. C., GAO, A. C. & EVANS, C. P. 2015. Mechanisms of resistance in castration-resistant prostate cancer (CRPC). *Translational Andrology and Urology*, 4, 365-380.

CHATTERJEE, S. & HADI, A. S. 2006. Simple linear regression. *Regression Analysis by Example, Fourth Edition*, 21-51.

CHEN et al., 2015. Changes in DNA methylation are associated with the development of drug resistance in cervical cancer cells. *Cancer Cell International*, 15, 98.

CONERLY, M. & GRADY, W. M. 2010. Insights into the role of DNA methylation in disease through the use of mouse models. *Disease Models & Mechanisms*, 3, 290-297.

DEATON, A. M. & BIRD, A. 2011. CpG islands and the regulation of transcription. *Genes Dev*, 25, 1010-22.

DHINGRA et al., 2017. Identification of novel prostate cancer drivers using RegNetDriver: a framework for integration of genetic and epigenetic alterations with tissue-specific regulatory network. *Genome Biology*, 18, 141.

DU, et al., 2010. Comparison of Beta-value and M-value methods for quantifying methylation levels by microarray analysis. *BMC Bioinformatics*, 11, 587.

EHRLICH, M. 2002. DNA methylation in cancer: too much, but also too little. *Oncogene*, 21, 5400-13.

EPSTEIN et al., 2014. Proposed morphologic classification of prostate cancer with neuroendocrine differentiation. *Am J Surg Pathol*, 38, 756-67.

EYRE et al., 2014. Reversing paclitaxel resistance in ovarian cancer cells via inhibition of the ABCB1 expressing side population. *Tumour Biol*, 35, 9879-92.

FISHER, R. A. 1922. On the Interpretation of $\chi^2$ from Contingency Tables, and the Calculation of P. *Journal of the Royal Statistical Society*, 85, 87-94.

GARDINER-GARDEN, M. & FROMMER, M. 1987. CpG Islands in vertebrate genomes. *Journal of Molecular Biology*, 196, 261-282.

GEYBELS et al., 2016. Epigenetic signature of Gleason score and prostate cancer recurrence after radical prostatectomy. *Clinical epigenetics*, 8, 97.

GIFFORD et al., 2004. The acquisition of hMLH1 methylation in plasma DNA after chemotherapy predicts poor survival for ovarian cancer patients. *Clin Cancer Res*, 10, 4420-6.

GOEL et al., 2010. Understanding survival analysis: Kaplan-Meier estimate. *International Journal of Ayurveda Research*, 1, 274-278.

GRASSO, C. S., WU, Y. M., ROBINSON, D. R., CAO, X., DHANASEKARAN, S. M., KHAN, A. P., QUIST, M. J., JING, X., LONIGRO, R. J., BRENNER, J. C., et al. 2012. The mutational landscape of lethal castration-resistant prostate cancer. *Nature*, 487, 239-43.

GREGER, V., PASSARGE, E., HOPPING, W., MESSMER, E. & HORSTHEMKE, B. 1989. Epigenetic changes may contribute to the formation and spontaneous regression of retinoblastoma. *Hum Genet*, 83, 155-8.

GUINNEY et al., Prediction of overall survival for patients with metastatic castration-resistant prostate cancer: development of a prognostic model through a crowdsourced challenge with open clinical trial data. *The Lancet Oncology*, 18, 132-142.

HAAS et al., 2008. The Worldwide Epidemiology of Prostate Cancer: Perspectives from Autopsy Studies. *The Canadian journal of urology*, 15, 3866-3871.

HAJIAN-TILAKI, K. 2013. Receiver Operating Characteristic (ROC) Curve Analysis for Medical Diagnostic Test Evaluation. *Caspian Journal of Internal Medicine*, 4, 627-635.

HALABI et al., 2013. Prognostic Model Predicting Metastatic Castration-Resistant Prostate Cancer Survival in Men Treated With Second-Line Chemotherapy. *JNCI Journal of the National Cancer Institute*, 105, 1729-1737.

HALDRUP et al., 2013. DNA Methylation Signatures for Prediction of Biochemical Recurrence After Radical Prostatectomy of Clinically Localized Prostate Cancer. *Journal of Clinical Oncology*, 31, 3250-3258.

HANLEY, J. A. & MCNEIL, B. J. 1982. The meaning and use of the area under a receiver operating characteristic (ROC) curve. *Radiology*, 143, 29-36.

HERSHEY, J. R. & OLSEN, P. A. Approximating the Kullback Leibler divergence between Gaussian mixture models. Acoustics, Speech and Signal Processing, 2007. ICASSP 2007. IEEE International Conference on, 2007. IEEE, IV-317-IV-320.

HUGGINS, C. & HODGES, C. V. 1972. Studies on prostatic cancer. I. The effect of castration, of estrogen and androgen injection on serum phosphatases in metastatic carcinoma of the prostate. *CA Cancer J Clin*, 22, 232-40.

ILI, C. G., VISCARRA, T., ARAYA, J. C., LOPEZ, J., MORA, B., RETAMAL, J., AEDO, S., BELLOLIO, E., ROA, J. C. & BREBI, P. 2016. Abstract B28: FKBP6 gene is involved in progression of cervical cancer. *Molecular Cancer Research*, 14, B28.

ILLINGWORTH, R. S. & BIRD, A. P. 2009. CpG islands—'A rough guide'. *FEBS Letters*, 583, 1713-1720.

JOHNSON et al., 2012. The Role of DNA Methylation in Aging, Rejuvenation, and Age-Related Disease. *Rejuvenation Research*, 15, 483-494.

JONES, P. A. & BAYLIN, S. B. 2002. The fundamental role of epigenetic events in cancer. *Nat Rev Genet*, 3, 415-28.

KARANTANOS, T., CORN, P. G. & THOMPSON, T. C. 2013. Prostate cancer progression after androgen deprivation therapy: mechanisms of castrate resistance and novel therapeutic approaches. *Oncogene*, 32, 5501-5511.

KASSAMBARA, A., KOSINSKI, M. & BIECEK, P. 2017. survminer: Drawing Survival Curves using 'ggplot2'. R package version 0.3, 1.

KOHLI et al., 2015. Mutational Landscapes of Sequential Prostate Metastases and Matched Patient Derived Xenografts during Enzalutamide Therapy. *PLoS ONE*, 10, e0145176.

LAIRD, P. W. & JAENISCH, R. 1996. The role of DNA methylation in cancer genetic and epigenetics. *Annu Rev Genet*, 30, 441-64.

LALLOUS et al., 2016. Functional analysis of androgen receptor mutations that confer anti-androgen resistance identified in circulating cell-free DNA from prostate cancer patients. *Genome Biology*, 17, 10.

LAMPH et al., 1988. Induction of proto-oncogene JUN/AP-1 by serum and TPA. *Nature*, 334, 629-631.

LEE et al., N-Myc Drives Neuroendocrine Prostate Cancer Initiated from Human Prostate Epithelial Cells. *Cancer Cell*, 29, 536-547.

LITOVKIN et al., 2015. DNA methylation-guided prediction of clinical failure in high-risk prostate cancer. *PloS one*, 10, e0130651.

LONERGAN, P. E. & TINDALL, D. J. 2011. Androgen receptor signaling in prostate cancer development and progression. *Journal of Carcinogenesis*, 10, 20.

LOVE, M. I., HUBER, W. & ANDERS, S. 2014. Moderated estimation of fold change and dispersion for RNA-seq data with DESeq2. *Genome Biology*, 15, 550.

LUCZAK, M. W. & JAGODZINSKI, P. P. 2006. The role of DNA methylation in cancer development. *Folia Histochem Cytobiol*, 44, 143-54.

MAATEN, L. V. D. & HINTON, G. 2008. Visualizing data using t-SNE. *Journal of Machine Learning Research*, 9, 2579-2605.

MARZESE, D. M. & HOON, D. S. B. 2015. Emerging technologies for studying DNA methylation for the molecular diagnosis of cancer. *Expert review of molecular diagnostics*, 15, 647-664.

MASSIE, C. E., MILLS, I. G. & LYNCH, A. G. 2017. The importance of DNA methylation in prostate cancer development. *The Journal of Steroid Biochemistry and Molecular Biology*, 166, 1-15.

MILDE-LANGOSCH, K., KAPPES, H., RIETHDORF, S., LONING, T. & BAMBERGER, A. M. 2003. FosB is highly expressed in normal mammary epithelia, but down-regulated in poorly differentiated breast carcinomas. *Breast Cancer Res Treat*, 77, 265-75.

MILLER et al., 2016. MicroRNAs associated with small bowel neuroendocrine tumours and their metastases. *Endocrine-Related Cancer*, 23, 711-726.

MITROFANOVA et al., Predicting Drug Response in Human Prostate Cancer from Preclinical Analysis of In  Vivo Mouse Models. *Cell Reports*, 12, 2060-2071.

MORRIS, T. J. & BECK, S. 2015. Analysis pipelines and packages for Infinium HumanMethylation450 BeadChip (450 k) data. *Methods* (San Diego, Calif.), 72, 3-8.

MUKAKA, M. M. 2012. A guide to appropriate use of Correlation coefficient in medical research. *Malawi Medical Journal: The Journal of Medical Association of Malawi*, 24, 69-71.

NIE et al., 2015. Overexpression of stathmin 1 is a poor prognostic biomarker in non-small cell lung cancer. *Lab Invest*, 95, 56-64.

PATHIRAJA et al., 2014. Epigenetic reprogramming of HOXC10 in endocrine-resistant breast cancer. *Science translational medicine*, 6, 229ra41-229ra41.

RHEE et al., 2013. Integrated analysis of genome-wide DNA methylation and gene expression profiles in molecular subtypes of breast cancer. *Nucleic Acids Research*, 41, 8464-8474.

RISK, M. C., KNUDSEN, B. S., COLEMAN, I., DUMPIT, R. F., KRISTAL, A. R., LEMEUR, N., GENTLEMAN, R. C., TRUE, L. D., NELSON, P. S. & LIN, D. W. 2010. Differential gene expression in benign prostate epithelium of men with and without prostate cancer: evidence for a prostate cancer field effect. *Clin Cancer Res*, 16, 5414-23.

ROBIN, X., TURCK, N., HAINARD, A., TIBERTI, N., LISACEK, F., SANCHEZ, J.-C. & MÜLLER, M. 2011. pROC: an open-source package for R and S+ to analyze and compare ROC curves. *BMC bioinformatics*, 12, 77.

ROBINSON et al., 2015. Integrative clinical genomics of advanced prostate cancer. *Cell*, 161, 1215-28.

RYL et al., Cell-Cycle Position of Single MYC-Driven Cancer Cells Dictates Their Susceptibility to a Chemotherapeutic Drug. *Cell Systems*, 5, 237-250.e8.

SAAL et al., 2007. Poor prognosis in carcinoma is associated with a gene expression signature of aberrant PTEN tumor suppressor pathway activity. *Proceedings of the National Academy of Sciences of the United States of America*, 104, 7564-7569.

SBONER et al., 2010. Molecular sampling of prostate cancer: a dilemma for predicting disease progression. *BMC Medical Genomics*, 3, 8-8.

SCHER, H. I. & SAWYERS, C. L. 2005. Biology of Progressive, Castration-Resistant Prostate Cancer: Directed Therapies Targeting the Androgen-Receptor Signaling Axis. *Journal of Clinical Oncology*, 23, 8253-8261.

SCHOENBORN, J. R., NELSON, P. & FANG, M. 2013. Genomic profiling defines subtypes of prostate cancer with the potential for therapeutic stratification. *Clinical cancer research: an official journal of the American Association for Cancer Research*, 19, 4058-4066.

SCHRÖDER et al., 2011. survcomp: an R/Bioconductor package for performance assessment and comparison of survival models. *Bioinformatics*, 27, 3206-3208.

SENGUPTA, P. K., EHRLICH, M. & SMITH, B. D. 1999. A methylation-responsive MDBP/RFX site is in the first exon of the collagen alpha2(I) promoter. *J Biol Chem*, 274, 36649-55.

SHAHZAD et al., 2010. Stress effects on FosB- and interleukin-8 (IL8)-driven ovarian cancer growth and metastasis. *J Biol Chem*, 285, 35462-70.

SHARMA, S., KELLY, T. K. & JONES, P. A. 2010. Epigenetics in cancer. *Carcinogenesis*, 31, 27-36.

SHAULIAN, E. & KARIN, M. 2001. AP-1 in cell proliferation and survival. *Oncogene*, 20, 2390-400.

SHAULIAN, E. & KARIN, M. 2002. AP-1 as a regulator of cell life and death. *Nat Cell Biol*, 4, E131-6.

SHEN, M. M. & ABATE-SHEN, C. 2010. Molecular genetics of prostate cancer: new prospects for old challenges. *Genes Dev*, 24, 1967-2000.

SIEGEL, R. L., MILLER, K. D. & JEMAL, A. 2016. Cancer statistics, 2016. *CA Cancer J Clin*, 66, 7-30.

SMITH, Z. D. & MEISSNER, A. 2013. DNA methylation: roles in mammalian development. *Nat Rev Genet*, 14, 204-220.

STOUFFER et al., 1949. The American soldier: Adjustment during army life. (Studies in social psychology in World War II), Vol. 1.

STOYANOVA et al., 2016. Activation of Notch1 synergizes with multiple pathways in promoting castration-resistant prostate cancer. *Proceedings of the National Academy of Sciences*, 113, E6457-E6466.

SUBRAMANIAN et al., 2005. Gene set enrichment analysis: A knowledge-based approach for interpreting genome-wide expression profiles. *Proceedings of the National Academy of Sciences*, 102, 15545-15550.

THERNEAU, T. 2015. A package for survival analysis in S. R package version 2.38. Retrieved from *CRAN. R-project.org/package=survival*.

THERNEAU, T. & GRAMBSCH, P. 2010. *Modeling Survival Data: Extending the Cox Model (Statistics for Biology and Health)*, Springer.

TING, C.-H., CHEN, Y.-C., WU, C.-J. & CHEN, J.-Y. 2016. Targeting FOSB with a cationic antimicrobial peptide, TP4, for treatment of triple-negative breast cancer. *Oncotarget*, 7, 40329-40347.

TULCHINSKY, E. 2000. Fos family members: regulation, structure and role in oncogenic transformation. *Histol Histopathol*, 15, 921-8.

URBANUCCI et al., 2017. Androgen Receptor Deregulation Drives Bromodomain-Mediated Chromatin Alterations in Prostate Cancer. *Cell Reports*, 19, 2045-2059.

VAN DAM, H. & CASTELLAZZI, M. 2001. Distinct roles of Jun: Fos and Jun: ATF dimers in oncogenesis. *Oncogene*, 20, 2453-64.

WAJED, S. A., LAIRD, P. W. & DEMEESTER, T. R. 2001. DNA Methylation: An Alternative Pathway to Cancer. *Annals of Surgery*, 234, 10-20.

WALLACE et al., 2014. Current Approaches, Challenges and Future Directions for Monitoring Treatment Response in Prostate Cancer. *Journal of Cancer*, 5, 3-24.

WANG, L., GONG, Y., CHIPPADA-VENKATA, U., HECK, M. M., RETZ, M., NAWROTH, R., GALSKY, M., TSAO, C.-K., SCHADT, E., DE BONO, J., et al. 2015. A robust blood gene expression-based prognostic model for castration-resistant prostate cancer. *BMC Medicine*, 13, 201.

WOO et al., 2017. Integrative analysis of genomic and epigenomic regulation of the transcriptome in liver cancer. *Nature Communications*, 8, 839.

WU et al., 2016. Methylation profiling identified novel differentially methylated markers including OPCML and FLRT2 in prostate cancer. *Epigenetics*, 11, 247-258.

YAO et al., 2015. Inferring regulatory element landscapes and transcription factor networks from cancer methylomes. *Genome Biol*, 16, 105.

YU et al., Association of Omics Features with Histopathology Patterns in Lung Adenocarcinoma. *Cell Systems*.

ZEILEIS, A., KLEIBER, C. & JACKMAN, S. 2008. Regression models for count data in R. *Journal of statistical software*, 27, 1-25.

ZHANG et al., 1990. Binding sites in mammalian genes and viral gene regulatory regions recognized by methylated DNA-binding protein. *Nucleic acids research*, 18, 6253-6260.

ZHANG et al., 1986. Effect of site-specific DNA methylation and mutagenesis on recognition by methylated DNA-binding protein from human placenta. *Nucleic Acids Res*, 14, 8387-97.

ZHU et al., 2015. Effects of stathmin 1 silencing by siRNA on sensitivity of esophageal cancer cells Eca-109 to paclitaxel. *Genet Mol Res*, 14, 18695-702.

ZÖCHBAUER-MÜLLER et al., 2001. 5' CpG Island Methylation of the FHIT Gene Is Correlated with Loss of Gene Expression in Lung and Breast Cancer. *Cancer Research*, 61, 3581-3585.

Example 8

Prostate Cancer Genes that do not Predict Response to ADT

Figure 10:
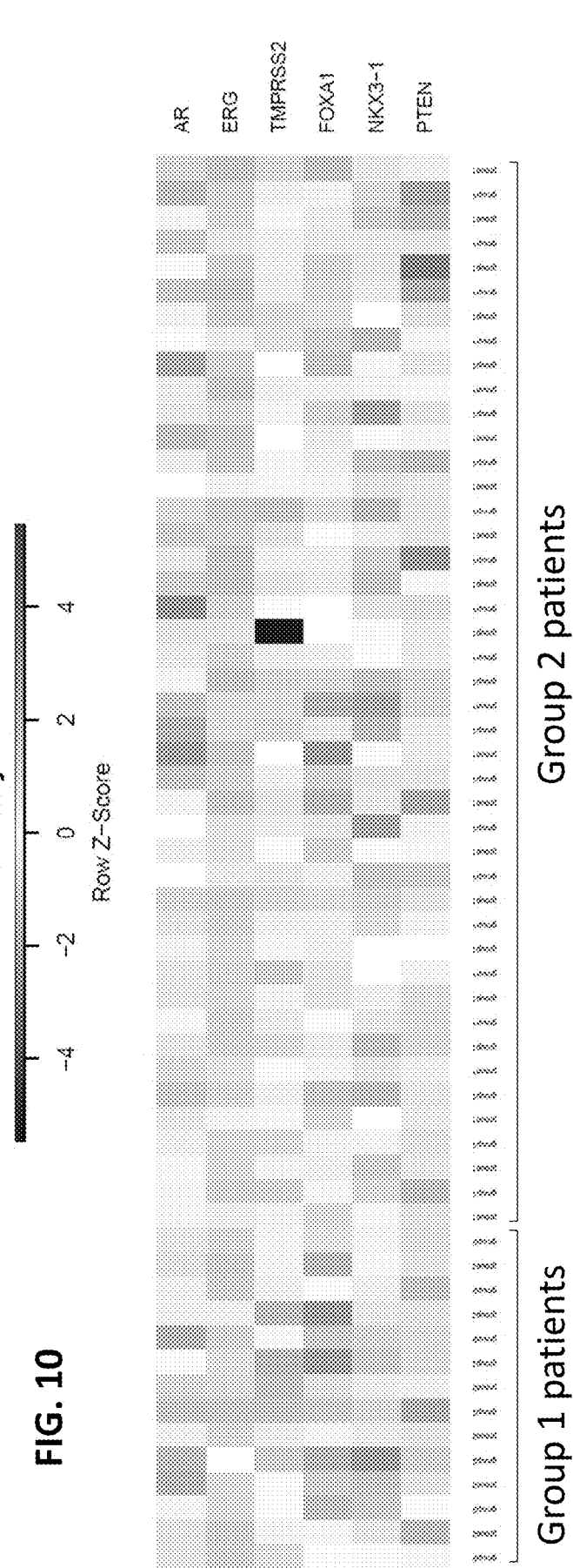
FIG. 10. Heatmap of gene expression for AR, ERG, TMPRSS2, FOXA1, NKX3-1, and PTEN in two patient groups, Group 1 having a favorable ADT response and Group 2 having an unfavorable ADT response. The heatmap shows no visual differences between the two groups and, thus, demonstrates that expression of AR, ERG, TMPRSS2, FOXA1, NKX3-1, and PTEN do not predict a response to ADT.

The heatmap shown in FIG. 10 demonstrates that commonly used markers (genes) of prostate cancer aggressiveness, such as androgen receptor (AR), erythroblast transformation-specific (ETS)-related gene (ERG), transmembrane protease serine 2 (TMPRSS2), forkhead box protein A1 (FOXA1), NK3 homeobox 1 (NKX3-1), and phosphatase and tensin homolog (PTEN) do not predict response to androgen deprivation.

To construct this heatmap, two patient groups (with different treatment responses, where group 2 exhibited a worse treatment response) were compared in which the five markers (AR, ERG, TMPRSS2, FOXA1, NKX3-1, and PTEN) were identified and examined for differentiation of the two patient groups (in other words, whether or not AR, ERG, TMPRSS2, FOXA1, NKX3-1, and PTEN can be used to predict treatment response). The heatmap is a visual representation of expression levels of the genes above in those two patient groups, and it shows no visual differences between the groups, indicating that AR, ERG, TMPRSS2, FOXA1, NKX3-1, and PTEN cannot predict treatment response.

Shown in Table 3 are t values and p values generated using the Welch t-test, and they show that there are no statistically significant differences in expression levels of these genes between the two groups (no p-value is <0.05; therefore, no gene is significant). Thus, AR, ERG, TMPRSS2, FOXA1, NKX3-1, and PTEN would not predict a treatment response in the two patient groups. Further, CSPG5, FKBP6, FOSB, STMN1, and TTC27 are not correlated with any of AR, ERG, TMPRSS2, FOXA1, NKX3-1, and PTEN, and, thus, CSPG5, FKBP6, FOSB, STMN1, and TTC27 exhibit an independent predictive value.

TABLE 3 t values and p values for prostate cancer genes that do not predict response to ADT

| Gene | t values | p values |
| --- | --- | --- |
| AR | 0.405869 | 0.6890388 |
| ERG | −0.0532515 | 0.9580058 |
| TMPRSS2 | −0.8970417 | 0.3784689 |
| FOXA1 | −0.8663231 | 0.3986855 |

TABLE 3-continued t values and p values for prostate cancer
genes that do not predict response to ADT

| Gene | t values | p values |
| --- | --- | --- |
| NKX3-1 | −1.5445678 | 0.1357174 |
| PTEN | −0.1577335 | 0.8760966 |

In view of the many possible embodiments to which the principles of the disclosed may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of treating prostate cancer, comprising:
(i) measuring
mRNA expression of CSPG5, FKBP6, FOSB, STMN1, and TTC27 in a prostate cancer sample from the subject relative to a control for measuring mRNA expression, wherein the control for measuring mRNA expression is (1) a prostate cancer sample known to respond to androgen deprivation therapy (ADT) or (2) a reference value or range of reference values representing a prostate cancer sample known to respond to ADT; and/or
DNA methylation within the TSS 200/1500, 5' UTR, or $1^{st}$ exon regions of CSPG5, FKBP6, FOSB, STMN1, and TTC27 in a prostate cancer sample from the subject relative to a control for measuring DNA methylation, wherein the control for measuring DNA methylation is (1) a prostate cancer sample known to respond to ADT or (2) a reference value or range of reference values representing a prostate cancer sample known to respond to ADT;
(ii) determining that
the subject with prostate cancer will respond to ADT when:
TTC27, STMN1, and CSPG5 have decreased mRNA expression in the prostate cancer sample from the subject relative to the control for measuring mRNA expression and that FOSB and FKBP6 have increased mRNA expression in the prostate cancer sample from the subject relative to the control for measuring mRNA expression; and/or
FKBP6 has decreased DNA methylation in the prostate cancer sample from the subject relative to the control for measuring DNA methylation and that FOSB, TTC27, STMN1, and CSPG5 have increased DNA methylation in the prostate cancer sample from the subject relative to the control for measuring DNA methylation; and
(iii) administering ADT to the subject.

2. The method of claim 1, further comprising:
measuring prostate specific antigen (PSA) in a blood sample from the subject;
determining a Gleason score for the prostate cancer; or combinations thereof.

3. The method of claim 1, further comprising:
obtaining the prostate cancer sample from the subject;
contacting the prostate cancer sample from the subject and the control for measuring mRNA expression and/or the control for measuring DNA methylation with one or more nucleic acid probes, nucleic acid primers, or both, specific for CSPG5, FKBP6, FOSB, STMN1, and TTC27;
or combinations thereof.

4. The method of claim 1, wherein the subject is a human subject.

5. The method of claim 1, further comprising measuring mRNA expression, measuring DNA methylation, or both of at least one housekeeping molecule.

6. The method of claim 1, wherein measuring mRNA expression or measuring DNA methylation comprises using a microscope device.

7. The method of claim 1, wherein the ADT comprises chemical castration, anti-androgen therapy, or both.

8. The method of claim 1, wherein the prostate cancer is a primary prostate cancer.

9. The method of claim 1, wherein the prostate cancer is a metastatic prostate cancer.

10. The method of claim 1, wherein the subject has had a prostatectomy.

11. The method of claim 1, wherein the determining the subject with prostate cancer will respond to ADT is statistically significant.

12. The method of claim 1, wherein the subject is selected to receive a prostatectomy.

13. The method of claim 1, wherein the method comprises:
measuring mRNA expression of CSPG5, FKBP6, FOSB, STMN1, and TTC27 in a prostate cancer sample from the subject relative to a control for measuring mRNA expression, wherein the control for measuring mRNA expression is (1) a prostate cancer sample known to respond to ADT or (2) a reference value or range of reference values representing a prostate cancer sample known to respond to ADT;
determining that the subject with prostate cancer will respond to ADT when TTC27, STMN1, and CSPG5 have decreased mRNA expression in the prostate cancer sample from the subject relative to the control for measuring mRNA expression and that FOSB and FKBP6 have increased mRNA expression in the prostate cancer sample from the subject relative to the control for measuring mRNA expression; and
administering ADT to the subject.

14. The method of claim 1, wherein the method comprises:
measuring DNA methylation within the TSS 200/1500, 5' UTR, or $1^{st}$ exon region of CSPG5, FKBP6, FOSB, STMN1, and TTC27 in a prostate cancer sample from the subject relative to a control for measuring DNA methylation, wherein the control for measuring DNA methylation is (1) a prostate cancer sample known to respond to ADT or (2) a reference value or range of such values representing a prostate cancer sample known to respond to ADT;
determining that the subject with prostate cancer will respond to ADT when FKBP6 has decreased DNA methylation in the prostate cancer sample from the subject relative to the control for measuring DNA methylation and that FOSB, TTC27, STMN1, and CSPG5 have increased DNA methylation in the prostate cancer sample from the subject relative to the control for measuring DNA methylation; and
administering ADT to the subject.

15. A method of treating prostate cancer in a subject, comprising:
(i) measuring:
decreased mRNA expression of TTC27, STMN1, and CSPG5 and increased mRNA expression of FOSB and FKBP6 in a prostate cancer sample from the subject relative to a control for measuring mRNA expression, wherein the control for measuring expression is (1) a prostate cancer sample known to respond to ADT or (2) a reference value or range of reference values representing a prostate cancer sample known to respond to ADT, and/or decreased DNA methylation within the TSS 200/1500, 5' UTR, or $1^{st}$ exon regions of FKBP6 and increased DNA methylation FOSB, TTC27, STMN1, and CSPG5 in a prostate cancer sample from the subject relative to a control for measuring DNA methylation, wherein the control for measuring DNA methylation is (1) a prostate cancer sample known to respond to ADT or (2) a reference value or range of reference values representing a prostate cancer sample known to respond to ADT; and (ii) administering ADT to the subject, thereby treating the prostate cancer, or (iii) measuring:

increased mRNA expression of TTC27, STMN1, and CSPG5 and decreased mRNA expression of FOSB and FKBP6 in a prostate cancer sample from the subject relative to a control for measuring mRNA expression, wherein the control for measuring expression is (1) a prostate cancer sample known to respond to ADT or (2) a reference value or range of reference values representing a prostate cancer sample known to respond to ADT, and/or increased DNA methylation within the TSS 200/1500, 5' UTR, or $1^{st}$ exon regions of FKBP6 and decreased DNA methylation FOSB, TTC27, STMN1, and CSPG5 in a prostate cancer sample from the subject relative to a control for measuring DNA methylation, wherein the control for measuring DNA methylation is (1) a prostate cancer sample known to respond to ADT or (2) a reference value or range of reference values representing a prostate cancer sample known to respond to ADT; and (iv) administering radiation therapy, chemotherapy, or both, but not ADT, to the subject, thereby treating the prostate cancer.

16. The method of claim 15, further comprising at least one the following:

measuring prostate specific antigen (PSA) in a blood sample of the subject;

determining a Gleason score for the prostate cancer;

obtaining the prostate cancer sample from the subject;

contacting: a) the prostate cancer sample from the subject, and b) the control for measuring mRNA expression and/or the control for measuring DNA methylation, with one or more binding agents specific for CSPG5, FKBP6, FOSB, STMN1, and TTC27; and measuring expression, measuring DNA methylation, or both of at least one housekeeping molecule.

17. The method of claim 15, wherein:

the ADT comprises chemical castration, anti-androgen therapy, or both;

the subject has had a prostatectomy;

the prostate cancer is a primary prostate cancer; and/or the prostate cancer is a metastatic prostate cancer.

18. The method of claim 15, wherein the subject is selected to receive a prostatectomy.

19. The method of claim 15, wherein the method comprises:

measuring increased mRNA expression of TTC27, STMN1, and CSPG5 and decreased mRNA expression of FOSB and FKBP6 in a prostate cancer sample from the subject relative to a control for measuring mRNA expression, wherein the control for measuring expression is (1) a prostate cancer sample known to respond to ADT or (2) a reference value or range of reference values representing a prostate cancer sample known to respond to ADT, and/or measuring increased DNA methylation within the TSS 200/1500, 5' UTR, or $1^{st}$ exon regions of FKBP6 and decreased DNA methylation FOSB, TTC27, STMN1, and CSPG5 in a prostate cancer sample from the subject relative to a control for measuring DNA methylation, wherein the control for measuring DNA methylation is (1) a prostate cancer sample known to respond to ADT or (2) a reference value or range of reference values representing a prostate cancer sample known to respond to ADT; and administering radiation therapy, chemotherapy, or both, but not ADT, to the subject, thereby treating the prostate cancer.

* * * * *

UNITED STATES PATENT AND TRADEMARK OFFICE
CERTIFICATE OF CORRECTION

| | |
|---|---|
| PATENT NO. | : 11,299,786 B2 |
| APPLICATION NO. | : 16/504070 |
| DATED | : April 12, 2022 |
| INVENTOR(S) | : Mitrofanova et al. |

It is certified that error appears in the above-identified patent and that said Letters Patent is hereby corrected as shown below:

In the Claims

Column 70, Lines 1-2 of Claim 16, "at least one the" should read --at least one of the--.

Signed and Sealed this
Fifth Day of July, 2022

Katherine Kelly Vidal
*Director of the United States Patent and Trademark Office*

SEQUENCE LISTING

```
<160> NUMBER OF SEQ ID NOS: 5

<210> SEQ ID NO 1
<211> LENGTH: 2175
<212> TYPE: DNA
<213> ORGANISM: Homo sapiens

<400> SEQUENCE: 1
ggggaggcgc ggcgcgccgg ggacagcggc ggacggcggc ggcggcggca tgcggctcct      60
cgcgctgccc atcgtgggct gaggcggccg cagaaccggc gggaggcgcg gcggccgggc     120
gagccgaggg cgcagccagc cgggcggacc gcggacagcg gtcggggcgc cgcgccatgg     180
ggcgagccgg gggcggggc ccgggccggg ggccgccgcc actgctgctg tttctggggg      240
ccgcgctggt cctggcctct ggggccgtgc cggcgcgtga ggcgggcagc gcggttgagg     300
ccgaagagct ggtgaagggc agcccggcgt gggagccgcc tgccaacgac acgcgggaag     360 aagccggcc accagcggct ggggaagatg aggcgtcgtg gacggcgccc ggtggcgagc      420
tggccgggcc agaagaggtg ctgcaggagt cggctgcggt gaccggcacc gcctggctgg     480
aagctgacag cccaggcctg ggaggagtga ccgcagaggc gggcagcggc gatgcccagg     540
cccttccagc tacgctccag gctccccacg aggtcctcgg gcagtcaatc atgcccctg      600 ccattcctga ggctacagag gccagcgggc caccctcccc caccccggc gacaagctga      660 gcccagcttc tgaactcccc aaggagagcc ccttggaggt ttggctgaac ctgggggca      720 gcacacccga ccctcaaggg ccagagctga cttacccatt tcagggcacc ctggagcccc     780
aaccggcatc agatatcatt gacatcgact acttcgaagg actggatggt gagggtcgtg      840
gcgcagatct ggggagcttc ccagggtcac caggaacctc agagaaccac cctgatactg      900
agggagagac cccttcctgg agcctgcttg acttatacga tgatttcacc cccttcgatg     960
aatctgattt ctacccccacc acatcctttt atgatgactt ggatgaagag gaggaggaag     1020
aggaggatga caaagatgca gtaggaggtg gagacctaga agatgaaaat gagcttctag     1080
tgcccactgg gaagcctggt ctggggcccg ggacaggcca gcccaccagt cggtggcatg     1140
ctgtccctcc acagcacact ctgggtcgg tccccggcag cagcatcgcc ctcaggcccc      1200
gcccaggaga gccaggcagg gacttggcct ccagtgaaaa tggcactgag tgccgcagtg     1260
gctttgtgcg gcataacggc tcctgccggt cagtgtgcga cctcttccca agttactgtc     1320
acaatggcgg ccagtgctac ctggtggaga acatagggc cttctgcagg tgcaacacgc      1380
aggactacat ctggcacaag gggatgcgct gcgagtccat catcaccgac ttccaggtga     1440
tgtgcgtggc cgtgggctcg gctgccctcg tcctgctcct gctcttcatg atgacggtgt     1500
tctttgccaa gaagctctac ctgctcaaga cggagaatac caagctgcgt aggaccaaca    1560
aattccggac cccatctgag ctccacaatg ataacttctc cctctccacc attgccgagg     1620
gctctcaccc aaatgatgat cctagtgctc cccacaaaat ccaggaggtt ctcaagtcct     1680
```

-continued

| | |
|---|---|
| gcctgaaaga ggaggagtca tttaacatcc agaactccat gtcgcccaaa cttgagggtg | 1740 |
| gcaaaggtga ccaggctgac ttggatgtga actgtcttca gaataattta acctaaagca | 1800 |
| gagcaagaag agaggaagcg ggggtagtgg gtgggggta ggggaagaaa cattatctcc | 1860 |
| tcttgtacag agtctatttc ttgtaaccat ttgttaaact cttttctttt tctgatctca | 1920 |
| tggcatgctt ttatgtattt tgtacaggag gcaaaaaaat acttaaaata agcaaagaaa | 1980 |
| ctgaacagaa ttgcatacat tgggttgttt tttctgtgct gtctgtacat tgcttctgct | 2040 |
| gctgtgattt ctaaacctgt gctgttattc aactgacttt tttttgtact ttgacccacg | 2100 |
| tttttttgaa ataccagtaa aaacaaagt tcttgaaata aaacttttta aaagttaaa | 2160 |
| aaaaaaaaaa aaaaa | 2175 |

<210> SEQ ID NO 2
<211> LENGTH: 1640
<212> TYPE: DNA
<213> ORGANISM: Homo sapiens

<400> SEQUENCE: 2

| | |
|---|---|
| tcgcgagggc cagggccgtt ggcggcggtt ggaacgaaac gatgagtgcc tcctcgtggc | 60 |
| cccagaatgg aatgccgccg tcggtagggg tctgccgggc ataaagggc cttcggaacc | 120 |
| ccaccagagt cacagccagg gagggcagcg gggcgcacca ggccgaaggc tcacgccaca | 180 |
| gggagggcag ctaggacatg gggggaagcg cgttaaacca gggagtcctg gaagggacg | 240 |
| acgcccccgg ccagtccctg tacgagcggt taagtcagag gatgctggac atctcggggg | 300 |
| accggggcgt gctgaaggac gtcatccgag aaggagctgg agacctagtg gcgcctgatg | 360 |
| cttcggtgct agtgaaatac tcgggatacc tggaacacat ggacagaccc ttcgattcta | 420 |
| attactttag gaaaactcct cggctaatga aacttggaga ggatattaca ctgtggggca | 480 |
| tggagctggg ccttctgagc atgcggagag gagagctggc caggtttctg ttcaaaccga | 540 |
| actacgccta tggaacgctg ggctgccctc ccttgatccc cccaaacacc actgtcctgt | 600 |
| ttgagattga gctgcttgac ttcctggact gtgctgagtc agacaagttt tgtgctctct | 660 |
| cagctgagca gcaagaccaa tttccacttc agaaggtcct gaaagtggca gctacggaac | 720 |
| gggagtttgg caactaccct ttccgccaga tcgtttcta tgatgccaaa gtgagatata | 780 |
| aaagggccct attgcttctg cgccggcgat cagcaccccc tgaagagcag cacctggtgg | 840 |
| aggccgccaa gcttcctgtt ctcctgaacc tgtccttac atacctgaag ctagaccgac | 900 |
| ccaccatagc cctgtgctat ggagagcagg cttttgatcat tgaccaaaag aatgccaagg | 960 |
| ccctcttcag gtgtggacag gcttgtcttc tcctgactga gtatcaaaag gcccgggatt | 1020 |
| ttctagttcg agcccagaag gagcaaccct tcaatcatga catcaataat gagctgaaga | 1080 |
| aactggctag ctgttacagg gactatgtgg ataaagagaa agaaatgtgg caccgcatgt | 1140 |
| tcgcgccctg tggcgatggt tctacagcag gagaaagttg aaggttcttc acctaccaac | 1200 |
| gaggggagag agctgtggtt ctccatcatt gggggagtgg aagggagctc ccagcgcagc | 1260 |
| cgtggcagcc accttccagg agcaggggct ggaatgtcct gtggccgcat ctctcatgga | 1320 |
| cgcggctgaa acgtgttttc acaggtgctg ttttctgttt tccgtgttcg taacagaagg | 1380 |
| gaggggaaag cgcagctact gacaagtaga acactgctac ttttttaag gcagtttctt | 1440 |
| gttttttag acggaattag tccttggctt ccctcccagt cccagccctg cttccggctg | 1500 |
| cgaatgtccc tgagtcaaca ccaatagaga ttgctttgtg tattttgtag ggttctctgt | 1560 |
| tttgaagaca gaattatgtt acaaatgttt ttgttgtaaa taaataaaac acttccttgt | 1620 |

```
ccttgcaaga tccagtataa                                              1640

<210> SEQ ID NO 3
<211> LENGTH: 1640
<212> TYPE: DNA
<213> ORGANISM: Homo sapiens

<400> SEQUENCE: 3
tcgcgagggc cagggccgtt ggcggcggtt ggaacgaaac gatgagtgcc tcctcgtggc      60
cccagaatgg aatgccgccg tcggtagggg tctgccgggc ataaaggggc cttcggaacc     120
ccaccagagt cacagccagg gagggcagcg gggcgcacca ggccgaaggc tcacgccaca     180
gggagggcag ctaggacatg gggggaagcg cgttaaacca gggagtcctg aaggggacg      240 acgcccccgg ccagtccctg tacgagcggt taagtcagag gatgctggac atctcggggg     300
accggggcgt gctgaaggac gtcatccgag aaggagctgg agacctagtg gcgcctgatg     360
cttcggtgct agtgaaatac tcgggatacc tggaacacat ggacagaccc ttcgattcta     420
attactttag gaaaactcct cggctaatga aacttggaga ggatattaca ctgtggggca     480
tggagctggg ccttctgagc atgcggagag gagagctggc caggtttctg ttcaaaccga     540
actacgccta tggaacgctg ggctgccctc ccttgatccc cccaaacacc actgtcctgt     600
ttgagattga gctgcttgac ttcctggact gtgctgagtc agacaagttt tgtgctctct     660
cagctgagca gcaagaccaa tttccacttc agaaggtcct gaaagtggca gctacggaac     720
gggagtttgg caactacctt ttccgccaga tcgtttcta tgatgccaaa gtgagatata     780
aagggcccct attgcttctg cgccggcgat cagcacccc tgaagagcag cacctggtgg     840
aggccgccaa gcttcctgtt ctcctgaacc tgtcctttac atacctgaag ctagaccgac     900
ccaccatagc cctgtgctat ggagagcagg ctttgatcat tgaccaaaag aatgccaagg     960
ccctcttcag gtgtggacag gcttgtcttc tcctgactga gtatcaaaag gcccgggatt    1020
ttctagttcg agcccagaag gagcaaccct tcaatcatga catcaataat gagctgaaga    1080
aactggctag ctgttacagg gactatgtgg ataaagagaa agaaatgtgg caccgcatgt    1140
tcgcgccctg tggcgatggt tctacagcag agaaagttg aaggttcttc acctaccaac    1200
gaggggagag agctgtggtt ctccatcatt gggggagtgg aagggagctc ccagcgcagc    1260
cgtggcagcc accttccagg agcaggggct ggaatgtcct gtggccgcat ctctcatgga    1320
cgcggctgaa acgtgttttc acaggtgctg ttttctgttt tccgtgttcg taacagaagg    1380
gaggggaaag cgcagctact gacaagtaga acactgctac tttttttaag gcagtttctt    1440 gttttttttag acggaattag tccttggctt ccctcccagt cccagccctg cttccggctg    1500
cgaatgtccc tgagtcaaca ccaatagaga ttgctttgtg tattttgtag ggttctctgt    1560
tttgaagaca gaattatgtt acaaatgttt ttgttgtaaa taaataaaac acttccttgt    1620
ccttgcaaga tccagtataa                                              1640

<210> SEQ ID NO 4
<211> LENGTH: 1730
<212> TYPE: DNA
<213> ORGANISM: Homo sapiens

<400> SEQUENCE: 4
atcaccgggc gtccgctccg ggtgccgtga gaggagacaa tagggggcgt gggccctcgt       60
ttacctccct ccctccctcc cttccctgcg ggccccgccg ggttccccat tgtctgaagg      120
```

-continued

```
gacggggcgg tgccccaggg accagcggct ttaggaccaa actgcgggca gccagggccg    180
cgaccctccc tgcgaccgtc ccctggcgac cgcagctggt gattgagggg cggcgctccc    240
gggccccacg agggttcttc tgtcttcgcg gccggacgcg cggacagcgt gggtggcggc    300
aggactttcc ttatcccagt tgattgtgca gaatacactg cctgtcgctt gtcttctatt    360
caccatggct tcttctgata tccaggtgaa agaactggag aagcgtgcct caggccaggc    420
ttttgagctg attctcagcc ctcggtcaaa agaatctgtt ccagaattcc ccctttcccc    480
tccaaagaag aaggatcttt ccctggagga aattcagaag aaattagaag ctgcagaaga    540
aagacgcaag tcccatgaag ctgaggtctt gaagcagctg gctgagaaac gagagcacga    600
gaaagaagtg cttcagaagg caatagaaga gaacaacaac ttcagtaaaa tggcagaaga    660
gaaactgacc cacaaaatgg aagctaataa agagaaccga gaggcacaaa tggctgccaa    720
actgaacgt tgcgagaga aggataagca cattgaagaa gtgcggaaga acaaagaatc    780
caaagaccct gctgacgaga ctgaagctga ctaatttgtt ctgagaactg actttctccc    840
catcccttc ctaaatatcc aaagactgta ctggccagtc tcattttatt ttttccctcc    900
tgacaaatat tttagaagct aatgtaggac tgtataggta gatccagatc cagactgtaa    960
gatgttgttt taggggctaa aggggagaaa ctgaaagtgt tttactcttt ttctaaagtg   1020
ttggtctttc taatgtagct attttcttg ttgcatcttt tctacttcag tacacttggt   1080
gtactgggtt aatggctagt actgtattgg ctctgtgaaa acatatttgt gaaagagta    1140
tgtagtggct tcttttgaac tgttagatgc tgaatatctg ttcactttc aatcccaatt   1200
ctgtcccaat cttaccagat gctactggac ttgaatggtt aataaaactg cacagtgctg   1260
ttggtggcag tgacttcttt tgagttaggt taataaatca agccatagag cccctcctgg   1320
ttgatacttg ttccagatgg ggcctttggg gctggtagaa atacccaacg cacaaatgac   1380
cgcacgttct ctgccccgtt tcttgcccca gtgtggtttg cattgtctcc ttccacaatg   1440
actgctttgt ttggatgcct cagcccaggt cagctgttac tttctttcag atgtttattt   1500
gcaaacaacc attttttgtt ctgtgtccct tttaaaaggc agattaaaag cacaagcgtg   1560
tttctagaga acagttgaga gagaatctca agattctact tggtggtttg cttgctctac   1620
gttacaggtg gggcatgtcc tcatcctttc ctgccataaa agctatgaca cgagaatcag   1680
aatattaata aaactttatg tactgctgta gcaaaaaaaa aaaaaaaaa                1730
```

<210> SEQ ID NO 5
<211> LENGTH: 2953
<212> TYPE: DNA
<213> ORGANISM: Homo sapiens

<400> SEQUENCE: 5

```
cccaacaggc tccttactca agctcgggtt cttctcctag gcggaagcca gaccagagag     60
cgtgcgtgtt tttcccaggg tgccccgcgc tgctgttatg gccgcctcct tgaggtagta    120
tccgcacatg gaattctagg gccgcaggtg tatttacggt aactgtcgcc actagatttc    180
agcgcctttg gactctcctg ttttcacttt cttttgttga ctcccgtgtg gccctcgtgg    240
gagcctgttt tggctgcagc ggtgtctggg gtgatgtgga ccccggagct ggcaattctg    300
aggggattcc ccactgaggc tgagcggcag caatggaaac aggaggggt cgtcggttca     360
gagagtggat ctttcctaca attgctgctg gagggaact atgaagccat attcttaaat    420
tcaatgactc aaaatatttt taattcaaca acaaccgctg aagaaaagat tgatagctac    480
ctggagaagc aggtagtaac attcctggat tactcaacag atttggacac aacggaaaga    540
```

```
caacagttga tatttctact tggtgtgagc agtttgcaac ttttttgttca gagcaactgg    600 acggggcccc ctgttgactt acaccctcag gactttttgt catctgtttt gttccagcaa    660
ttcagtgagg ttaaaggact ggatgcattt gttctgagcc tgctcactct agatggtgaa    720
tcaatctaca gcctgacctc gaagcctata ctactgttat tagcacgcat tatcctagtg    780
aatgtaagac ataaactgac agctattcag agcttgccat ggtggacttt gagatgtgtg    840
aatattcatc agcatttgct tgaggaacgc tcacctctgc tttttactct tgccgaaaac    900
tgtattgatc aagtgatgaa actacagaat ctgtttgtag atgattcagg tcgatatttg    960
gctattcaat ccatctgga atgtgcatat gtgtttttat attattatga gtacagaaaa   1020
gcaaaagatc agttggatat tgctaaggac atcagccaat tacaaattga tttgacaggt   1080
gctttgggaa aaagaacacg gttccaggaa aattatgtgg cacaactgat tctagatgta   1140
agaagggaag gggatgtcct ttcaaattgt gaattcactc cagcacccac tcctcaggaa   1200
catttaacca agaatcttga gctcaatgat gacaccattc tgaatgacat aaagttagca   1260
gattgtgaac agttccagat gccggatctg tgtgctgaag agatcgctat tattcttgga   1320
atctgcacta ttttcaaaa gaataaccca gtgcacacat taactgaagt ggagcttctg   1380
gcatttacat catgtttgct ttcacaacca aagttctggg ccattcagac atcagccttg   1440
atcctccgga caaaacttga gaaaggaagt actcgccgag tggaacgggc aatgaggcag   1500
acacaggctc ttgcagacca atttgaagat aaaactacat ctgtattgga acgcctgaag   1560 atttttctatt gctgtcaagt accacctcac tgggccattc agcgccaact tgcaagtttg   1620
ctctttgagt tgggatgtac cagttcagcc cttcagatat ttgaaaagct agaaatgtgg   1680
gaagatgttg tcatttgtta tgaaagagcc gggcagcacg gaaaggcaga agaaatcctt   1740
agacaagagc tggagaaaaa agaaacgcct agtttatact gcttgcttgg agatgtcctc   1800
ggagaccatt cttgctatga caaggcctgg gagttgtccc ggtaccgcag tgctcgtgct   1860
cagcgctcca aagccctcct tcatcttcgg aacaaggagt ttcaagagtg tgtagagtgc   1920
ttcgaacgct cggttaagat taatcccatg cagctcgggg tgtggttttc tctcggttgt   1980
gcctatttgg ccttggaaga ctatcaaggt tcagcaaagg catttcagcg ctgtgtgact   2040
ctagaacccg ataatgctga agcttggaac aatttgtcaa cttcctatat ccgattaaaa   2100
caaaaagtaa aagcttttag aactttacaa gaagctctca gtgtaactac tgaacactgg   2160
cagatttggg aaaactacat cctcaccagc actgacgttg gggaattttc agaagccatt   2220
aaagcttatc accggctctt ggacttacgt gacaaataca aagatgttca ggtccttaaa   2280
attctagtca gggcagtgat tgatgggatg actgatcgaa gtggagatgt tgcaactggc   2340
ctcaaaggaa agctgcagga gttatttggc agagtgactt caagagtgac aaatgatgga   2400
gaaatctgga ggctgtatgc ccacgtatat ggaaatgggc agagtgaaaa gcctgatgaa   2460
aatgaaaagg cattccagtg cctctcaaag gcatacaagt gtgacaccca gtccaattgt   2520
tgggagaaag atattacatc atttaaggaa gttgttcaaa gagccttagg acttgcacat   2580
gtggccataa aatgcagtaa aaacaaatcc agttcccaag aagctgtaca aatgctttct   2640
tctgttcgac tcaatttacg gggcttgtta tctaaagcaa agcaacttt tacagatgtg   2700 gcaactggag aaatgtccag ggaattagct gatgacataa cagctatgga caccttagtg   2760
acagagctcc aagacctaag caaccagttt cgaaatcagt attgattctg ctggaagcag   2820
attctggaaa aggtgctttc acctgctggt aaaagataca tctgtatatc tgaaatgcaa   2880
```

```
gatattgatt tttaaaataa atttgtttta tgacttaaaa aaaaaaaaaa aaaaaaaaaa    2940
aaaaaaaaaa aaa                                                      2953
```